United States Patent
Sareen et al.

(10) Patent No.: US 10,702,216 B2
(45) Date of Patent: Jul. 7, 2020

(54) METHOD AND SYSTEM FOR BODY SCANNING AND DISPLAY OF BIOMETRIC DATA

(71) Applicants: Raj Sareen, Rolling Hills, CA (US); Jason Delevan, Sunland, CA (US); Stephen Randolph Smith, III, Gardena, CA (US); Bobby H. Parkinson, Jr., La Mirada, CA (US)

(72) Inventors: Raj Sareen, Rolling Hills, CA (US); Jason Delevan, Sunland, CA (US); Stephen Randolph Smith, III, Gardena, CA (US); Bobby H. Parkinson, Jr., La Mirada, CA (US)

(73) Assignee: Styku, LLC, Los Angeles, CA (US)

( * ) Notice: Subject to any disclaimer, the term of this patent is extended or adjusted under 35 U.S.C. 154(b) by 608 days.

(21) Appl. No.: 15/146,744

(22) Filed: May 4, 2016

(65) Prior Publication Data

US 2016/0247017 A1    Aug. 25, 2016

Related U.S. Application Data

(63) Continuation-in-part of application No. 14/956,303, filed on Dec. 1, 2015, which is a continuation-in-part of application No. 14/941,144, filed on Nov. 13, 2015, which is a continuation-in-part of application No. 13/159,401, filed on Jun. 13, 2011, which is a
(Continued)

(51) Int. Cl.
| | |
|---|---|
| *A61B 5/00* | (2006.01) |
| *H04N 5/232* | (2006.01) |
| *G06T 7/60* | (2017.01) |
| *A61B 5/107* | (2006.01) |
| *G06K 9/00* | (2006.01) |
| *G06T 19/00* | (2011.01) |

(52) U.S. Cl.
CPC .......... *A61B 5/7475* (2013.01); *A61B 5/0064* (2013.01); *A61B 5/0077* (2013.01); *A61B 5/1079* (2013.01); *A61B 5/744* (2013.01); *G06K 9/00369* (2013.01); *G06T 7/60* (2013.01); *G06T 19/00* (2013.01); *H04N 5/23293* (2013.01); *G06T 2200/08* (2013.01); *G06T 2207/30124* (2013.01)

(58) Field of Classification Search
CPC ... A61B 5/7475; A61B 5/0064; A61B 5/0077; A61B 5/1079; A61B 5/744
USPC .......................................................... 348/47
See application file for complete search history.

(56) References Cited

U.S. PATENT DOCUMENTS

| | | | |
|---|---|---|---|
| 7,253,766 B2* | 8/2007 | Foote .................... | G01S 13/003 342/179 |
| 2002/0138170 A1* | 9/2002 | Onyshkevych ........ | G06Q 30/06 700/130 |

(Continued)

*Primary Examiner* — Clifford Hilaire
*Assistant Examiner* — Kristin Dobbs
(74) *Attorney, Agent, or Firm* — Ivan Posey, Esq.; Leech Tishman Fuscaldo & Lampl

(57) ABSTRACT

A system for scanning a body to create scan data comprises a processor, a range camera capable of capturing at least a first set of depth images of the body rotated to 0 degrees, and at least a second set of depth images of the body rotated to x degrees, wherein x is >0 degrees, and x <360 degrees. A set of computer instructions are executable on a processor capable of creating biometrics based on extracted body measurement from the body scan.

20 Claims, 74 Drawing Sheets

Related U.S. Application Data continuation-in-part of application No. 13/008,906, filed on Jan. 19, 2011.

(60) Provisional application No. 61/352,930, filed on Jun. 8, 2010.

(56) References Cited

U.S. PATENT DOCUMENTS

| | | | | |
|---|---|---|---|---|
| 2010/0295854 A1* | 11/2010 | Miller | ................ | G06K 9/00208 |
| | | | | 345/427 |
| 2011/0193939 A1* | 8/2011 | Vassigh | ................... | G06F 3/011 |
| | | | | 348/46 |

* cited by examiner

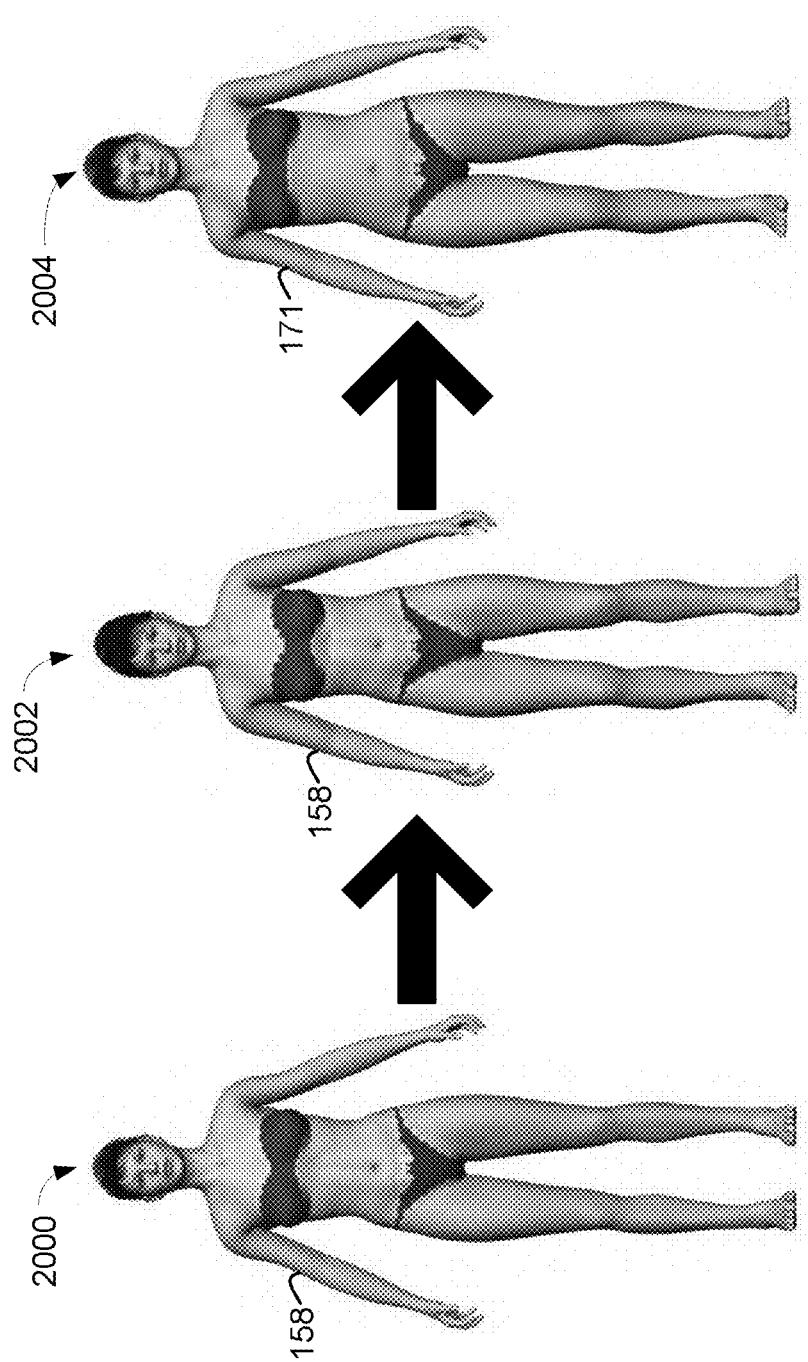

Figure 88
(prior art)

| Description | Women | Men |
|---|---|---|
| Essential Fat | 10-13% | 2-5% |
| Athletes | 14-20% | 6-13% |
| Fitness | 21-24% | 14-17% |
| Acceptable | 25-31% | 18-24% |
| Obesity | >32% | >25% |

Figure 89
(prior art)

| | |
|---|---|
| Little to no exercise | Daily kilocalories needed = BMR x 1.2 |
| Light exercise (1-3 days per week) | Daily kilocalories needed = BMR x 1.375 |
| Moderate exercise (3-5 days per week) | Daily kilocalories needed = BMR x 1.55 |
| Heavy exercise (6-7 days per week) | Daily kilocalories needed = BMR x 1.725 |
| Very heavy exercise (twice per day, extra heavy workouts) | Daily kilocalories needed = BMR x 1.9 |

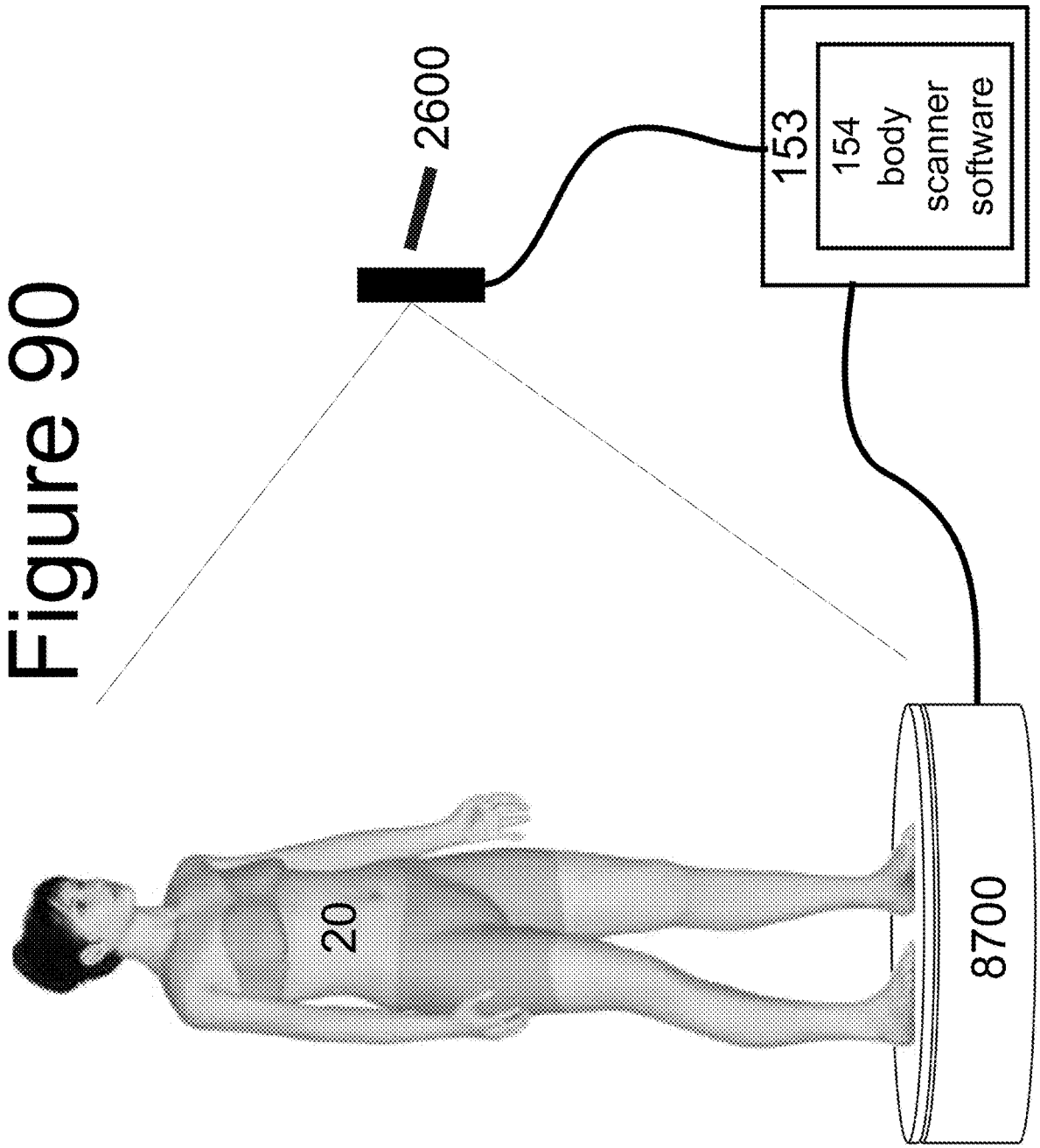

METHOD AND SYSTEM FOR BODY SCANNING AND DISPLAY OF BIOMETRIC DATA

RELATED APPLICATION INFORMATION

This application is a Continuation-In-Part of U.S. application Ser. No. 14/956,303, entitled "Method and System for Determining Biometrics from Body Surface Imaging Technology", filed Dec. 1, 2015, which is a Continuation-In-Part of U.S. application Ser. No. 14/941,144, entitled "Cloud Server Body Scan Data System", filed Nov. 13, 2015, which is a Continuation-In-Part of U.S. application Ser. No. 13/159,401, entitled "System And Method For Body Scanning And Avatar Creation", filed Jun. 13, 2011, which is a Continuation-In-Part of U.S. application Ser. No. 13/008,906 filed Jan. 19, 2011 entitled "System And Method For 3d Virtual Try-On Of Apparel On An Avatar," which claims the benefit of Application Ser. No. 61/352,390, entitled "System And Method For 3D Virtual Try-On Of Apparel On An Avatar", filed Jun. 8, 2010, the contents of which are incorporated in this disclosure by reference in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to a method and system for body scanning, avatar creation and determination and display of biometric data. More specifically, a scanning system and method using one or more range cameras and a rotating platform produces an avatar and provides scan data and biometrics.

SUMMARY OF THE INVENTION

In order to solve the problems and shortcomings of the prior art, an apparatus is disclosed for 3D virtual try-on of apparel on an avatar. According to one preferred embodiment, the system for 3D virtual try-on of apparel on an avatar is disclosed. According to one preferred embodiment, a method of fitting a garment on a person's body online comprises receiving specifications of a garment, receiving body specifications of one or more fit models, receiving one or more grade rules, receiving one or more fabric specifications, and receiving specifications of a consumer's body. The value of one or more fabric constants are determined according to the received one or more fabric specifications. One or more virtual garments in graded sizes are created and stored in a database based on the received garment specifications and fabric constants. Moreover, one or more graded virtual fit models are created and stored in a database based on the received specifications of the fit model. Each virtual garment is draped on the related virtual fit model to create a fit-model drape. An avatar is received or created to represent a consumer's body shape. A selected one of the virtual garments is determined that represents a closest size for fitting on the avatar. The selected virtual garment is then re-draped on the consumer avatar. The consumer drape can then be viewed in 3D on the web or in a software application on any computing device. Data regarding the result of the virtual try-on process can then be utilized by the retailer, the consumer, and/or a third party. This virtual try-on data can be in the form of visual data or quantitative data that can be interpreted to determine the goodness of a garment's fit. Specifically, consumers can be presented with such data to assess the appropriate size and the goodness of a garment's fit, retailers can utilize such data for assessing how their garments are performing on their customer's bodies, and finally, such data can be used as a predictive tool for recommending further garments to consumers (e.g., in a predictive, search or decision engine).

In another preferred embodiment, a method of fitting a garment on a person's body online comprises receiving specifications of a garment, receiving specifications of a fit model, receiving a digital pattern corresponding to the fit model, receiving one or more grade rules, and receiving one or more fabric specifications. One or more graded digital patterns corresponding to one or more available sizes are calculated and stored in a database based on the received specifications of the garment, the received specifications of the fit model, the received digital pattern corresponding to the fit model, and the grade rules. The value of one or more fabric constants are determined according to the received one or more fabric specifications. An avatar representing the person's body, and a selected one of the available sizes is determined that represents a closest size for fitting on the avatar. A virtual garment is created from the stored graded digital pattern corresponding to selected available size. The selected virtual garment is then draped on the avatar according to the fabric constants.

According to yet another preferred embodiment, a method of fitting a garment on a person's body online comprises receiving specifications of a garment, receiving specifications of a fit model, receiving one or more grade rules, and receiving one or more fabric specifications. A virtual fit model is calculated and stored based on the received specifications of the garment, and the received specifications of the fit model. The values of one or more fabric constants are determined according to the received one or more fabric specifications. An avatar representing the person's body is received, and a selected size for the person's body is determined according to the received one or more grade rules. A virtual garment is created in the selected size according to the virtual fit model, the one or more grade rules, and the selected size. The selected virtual garment is then draped on the avatar according to the fabric constants.

In yet another preferred embodiment, a computer program product is stored on computer readable medium containing executable software instructions for fitting one or more garments on a person's body, the executable software instructions.

In yet another preferred embodiment, a system for scanning a body comprises a processor, a range camera capable of capturing at least a first set of depth images of the body rotated to 0 degrees, and at least a second set of depth images of the body rotated by a mechanical or electrical rotation device or platform to x degrees, wherein x is >0 degrees, and x <360 degrees, a first set of computer instructions executable on the processor capable of calculating a first set of three dimensional points from the first set of depth images and a second set of three dimensional points from the second set of depth images, a second set of computer instructions executable on the processor capable of rotating and translating the first and second set of three dimensional points into a final set of three dimensional points; and a third set of computer instructions executable on the processor capable of creating a three dimensional mesh from the final set of three dimensional points; a third set of computer instructions executable on a processor capable of extracting body measurements from the final set of three dimensional points; and a fourth set of computer instructions executable on a processor capable of creating biometrics based on the extracted body measurements.

BRIEF DESCRIPTION OF THE DRAWINGS

FIG. 17 is a flow diagram illustrating steps for creating an avatar according to one embodiment;

FIG. 88 is a prior art chart showing the ACE rankings for each gender;

FIG. 89 is a prior art a chart illustrating the Harris Benedict Activity Level rankings;

FIG. 90 is a diagrammatic illustration of a single range camera scanner system that rotates the body using a mechanical or electrical rotating platform according to one embodiment.

DETAILED DESCRIPTION OF THE PREFERRED EMBODIMENTS

Figure 1:
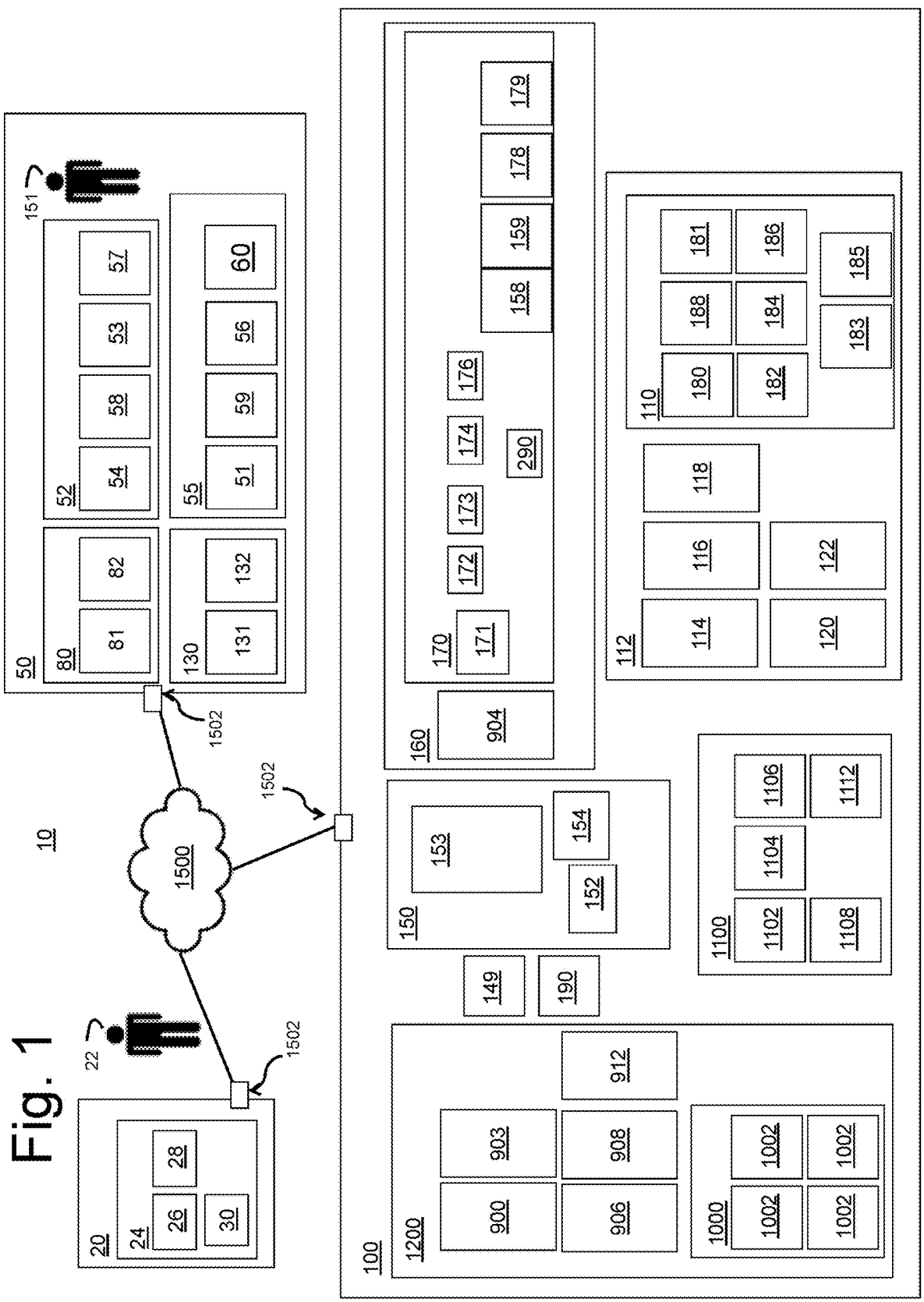
FIG. 1 is a diagram that illustrates components of one embodiment of a system for providing online virtual try-on apparel on an avatar.

For the purpose of illustrating the invention, there is shown in the accompanying drawings several embodiments of the invention. However, it should be understood by those of ordinary skill in the art that the invention is not limited to the precise arrangements and instrumentalities shown therein and described below.

The system for online virtual try-on of apparel on an avatar is disclosed in accordance with preferred embodiments of the present invention is illustrated in FIGS. 1-19 wherein like reference numerals are used throughout to designate like elements.

Figure 2:
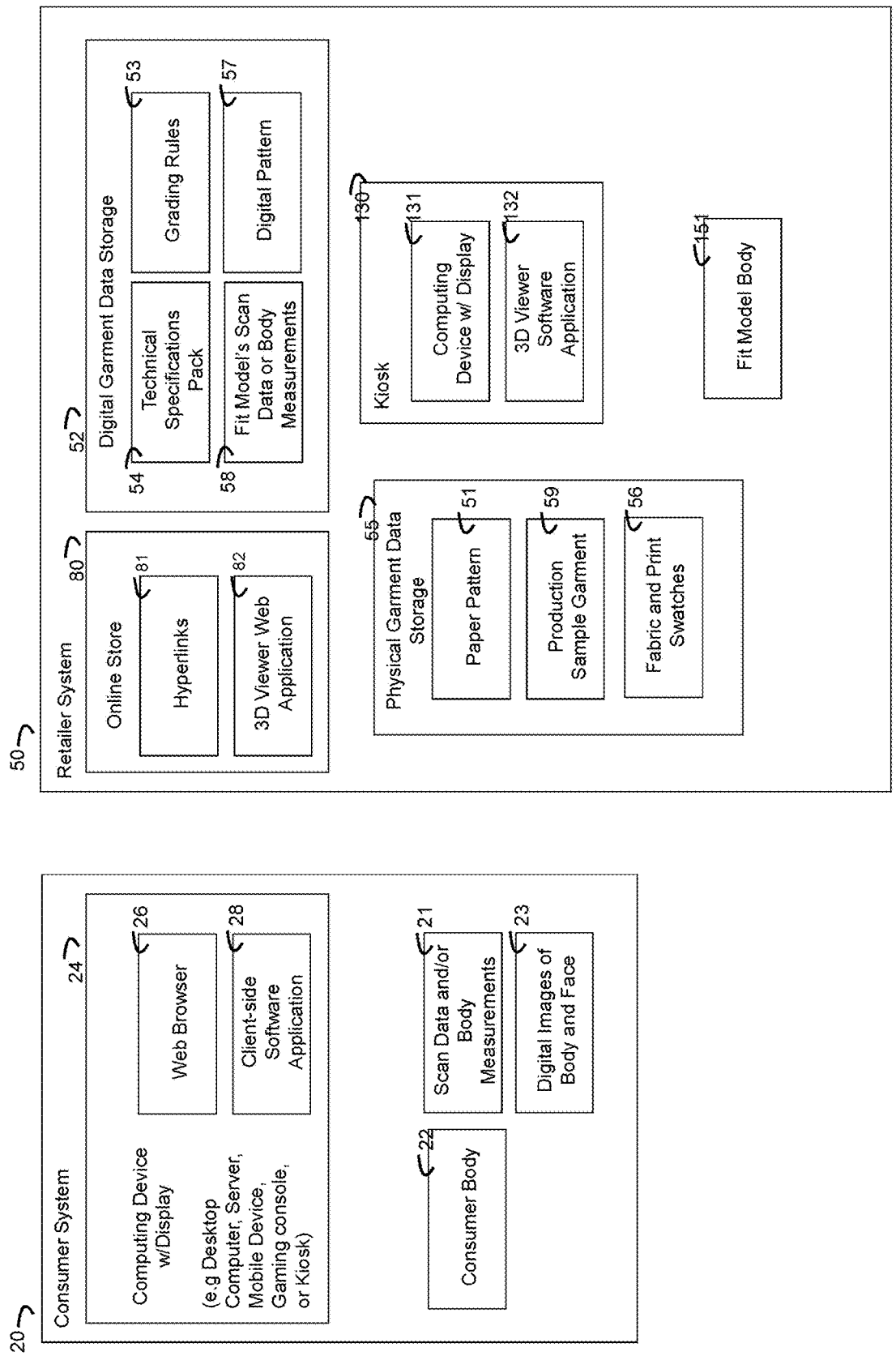
FIG. 2 is a diagram that illustrates further detail of the consumer system and a retail system of FIG. 1.
Figure 3:
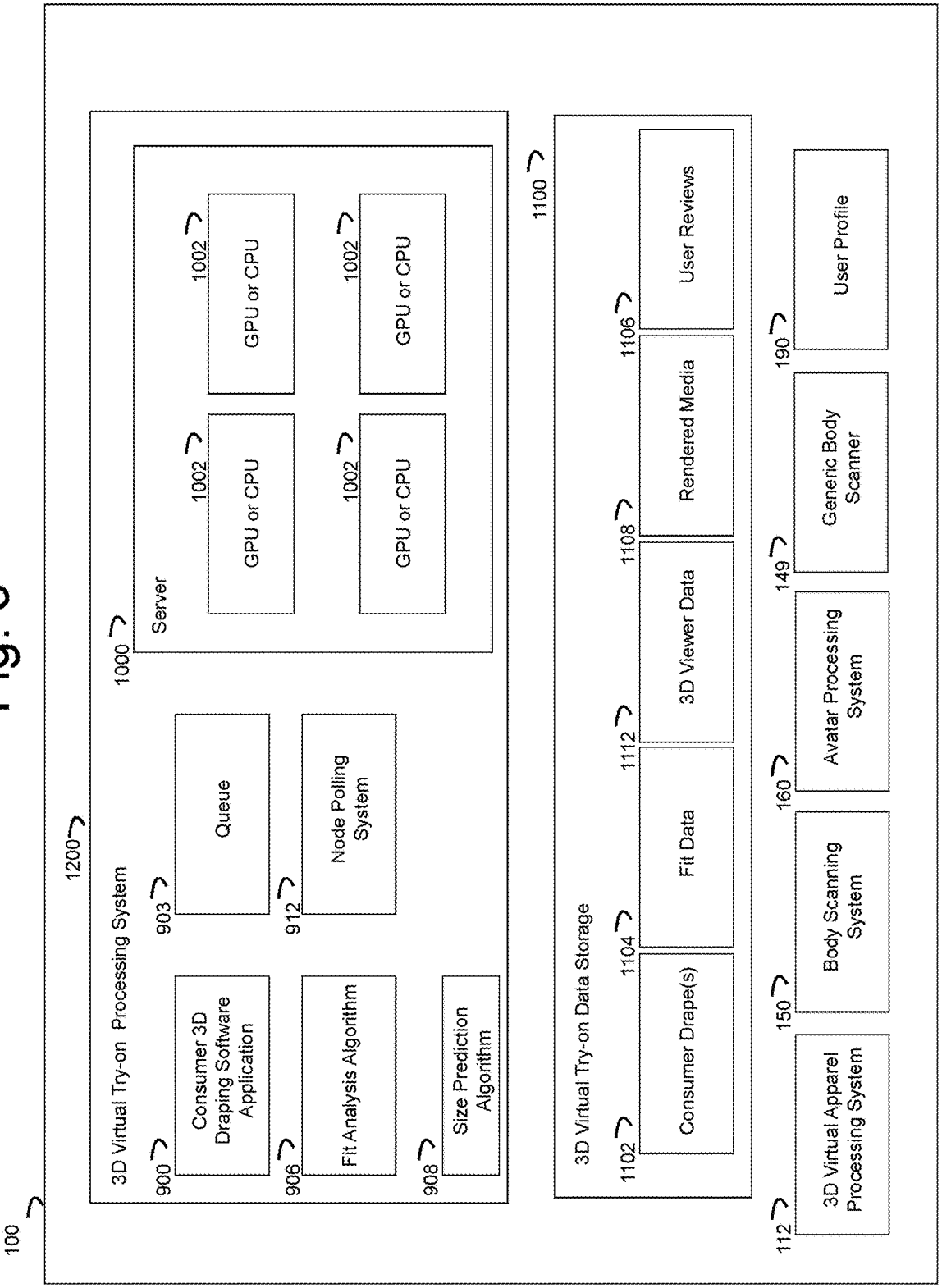
FIG. 3 is a diagram that illustrates further detail of the virtual try-on system of FIG. 1.
Figure 4:
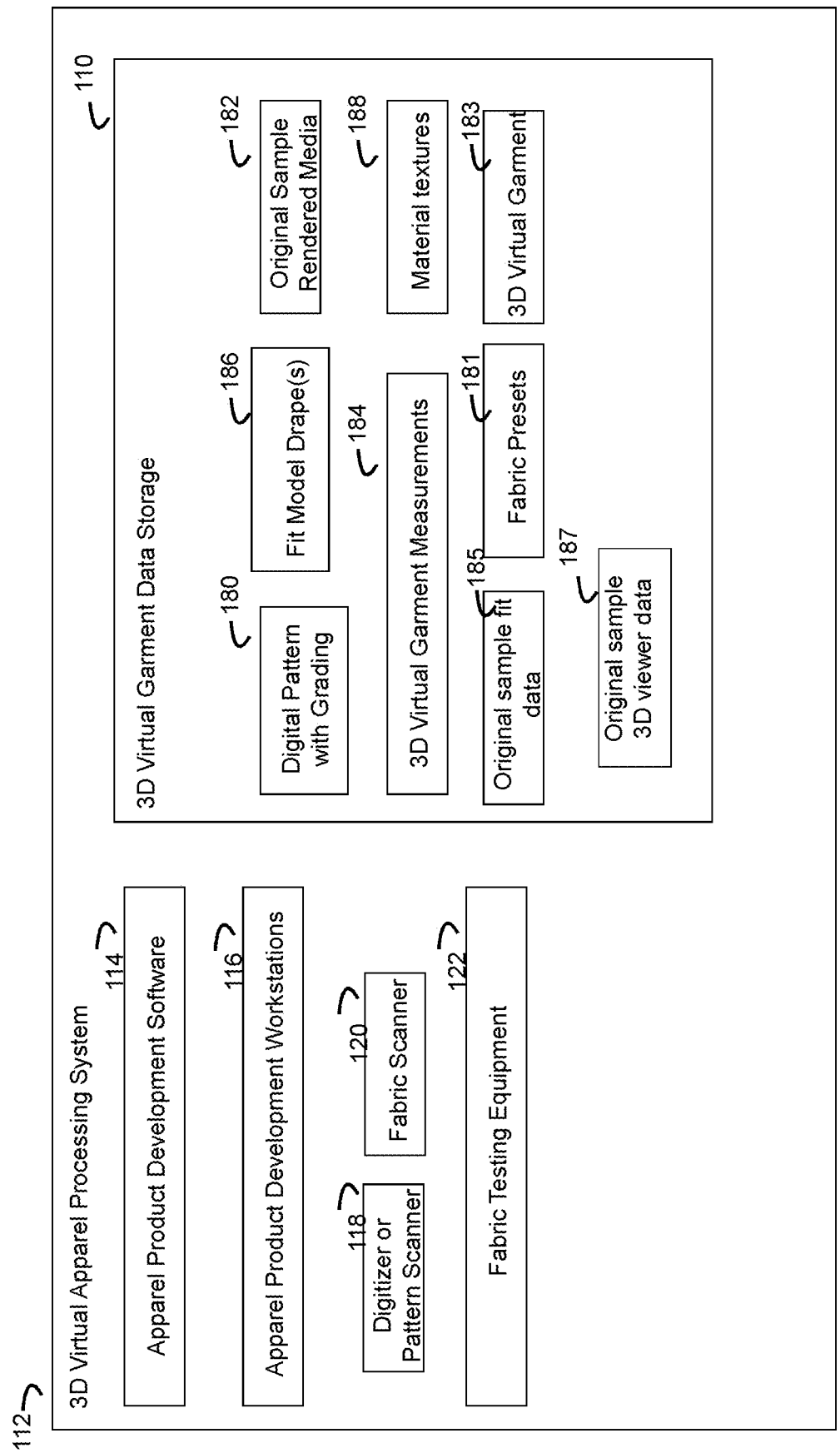
FIG. 4 is a diagram that illustrates further detail of the 3D virtual apparel system of FIG. 1.
Figure 5:
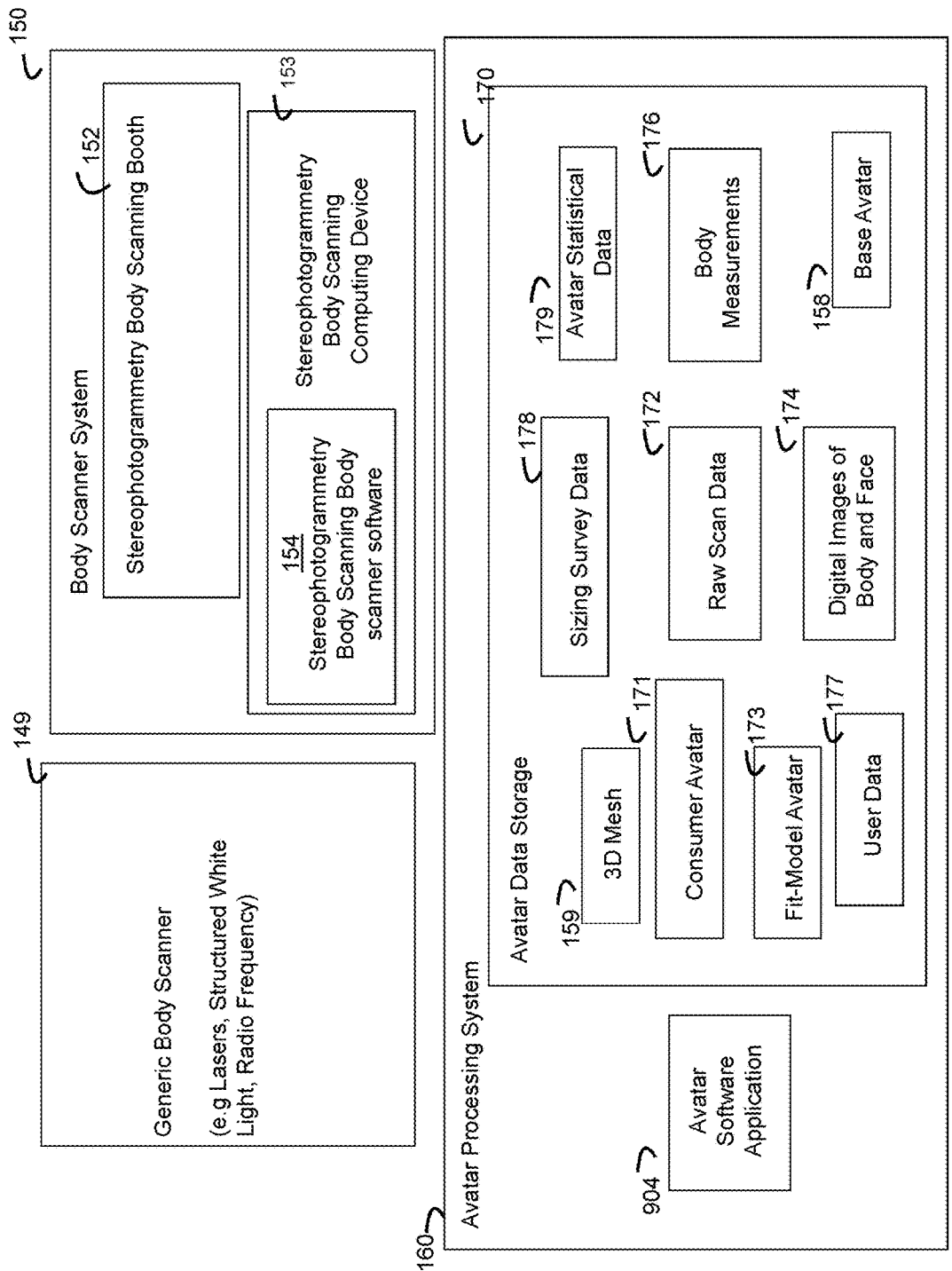
FIG. 5 is a diagram that illustrates further detail of the body scanner system used with the system of FIG. 1.

FIG. 1 is a diagram that illustrates components of one embodiment of a system 10 for providing online virtual try-on apparel on an avatar. FIG. 2 is a diagram that illustrates further detail of the consumer system and a retail system of FIG. 1. FIG. 3 is a diagram that illustrates further detail of the virtual try-on system of FIG. 1. FIG. 4 is a diagram that illustrates further detail of the 3D virtual apparel system of FIG. 1. FIG. 5 is a diagram that illustrates further detail of the body scanner system used with the system of FIG. 1.

A three dimensional (3D) virtual apparel processing system 112 gathers all or any combination of the following data available from retailer 50: (1) paper pattern 51, (2) grading rules 53, (3) technical pack 54, (4) digital pattern 57, (5) fit model's scan data or measurements 58, (6) production sample garment, or (7) fabric swatches, where data displayed in FIG. 1 in physical garment storage 55 or digital garment data storage 52. Moreover, data from stereophotogrammetry system 150 is sent to system 112. System 112 then processes all gathered data and may make output data available to all other systems. In one embodiment, application service provider (ASP) 100 may receive data from consumer system 20 and stereophotogrammetry system 150. In one embodiment the ASP 100 and consumer system 20 may be connected through a wide area network 1500, wherein each have network connections 1502 to facilitate such connection. Retailer system 50 may also be similarly connected to network 1500. For example, the wide area network 1500 may comprise the internet, and the network connections 1502 may comprise network routers, cards, etc. commonly used to connect to the internet. In one embodiment, it may be advantageous to provide a high speed, or wideband, network connection 1502, such as a fibre optic, T1, T2, or other commonly used wideband typology. ASP 100, which may utilize off the shelf server software and network technology, then processes all the data and provides services for system 10. The term garment and apparel may be used interchangeably herein, both in the plural and the singular.

Figure 6:
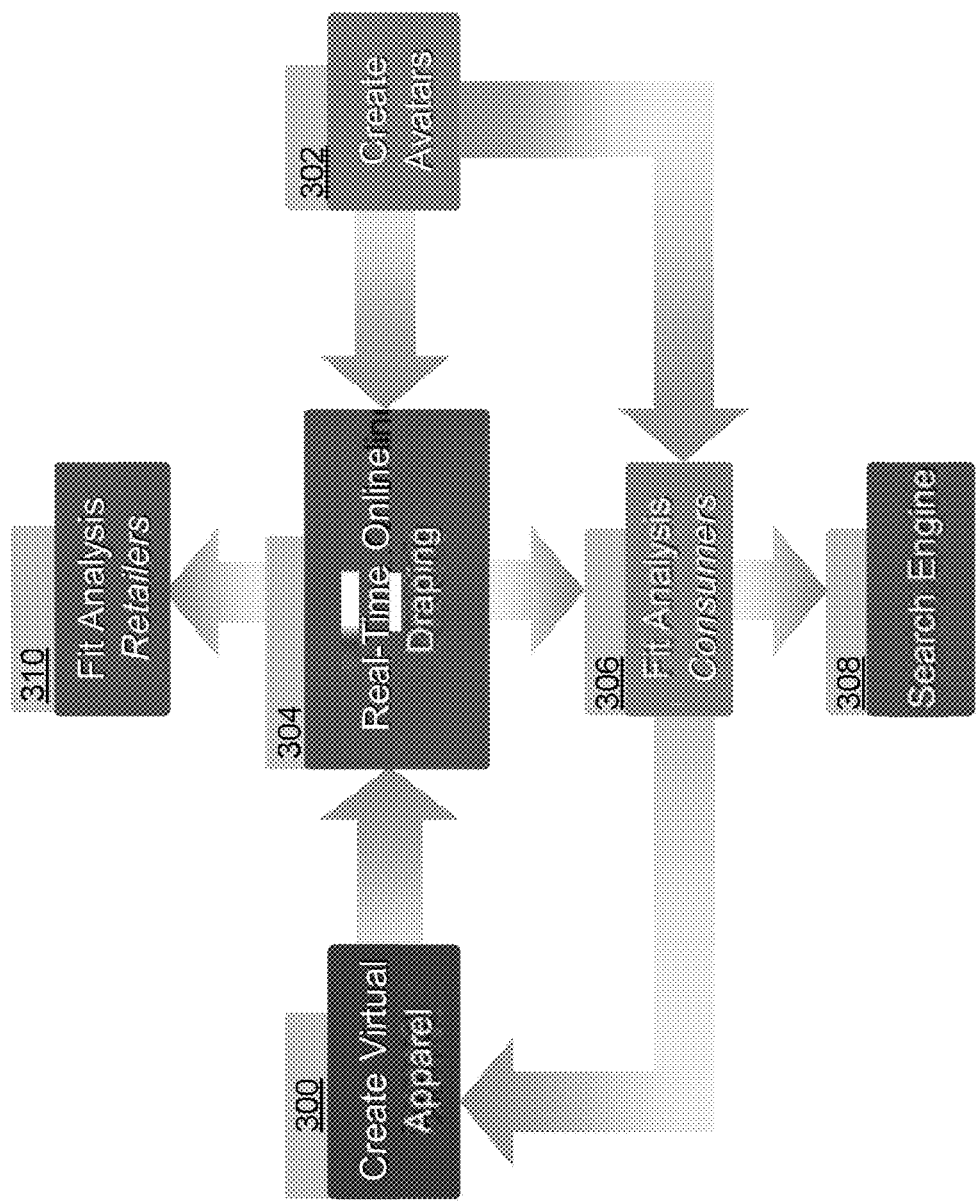
FIG. 6 is a flow diagram that illustrates a general view of high level method steps performed by one embodiment.
Figure 7:
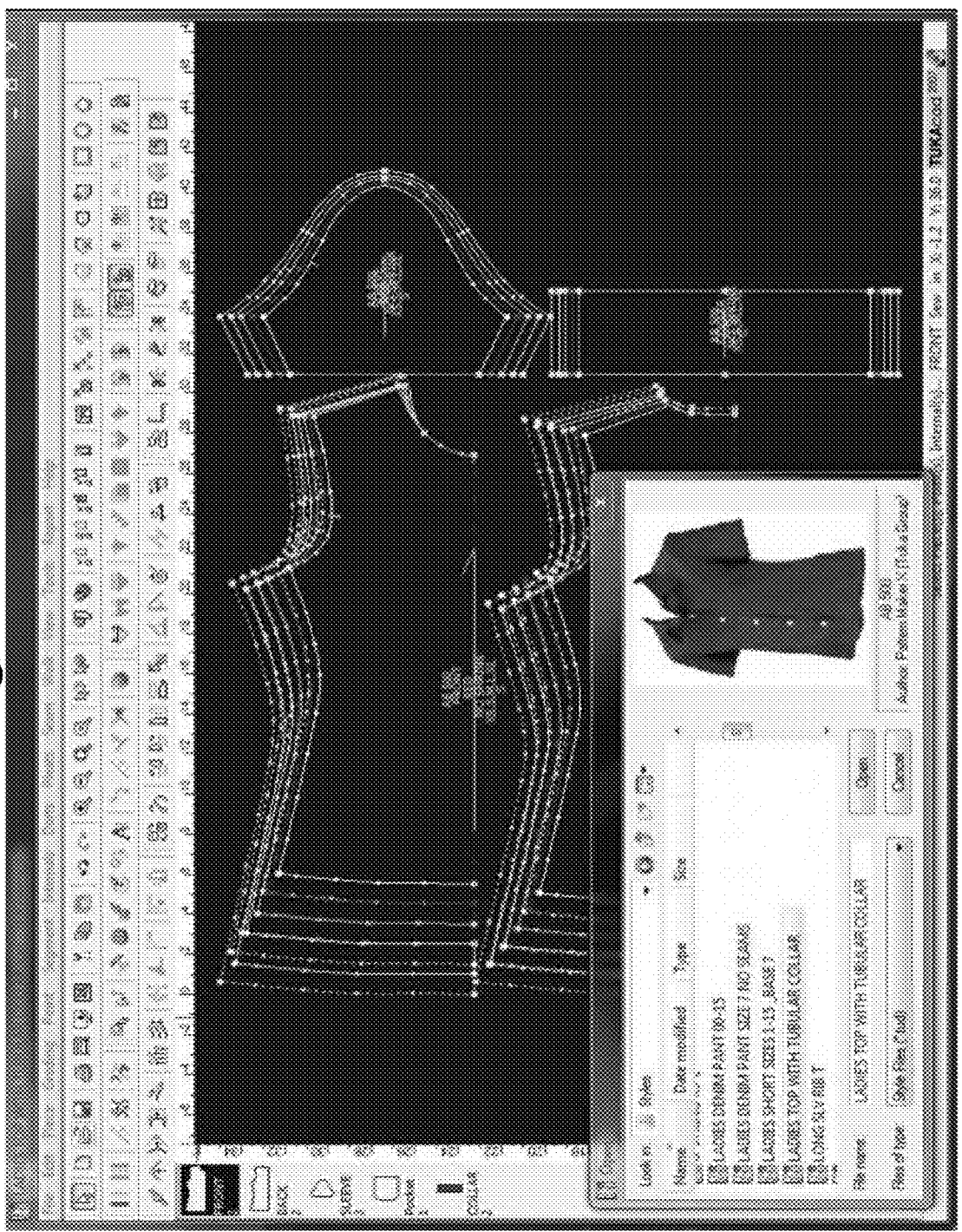
FIG. 7 is a sample screenshot of a digital pattern for a garment according to one embodiment.

With reference to FIG. 6, a flow diagram illustrates a general view of high level method steps performed by one embodiment. Step 300 refers to the data gathering and processing that occurs in 3D virtual apparel processing system 112. Product development information received from retailer system 50 may include data from stereophotogrammetry system 150. In another embodiment, system 112 and stereophotogrammetry system 150 may be a part of retailer system 50. In yet another embodiment, system 112 may be a part of ASP 100, but stereophotogrammetry system 150 may be part of a third party network and vice versa. Furthermore, system 112 and stereophotogrammetry system 150 may not be a part of ASP 100 or system 50, but rather a third party system. In one embodiment, 3D virtual apparel processing system 112 comprises one or more apparel product development workstations 116 with apparel product development software 114, and external hardware devices such as digitizer 118, fabric scanner 120, fabric testing equipment 122, and the like. Retailer System 50 can represent either a retailer, or several companies within the apparel retail and manufacturing supply chain. Moreover, retailer System 50 may contain any portion, combination of subsystems, or entire systems of system 112, 150, and 100. For example, retailer system 50 may have fabric scanner 120 located therein. Stereophotogrammetry system 150 may be used to scan fit model physical body 151, which refers to a physical fit model commonly used apparel product development. The scan data is used to create fit model avatar object 173 using avatar processing system 160. Alternatively, the retailer may only provide measurements of the fit model 151, in which case, those measurements are used in fit model avatar processing system 160 to create fit model avatar object 173. The process of creating fit model avatar object 173 may be similar to the process of creating consumer avatar object 171 described below. The stereophotogrammetry system 150 may be located either independently at a third party location, at retailer system 50, with ASP 100. Further information provided by a retailer may include digital pattern 57, paper pattern 51, fabric and print swatches 56, grading rules 53, fit-model scan data and/or body measurements 58, and production sample garment 59. With reference to FIG. 7, a sample screenshot of a digital pattern 57 is shown.

In another embodiment, some retailers 50 may not have access to some of the information described above. For example, the retailer may not have any information on the pattern other than the technical pack 54, in which case a production sample garment 59 and technical pack 54 will be used by the 3D virtual apparel processing system 112. In another example, the retailer 50 may not provide a technical pack 54, in which case the production sample garment 59 is used for processing as described below.

In any case, whether a pattern, and/or technical pack 54 is received electronically from the producer's digital garment data storage 52, or the less sophisticated garment information 60 is received, the information is processed into 3D virtual apparel processing system 112, and stored in a first data storage 110. In one embodiment, if the digital pattern 57 is received, it is imported into apparel product development software 114, and, if necessary, converted into the proper format. In another embodiment, if the patterns are not digital, they are digitized using a digitizer known to those skilled in the art. In another embodiment, if no pattern is received, then the pattern is made from the production sample garment 59 and/or technical pack 54. Further, fabric swatches, or the production sample garment 59 received are/is tested using the fabric testing equipment 122 to produce an initial set of fabric presets, which are tested as described below to produce a final set of presets.

Creating 3D Virtual Apparel

Figure 8:
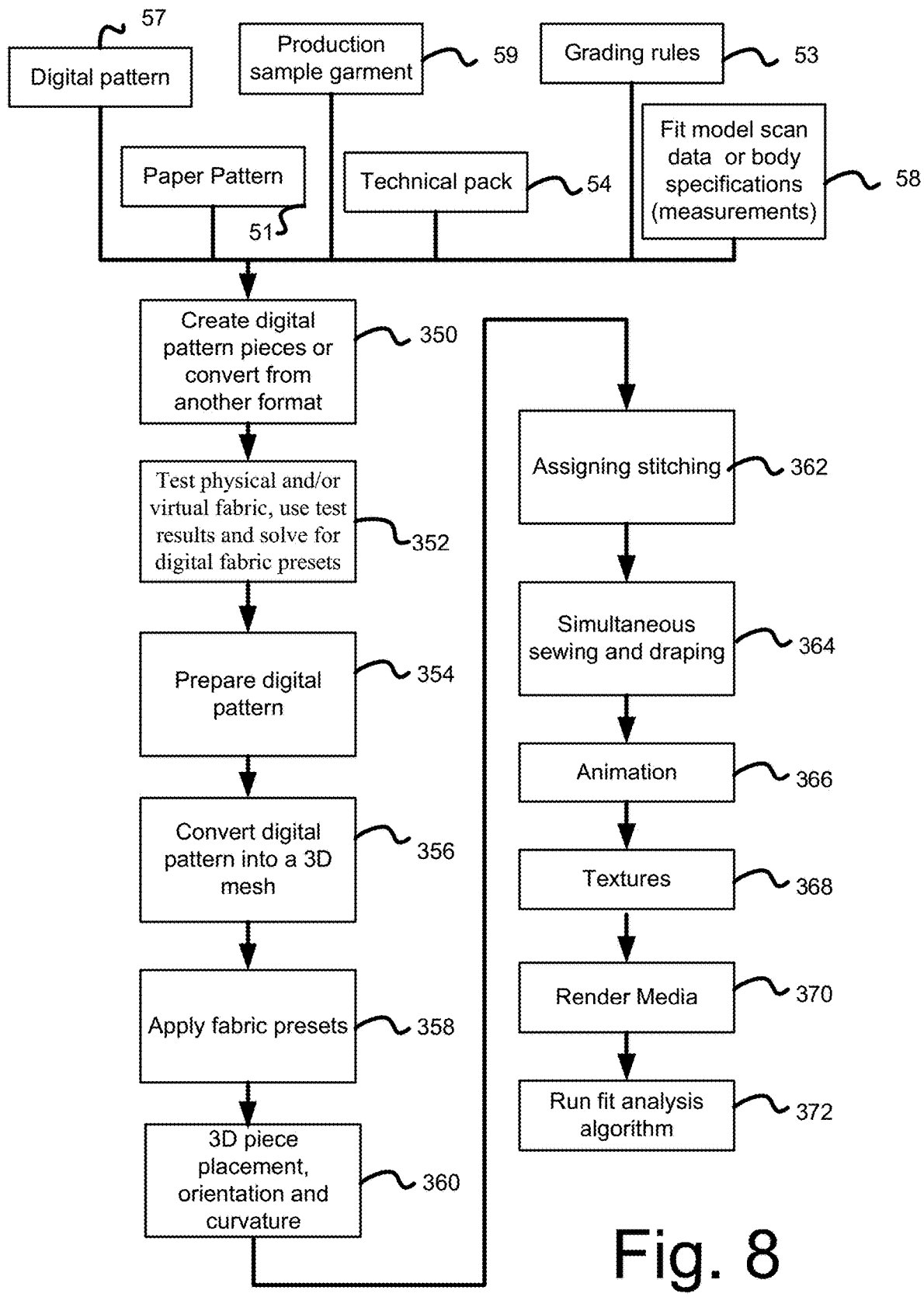
FIG. 8 is a flow diagram illustrating steps performed in creating a 3D virtual garment according to one embodiment.

With reference to FIG. 8, a flow diagram illustrating steps performed in creating 3D virtual garment object 183 is shown according to one embodiment. Any entity may practice one portion, or all of the steps of any or all the methods described herein. For example, and not by way of limitation, it is more likely in some embodiments that clothing manufactures or retailers 50 would provide specifications for the apparel that may or may not include a digital or paper pattern. Further, in one embodiment, the process of creating 3D virtual garment 183 may be performed once per garment and, and not repeated for example, irrespective of the number of times a consumer virtually tries-on the style or the number of consumers that try-on the garment.

In step 350, from the digital pattern 57, production sample garment 59, technical pack 54, grading rules 53, fit model scan data or body measurements 58, and/or paper pattern 51 received from the retailer 50, digital pattern pieces are created, or converted from digital pattern 57, using the apparel product development software 114. Generally, a pattern refers to the collection of the individual pieces of the garment 59. In standard practice, the pattern pieces are drafted first, then laid over fabric, which is then cut around the perimeter of each piece. The resulting pieces of fabric are then sewn together to form the finished garment 59. Therefore, the pattern refers to a blueprint of the garment 49 and its individual pieces.

Indeed, there are several cases in which a digital pattern 57 is received, made, or modified from the above-referenced information received from the retailer 50. In one embodiment, part of the apparel product development software 114 may include a software program named TUKACAD running on product development workstation 116 in the 3D virtual apparel processing system 112, which may be used to create or reformat the digital pattern. TUKACAD is widely used CAD software for digital pattern making, digitizing, grading, and marker making in the apparel industry, and is available from TUKATech, Inc., 5527 E. Slauson Ave., Los Angeles, Calif. 90040, www.tukatech.com. TUKACAD creates points and interpolates splines between points to create a 2D shape or CAD drawing. Additionally, the digital pattern can be graded in TUKACAD to create larger or smaller sizes. Those skilled in the art would recognize that a variety of CAD software programs may be used to perform the functions carried out by TUKACAD.

As noted above, there are several cases regarding the kind of information that is received from a retailer 50 regarding a production sample garment 59 from which the digital pattern pieces are created in TUKACAD. In a first case, a retailer 50 does not have digital pattern 57 or paper pattern 51 for a production sample garment 59. Retailers 50 that do not have patterns 57 or 51 may provide or utilize a widely used technical pack 54 with specifications for how the style is to be made and/or may provide or use a production sample garment 59 for reference. These instructions are then interpreted in 3D virtual apparel processing system 112 to create a digital pattern.

In a likely second case the customer has paper pattern 51 for corresponding to production sample garment 59. Paper pattern 51 may then be digitized or scanned into TUKACAD software using digitizer or pattern scanner 118. As the paper pattern 51 is being digitized, TUKACAD software draws the pattern in digital form resulting in a digital pattern made of digital pattern pieces.

In a likely third case, the retailer 50 has a digital pattern 57 in a third-party format. The digital pattern may then be converted into the format that can be read by the apparel product development software 114 using built-in conversion tools in TUKACAD Software.

In step 352, generally, the physical fabric of a new garment may be tested and simulated to solve for digital fabric presets to be input into apparel product development software 114 for processing. In order to more precisely simulate the behaviour of fabric in a virtual environment, various intrinsic characteristics or parameters that uniquely define real fabric may be determined. The results of those tests may be the fabric presets, which may be entered into a computer model. In some cases, the fabric presets are not independent variables and further testing may be used to arrive at the final fabric presets. In one embodiment, the computer model comprises a three dimensional (3D) virtual software environment.

In one embodiment, software named E-FIT SIMULATOR, also called E-FIT herein, is used as the computer model. E-FIT SIMULATOR is commercially available from TUKAtech, Inc., 5527 E. Slauson Ave., Los Angeles, Calif. 90040, www.tukatech.com, and is built using 3DS MAX's SDK. E-FIT, in one embodiment, incorporates cloth simulation plug-in software, CLOTHFX, which is manufactured by Size 8 Software, and is readily available from TurboSquid, Inc., 643 Magazine St., Suite 405, New Orleans, La. 70130, www.turbosquid.com. E-FIT may be used in conjunction with the aforementioned CLOTHFX software to create 3D virtual apparel, including draping on a virtual model and simulating animation in a 3D environment as described below. This combination of software is currently used commonly by designers and engineers for rapid prototyping of apparel design and development.

Generally, some presets are determined by conducting physical tests on one or more swatches of the fabric from production sample garment 59, while other presets also require an additional virtual test, wherein results from the physical test are compared with results from the virtual test in a process of linear regression, which is used to arrive at the final preset value. For example, there may be three fabric presets for stretch-one for warp, one for weft, and one for shear, which may comprise dependent variables that may not be individually solved-for in an isolated test, but rather may require linear regression using all three parameters to find the final presets.

One of the presets tested comprises stretch and shear resistance. An intrinsic property of cloth or fabric is its ability to stretch, which distinguishes it from a normal rigid body. Fabrics can vary in their ability to stretch, and this characteristic can be quantified. In the physical test of the fabric for this characteristic, the fabric assurance by simple testing (FAST) method known to those skilled in the art may be used. Specifically, the known FAST-3 fabric extensibility test may be used. Procedurally, a first sub-test is performed by hanging a swatch vertically. A weight is attached to the swatch, and the change in length due to the force of gravity is measured. The dimension of the swatch that may be tested is typically 15 cm by 15 cm. The direction selected along which to hang the swatch may depend on the direction of the grain-line of the fabric. That direction is typically known as the warp direction. In one embodiment, the test may be performed in the vertical direction (where vertical denotes the direction of gravity) for three specific orientations of the fabric. Those orientations are the directions of warp, weft, and bias. Weft is the direction perpendicular to warp. Bias is the direction that is 45 degrees from the warp and weft directions. The first measurement may be taken in the warp direction. The length of the swatch in the vertical may be, for example, 15 cm, and a weight of, for example, 100 grams may be attached along the bottom of the swatch, and a new length measurement is taken and recorded. The process is repeated for the weft direction. Finally, in the bias direction, the parameter being measured is called shear. For woven fabrics, measurements in the shear direction may also be made using an additional method, similar to the known KES-FB1 tensile/shear testing. For knits, the process may be the same as described above.

A virtual test for stretch and shear is next conducted. Generally, for virtual tests, E-FIT creates a 3D mesh object for the swatch under test, made in the dimension and shape of cloth, which CLOTHFX simulates gravity, collision with itself, and collision with other objects (or itself), to behave in accordance with how physical cloth would behave in a real environment. Therefore, CLOTHFX as applied to a 3D mesh object is accomplished using a set of algorithms based on known computer cloth simulation theory. The CLOTHFX algorithms are based on modelling the 3D mesh object's vertices as having mass, and the connections between vertices as springs. In other embodiments, alternative algorithms based on known research can be used to model the mesh as interacting particles. In either case, widely known algorithms in classical dynamics may be used to find the time-varying displacement of each point in the mesh. Such solutions have constants (such as natural frequency, spring constant, mass, etc.) which can be adjusted such that the mesh behaves like any particular fabric. Therefore, before draping, constants which appropriately model the selected fabric are chosen. These constants would be the fabric presets discussed herein. Additional forces that may be modelled may include damping forces, which simulate the effect of friction and air resistance. In the cases of friction and air resistance, the fabric presets found are the coefficient of kinetic friction, coefficient of static friction, and drag coefficient, respectively.

The cloth simulation algorithms used in E-FIT and CLOTHFX are thoroughly described in, for example: Xavier Provot, Deformation Constraints In A mass-Spring-model To Describe Rigid Cloth Behavior, Wayne A. Davis and Przemyslaw Prusinkiewicz, editors, Graphics Interface, pp. 147-154, Canadian Human-Computer Communications Society, 1995; Pascal Volino, Nadia Magnenat-Thalmann, Comparing Efficiency Of Integration Methods For Cloth Simulation, Computer Graphics International, pp. 265-272, July 2001; Kwang-Jin Choi, Hyeong-Seok Ko, Stable But Responsive Cloth, ACM Transactions on Graphics, 21(3), pp. 604-611, July 2002, D. E. Breen, D. H. House, M. J. Wozny. Predicting The Drape Of Woven Cloth Using Interacting Particles. In Computer Graphics (Proceedings of SIGGRAPH 94), Computer Graphics Proceedings, Annual Conference Series, pp. 365-372, Orlando (Florida), July 1994; D. Baraff and A. P. Witkin, Large Steps In Cloth Simulation, Computer Graphics (Proceedings of SIGGRAPH 98), Computer Graphics Proceedings, Annual Conference Series, pp. 43-54, Orlando, Fla., July 1998; and Rony Goldenthal, David Harmon, Raanan Fattal, Michel Bercovier, Eitan Grinspun, Efficient Simulation Of Inextensible Cloth, ACM SIGGRAPH 2007 papers, Aug. 5-9, 2007, San Diego, Calif.

In the vertical test, E-FIT and CLOTHFX may create a 3D mesh of the same dimensions of the physical swatch, then hang it vertically, and attach a virtual weight digitally. CLOTHFX is used to apply cloth simulation algorithms to the 3D mesh. Under the force of gravity, the 3D mesh (now behaving as cloth) is deformed or stretched, and the resultant change in length is measured. The simulation occurs using default values found in the physical tests described above for the stretch/shear resistance preset in all three directions. CLOTHFX applies cloth simulation algorithms to the 3D mesh. In order for CLOTHFX to more precisely model a 3D mesh to behave as a particular fabric, regression analysis is used to solve for the presets by repeating virtual tests and adjusting the presets until the results of the physical and virtual tests match.

Another parameter may comprise bend resistance. This measurement involves the way that fabrics differ from rigid bodies in their ability to bend. The resistance to bend is measured with this parameter. In one embodiment, a physical test uses a known method for assessment of the drape of fabrics. A circular swatch, for example, around 15 cm in diameter, may be draped over a circular rigid body, with a smaller diameter than the swatch, which is propped up by a stand. The setup is situated under a light, such that the resultant folds cast a shadow. This is called a projection of the drape. The projection is then photographed, and the surface area of the projected surface is calculated.

A virtual test for bend resistance may be conducted in similar fashion to the physical test. However, instead of measuring the surface area of the projected image (or shadow from the bends), the mesh is flattened within E-FIT. The resultant area of the flattened mesh may be measured and compared with the surface area measured in the physical test. Using regression analysis, the fabric preset for bend resistance may then be adjusted, and the virtual test may be repeated until the surface areas of both tests match, wherein the resultant fabric preset is the final fabric preset for bend resistance.

Yet two other presets may be kinetic and static friction. Fabric draped on a body can experience damping forces that result from friction with the body's surface and friction with itself or with other fabric. A physical test for static friction may be performed by sliding a swatch along a surface, with a known coefficient of static friction. The plane is tilted to find the angle, herein known as the repose angle, at which the swatch begins to slide. The repose angle is used to determine the coefficient of static friction, where the coefficient of static friction equals the tangent of the repose angle for an object sliding down a plane. The coefficient of static friction that results from the physical test may be used as the fabric preset, and no further calculation may be required. Therefore, this value is a direct input into CLOTHFX.

In a physical test for kinetic friction, a method is used in which a constant force is applied to a swatch along a plane to measure the value of the applied force at which the swatch travels at constant velocity. In one embodiment, a string is attached to the swatch, which is pulled along a plane with a known coefficient of kinetic friction. The pull force applied is measured using off-the-shelf instruments for measuring force. The pull force that results in a constant velocity of the swatch along the plane is multiplied by the cosine of the vertical angle of the string used to pull the swatch with respect to the plane. Then, the coefficient of kinetic friction is equal to the force applied multiplied by the cosine of the angle from the plane and then divided by the normal force. The coefficient of kinetic friction may be used as the fabric preset and no further calculation may be required. Therefore, this value may be a direct input into CLOTHFX.

Yet another preset parameter is the surface density of the cloth. A swatch of cloth of the same dimensions can have very different weights, depending on the type of textile used to build the cloth and the density of threads used to weave or knit. In the surface density test, the weight of the cloth is measured. In a physical test, a standard scale is used to measure the weight of a swatch. The weight is divided by the surface area of the swatch to arrive at the surface density. The physical test may be a direct input into CLOTHFX as a fabric preset.

Another preset parameter may be air resistance. Cloth will drape differently depending on the how it falls through a fluid, such as air, and how it reacts with air as it moves in space. When airflow is directed at a cloth, some fraction of the air molecules that make up the airflow will permeate or penetrate the cloth, and some will collide, transferring momentum to the cloth and causing it to move (drag force). The resistance to this drag can vary between fabrics.

In a physical test for air resistance, since the resistance to drag is dependent on the coefficient of drag, and the coefficient of drag will be unique from fabric to fabric, the coefficient of drag is measured. One or more values for the air resistance presets provided by CLOTHFX may be used. However, those skilled in the art would recognize that other well-known tests to measure air resistance could be used to determine such presents for air resistance.

After completing the tests to obtain a final set of fabric presets, the fabric presets 181 may become part of a library of virtual fabrics in the first data storage 110, to be applied when creating virtual apparel made of specific fabric, removing the need to re-test the fabric with new garments made of the same material.

The next step, step 354, comprises preparing digital pattern 180 of the production sample garment 59, either by converting digital pattern 57 from another format, digitizing or scanning paper pattern 51, or creating it using information contained in technical pack 54 Digital pattern 180 may be represented in TUKACAD file format located in data storage 110. TUKACAD's file format stores the digital pattern as a collection of points and hermite splines that are interpolated between points. Each point has an attribute that can govern the shape and/or interpolation of the connected hermite splines. Other types of CAD software may use alternative types of splines or interpolation methods, however since all digital patterns can be converted into TUKACAD's format, all methods for creating and storing data points in a pattern are supported.

In one embodiment, digital pattern 180 may be made for each particular style in a base size. A base size refers to a sample size of a garment, or size that is used as a standard for a particular garment. Larger and smaller sizes may then be created differentially from this sample size by modifying the digital pattern 180, using a process called grading. The amounts that each point in the pattern are to be moved outward or inward are contained in grading rules 53.

The next step refers to converting the two dimensional pattern pieces into 3D meshes. Once the digital pattern has been prepared, it may be modified with construction information useful for conversion of the 2D pattern into a 3D virtual garment 183. Pattern pieces may need to be adjusted to reduce the complexity of some garment features (e.g., removing extra folds, creating finished pieces for pockets, plackets, etc.). Some values used for physical garment production that are not required for virtual apparel also need to be removed (e.g., fabric shrinkage, sewing allowances, etc.). All of these procedures are made to digital pattern 180 in the TUKACAD software contained in apparel product development software 114. To further explain, the following procedures may or may not be applied to one, more, or all of the pieces of a garment depending on the garment type.

1) First, the digital pattern 180 piece quantity may be adjusted. A few pieces that may otherwise be necessary for production become irrelevant for 3D virtual apparel, and may be removed from the digital pattern 180.

2) Second, sewing allowances may be removed from digital pattern 180. A sewing allowance is an extension of the perimeter of a piece that adds additional fabric necessary for physically sewing a garment. This allowance is not necessary for 3D virtual apparel and may be removed from digital pattern 180.

3) Third, any shrinkage allowance may be removed from digital pattern 180. Digital pattern pieces are often created slightly larger in anticipation that once the fabric is washed, the garment will shrink back to the appropriate dimension. Simulation of shrinkage may not be necessary, and therefore, any allowances for shrinkage in the digital pattern 180 may be removed.

4) Fourth, variable hem lines may be removed from digital pattern 180. Primarily used in men's pants, extra fabric is added to the bottom of the pant leg such that a tailor can adjust the hem line. This additional fabric is not necessary for 3D virtual apparel and may be removed from digital pattern 180.

5) Fifth, sewing lines may be added (for pockets, flaps, etc) to digital pattern 180. When a piece needs to be sewn to the inside of another piece, a drill hole may be placed in a physical garment piece. However, in the process of creating digital pattern 180, a sewing line may be drawn digitally to facilitate adding of pockets, flaps, and other features to 3D virtual garment 183.

6) Sixth, a fabric code may be assigned to each piece of the digital pattern 180. For example, the piece that refers to the front of a t-shirt may be assigned fabric code by the name of cotton, whereas the piece that represents the lining of the t-shirt may be given fabric code that represents an elastic material type, such as some polyester spandex blend.

7) Seventh, stitch segments may be assigned in the digital pattern 180. Segments may be defined so that they can be sewn in E-FIT. Marks may be added to the digital pattern 180 to define the starting and ending point of the segments that will be sewn.

8) Eighth, a size may be selected for the fit model avatar 173 (which was created from scan data or measure data from step 58). If digital pattern 180 has been graded into several sizes, the base size may be selected to fit the fit model avatar 173.

9) Ninth, fold lines may be assigned in digital pattern 180. Pieces that are folded (e.g., lapels) may have a line drawn on them where the fold will occur, so that E-FIT can fold the pattern piece along that line.

10) Tenth, pattern pieces may be rotated in digital pattern 180. E-FIT may use the orientation of the pattern pieces as a starting point for making transformations to the 3D mesh. Arranging the digital pattern pieces into a set orientation may ease this process.

11) Eleventh, unnecessary folds may be removed from digital pattern 180. Some pattern pieces may be folded multiple times during the physical construction of the garment. Often, this is not necessary in 3D virtual apparel, and the digital pattern pieces are adjusted to remove this extra length or width from digital pattern 180.

12) Twelfth, internal lines may be adjusted in digital pattern 180. Because the 2D spline pattern pieces are eventually meshed for 3D software, some adjustment of the splines may be necessary to avoid errors in E-FIT. For instance, a line cannot be meshed. So if there is an internal pattern line that extends past the outer boundary of the pattern piece, that external part of the line may need to be removed from digital pattern 180.

The next step 356 may be to convert the digital pattern into a 3D mesh. A 3D mesh, or polygon mesh, is a collection of vertices, edges and faces that defines the shape of a polyhedral object in computer graphics. The mesh is a collection of several closed surfaces. In a mathematical vector algebraic sense, which may be important for calculations, a mesh is a collection of numbers organized into several matrices. More simply stated in a geometric description, a mesh is made of points that are joined together with segments and surfaced by polygons.

In step 356, the digital pattern 180 may now be imported into E-FIT. The CLOTHFX plug-in in E-FIT may convert the pattern pieces into 3D mesh objects. Essentially, the 2D splines are surfaced to create a 3D mesh. The digital pattern 180 is now a 3D mesh. The 3D mesh is then further defined to have components such as pieces and segments, which later get defined with additional attributes.

In step 358, E-FIT interprets the fabric code for each piece of digital pattern 180 and assigns the corresponding fabric presets. For example, the piece of digital pattern 180 that represents front of a t-shirt may have been assigned a material code for cotton. E-FIT interprets this code and retrieves the fabric presets for cotton from its fabric library of presets.

In step 360, E-FIT may apply 3D piece placement, orientation, and curvature in the 3D pattern.

In step 362, E-FIT assigns sewing instructions. In this step, E-FIT matches each particular segment of a 3D mesh corresponding to a particular piece to another segment on the same 3D mesh, or to another 3D piece, in accordance with how the garment is supposed to be sewn together.

Figure 9:
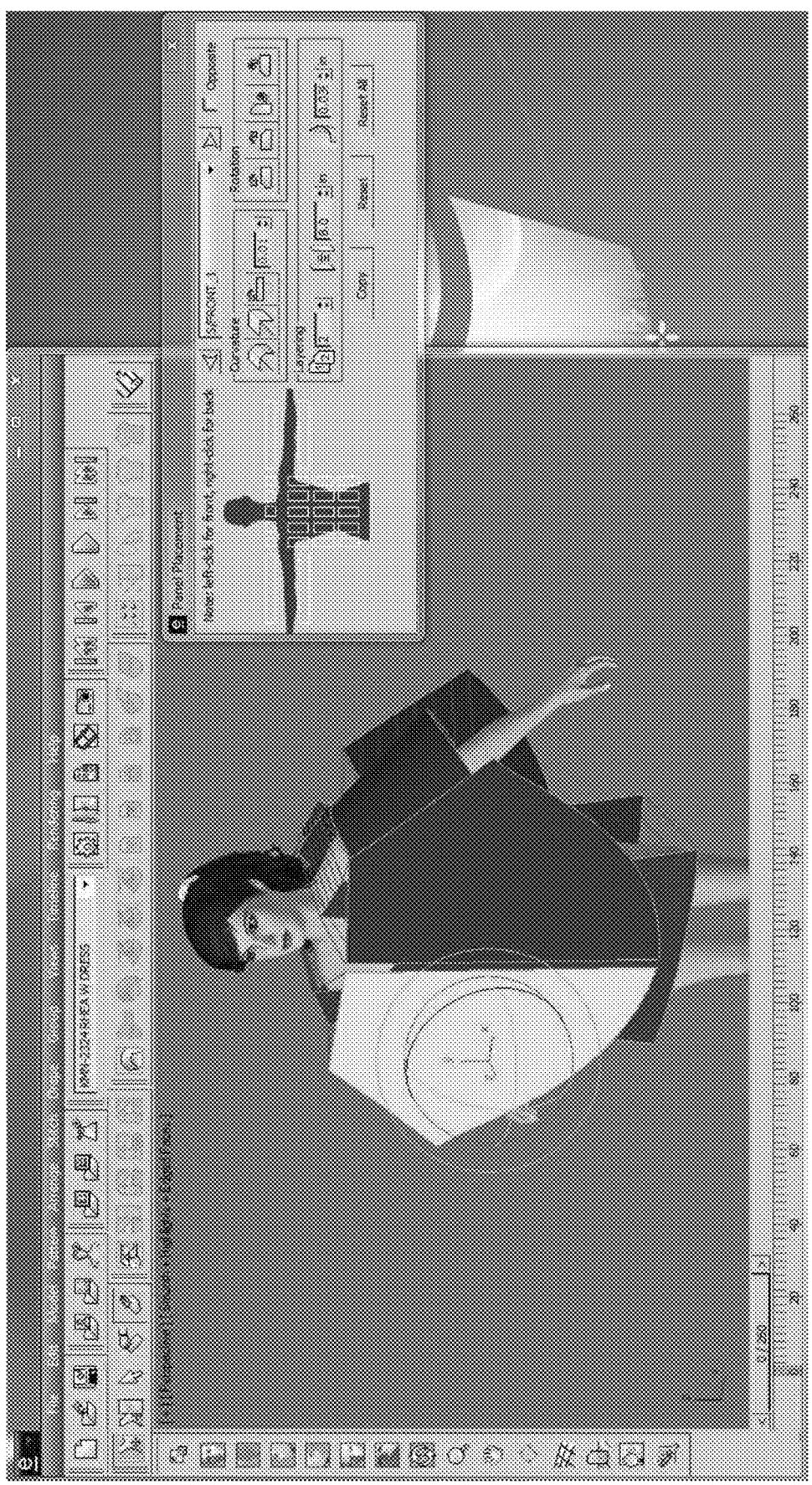
FIG. 9 is a diagram illustrating an exemplary 3D piece placement and matching of segments of a virtual garment according to one embodiment.

Referring to FIG. 9, a diagram illustrates an exemplary 3D piece placement and matching of the segments using E-FIT.

With reference back to FIG. 8, in step 364, E-FIT may virtually sew and drape the 3D mesh on the fit model avatar 173. Fit model avatar 173 is a virtual representation of the actual physical fit model, wherein the exact body measurements 164 may have been measured and used to create a virtual body in the base/sample size, or the physical fit model has been scanned, and the scanned data is used to create fit model avatar 173 in the base/sample size. If fit model avatar 173 is created from scanning a physical fit model, the scanning process may be similar the process described below with respect to an avatar.

Sewing and draping may be completed using functions provided by CLOTHFX and native E-FIT according to the sewing instructions assigned above. Often, garments have lining and/or layers of material. In such cases, layers may be placed, stitched, and draped in a specific order. The culmination of the simulation results in a drape on fit model avatar 173 that may be identical to the drape of a real garment on a real fit model.

Figure 10:
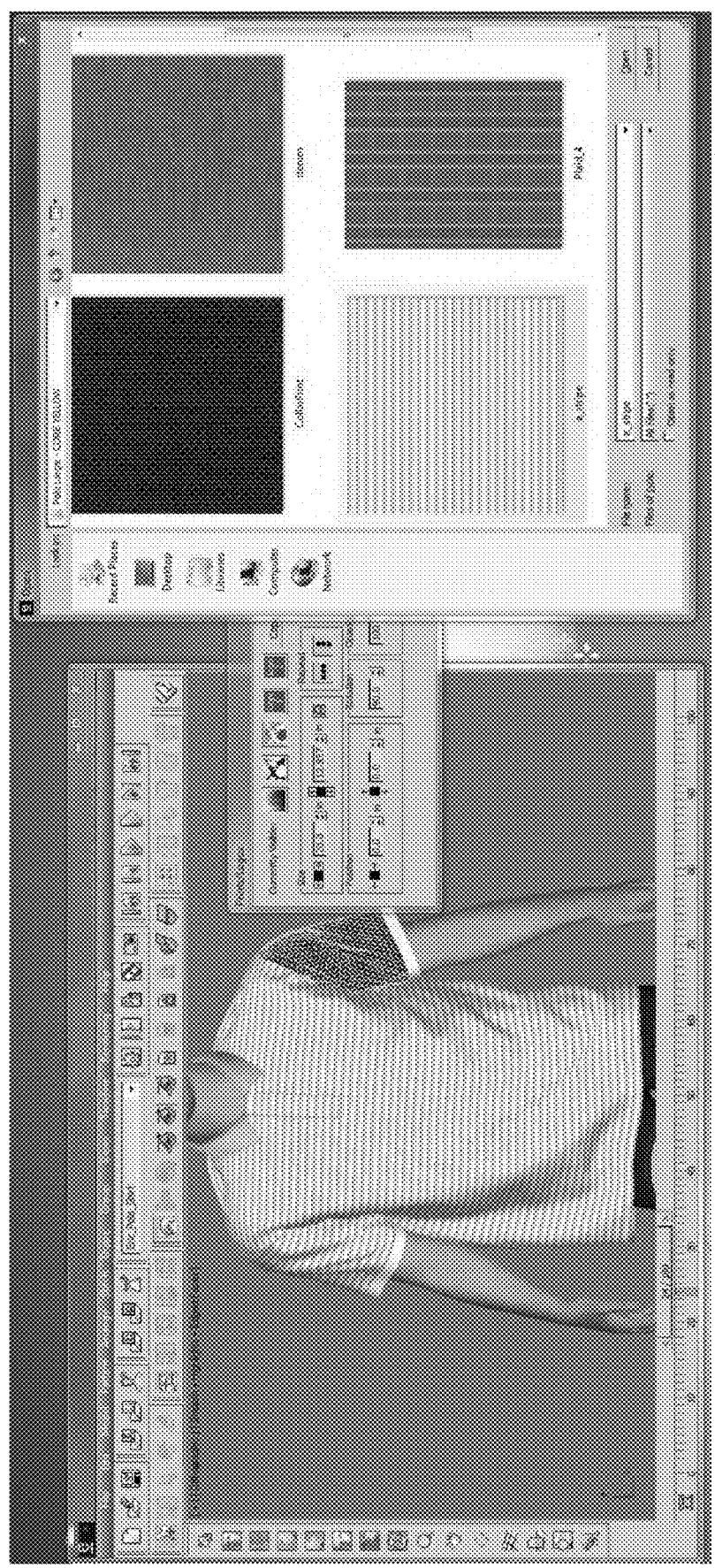
FIG. 10 is a screenshot from the virtual sewing and draping process for a virtual garment according to one embodiment.

With reference to FIG. 10, a screenshot 2050 using CLOTHFX and native E-FIT is shown during the sewing and draping process according to one embodiment.

With reference back to FIG. 8, in step 366, animation is created for the 3D virtual garment 183. Fit model avatar 173 may have a predetermined motion or animation already applied. The predetermined motion may simply be a series of frames wherein the position of the fit model avatar 173 is slightly different, and when played out appears to be walking. Then, to simulate animation of the garment being worn, the above-described sewing and draping is performed for each frame. In one embodiment, thirty frames is equivalent to one second of animation.

In step 368 a presentation may be created for the retailer 50 to be approved and later presented to consumer 20. Making an object in 3D appear like physical object may often involve duplicating the look not only in 3D software or interactive rendering software, but require visual output hardware (such as a monitor or display) to accurately replicate the appearance of the object in reference to a real object.

E-FIT may apply a texture. In one embodiment, the 3DS MAX is used as the 3D engine for E-FIT. Since 3DS MAX refers to "textures" as "material textures," the term "textures" will be referred to as such herein. However, it is understood by those skilled in the art, that the term "texture" is used for an embodiment that does not include using 3DS MAX, but rather some other 3D software, such as PHOTO-SHOP available from Adobe Systems Incorporated, 345 Park Avenue, San Jose, Calif. 95110-2704. A material texture 188 contains data that may be assigned to the surface or faces of a 3D mesh so that it appears a certain way when rendered. Material textures 188 affect the color, glossiness, opacity, and the like, of the surface of a 3D mesh.

However, these material textures 188 may not be photometric, in the sense that they may not simulate the interaction of light or photons with the material textures 188 accurately. A user may use E-FIT's material editor built-in functions to further create the illusion of the garment's appearance. More specifically, the user of E-FIT may work to simulate the correct appearance of material textures by adjusting and applying various material texture properties or texture maps that model the color, roughness, light reflection, opacity, and other visual characteristics.

In one embodiment, material textures 188 may be applied to the surface of each 3D mesh corresponding to each pattern piece. These material textures 188 realistically simulate various attributes that make up the appearance of production sample garment 59. The following list of attributes may be modelled:

a. color:
  combination of ambient, diffuse, specular, and/or filter
b. roughness or bumpiness:
  bump maps, or displacement maps
c. light reflection:
  shiny, glossy, matte, etc which are accomplished using general shader settings or maps.
d. opacity.

Certain attributes may be set by the retailer. For example, a retailer may send a color swatch with a specific red-green-blue (RGB) value or PANTONE color value. In instances where the appearance is dependent on the lighting conditions, the attributes may be adjusted at the retailer's discretion.

Prints, images, logos, and other maps can be adjusted in size, position and orientation. The retailer may provide information (included in technical pack 54) on the placement (position) and size of these maps. Using E-FIT, a user loads these maps and adjusts them accordingly. Furthermore, stitch textures, a component of material texture 188, are added to give the appearance of actual stitching threads.

Completing the above steps results in the completion of 3D virtual garment 183 and fit model drape 186, which are then stored in data storage 110.

Figure 11:
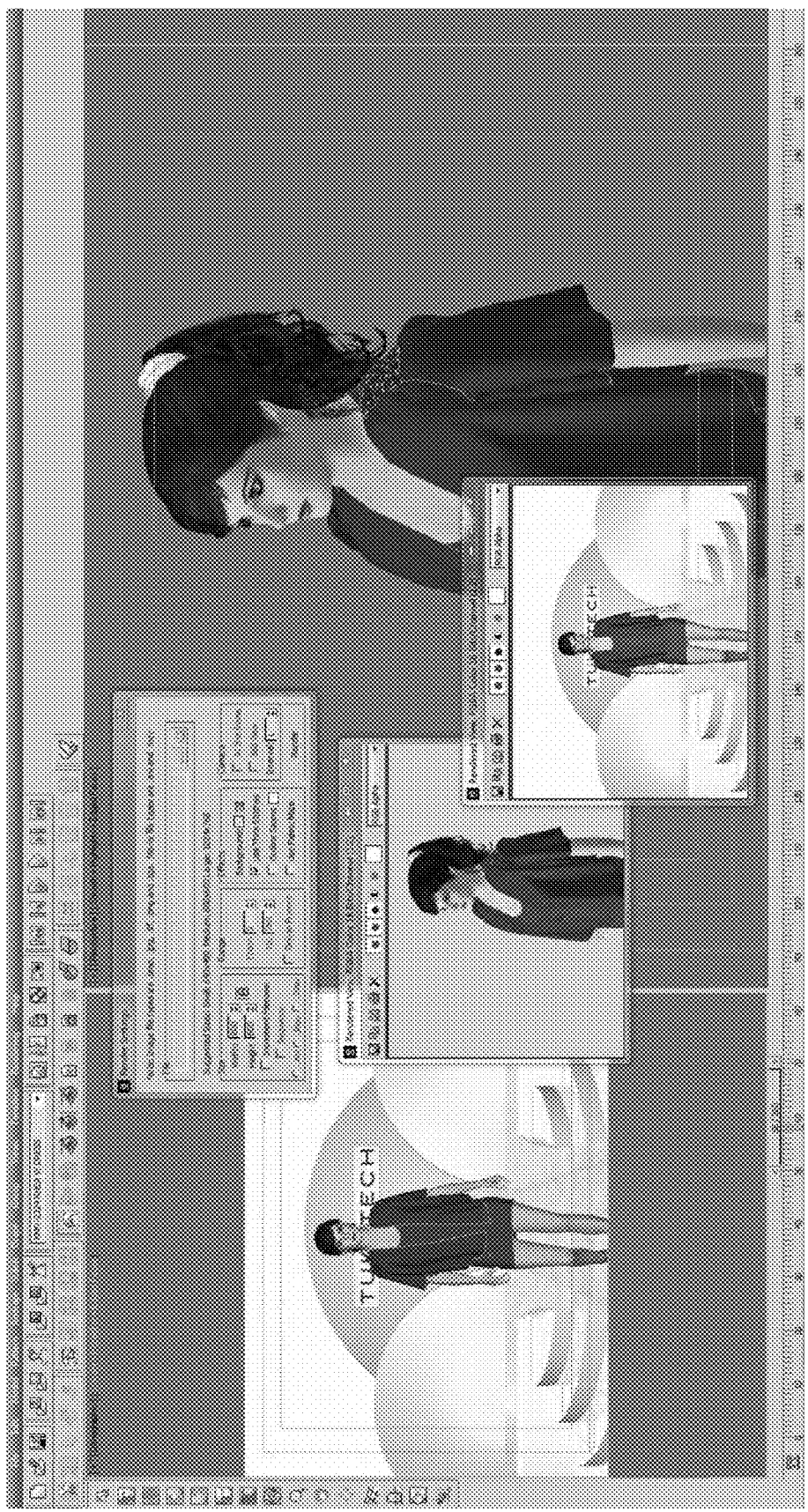
FIG. 11 is an example of a rendering of a drape of a virtual garment according to one embodiment.

Additionally, in step 370, media, such as images, movies, may be rendered and stored as original sample rendered media 182. Additionally, original sample 3D viewer data 187 may be created. FIG. 11 is an example of such rendering using E-FIT.

With reference back to FIG. 8, in step 372, a fit analysis process may be executed which results in creating original sample fit data 18.

Creating Avatars

The previous discussion, in section "3D Virtual Apparel", has been focused on the "3D Virtual Try-On", a process of draping the existing 3D virtual apparel garment on a consumer avatar is described. Since both processes require the use of an avatar, the following section describes processes to create an avatar, whether the avatar is for a fit model or a consumer.

An avatar may be defined as a 3D mesh constructed to have a similar shape as the consumer body 22 or fit model body 151 it was intended to model, and may or may not be animated. Fit-model avatar 173 may be created to drape 3D virtual garment 183 on the avatar to produce fit model drape 186, by way of system 112. Likewise, consumer avatar object 171 may be used for simulating the drape of production sample garment 59 on a consumer's body 22, resulting in consumer drape 1102. The methods for any avatar, whether it be creating consumer avatar 171 or fit model avatar 173, are interchangeable and are described below.

In one embodiment, consumer avatar 171 or fit-model avatar 173 can be generated using three types of procedures, all of which are well-known to one skilled in the art. The first procedure utilizes a technique in which one mesh is conformed to another. The second procedure utilizes a technique called morphing, where one mesh is morphed to another. A third technique involves manually moving vertices from a mesh to another location, which is often called digital 3D sculpting. With respect to creating an avatar, these techniques involve moving vertices from one position to another. However, the conforming and morphing methods are discussed in more detail herein. These two techniques may have disadvantages and advantages over each other and therefore are used in varying situations. Described next is one embodiment of using each of these techniques. However, any technique not discussed, but well known to those skilled in the art could theoretically be used.

An avatar is created using avatar software application 904, which may be contained in avatar processing system 160. Avatar software application 904 begins creating an avatar by first accepting some input data on the consumer or fit-model. There may be many categories of input data, relating to any type of information on a human being or population of human beings—e.g., demographic information. For example, one may have data on the distribution of fat on the human body. Another example is data describing the amount of heat energy emanating from a body. A third example may be the color of the skin, eyes, and hair, and a fourth example may be data on the shape of the body. Since there are many types of information that can describe a human being, it is worthwhile to categorize the information or data. In one embodiment, the following three categories of data may be used to create an avatar: (1) body shape data, (2) body appearance/cosmetic data, and (3) body function data, where body may be defined to include all or any parts of the body, and data may be qualitative and/or quantitative, and stored in any form or format. For example, but not by way of limitation, the term body may include the torso, head, face, hands, fingers, finger nails, skin, hair, organs, bones, etc, or it may only include the torso.

Body shape data, refers to data that can be used or interpreted to understand and reproduce the accurate shape of a human body subject. Body appearance/cosmetic data, refers to data that helps reproduce the appearance of a human subject (e.g. eye color, hair style, skin texture). Body function data provides information on how the human subject's body functions. In (e.g. the systems of the body, such as lymphatic, endocrine, skeletal, immune, and others). It may aid to have body function data on movement (e.g. how the body's limbs, torso, head, or skeletal, muscular, etc respond to movement). Such data, for example, and not by way of limitation, may be captured using a generic motion capture technology for capturing body movement data. Finally, each data category may have many different types data in which information relating to that category are stored. The various data types for each data category are described below.

Beginning with the first category of data, body shape data, there may be three data types in which information on the shape of a human subject can be stored, provided, or retrieved for use in creating an avatar. For example, but not by way of limitation, the input data may be one or the following: (1) raw body scan data 172, (2) body measurements and other shape data 176 and (3) photographs 174. Although photographs can also be a raw body scan data type, photographs taken in some other mechanism, (e.g. webcam or single camera) may also be included.

Raw body scan data 172 refers to raw output data from any type of scanner, whether it be generic body scanner 149 (e.g. point cloud originating from RF data, structured light data, lasers, mirrors, or any other type of raw data output from these scanners or other yet undiscovered types of scanners). Moreover, raw body scan data can originate from stereophotogrammetry body scanner 152

Body measurements and other shape data 176 may refer to both manual measurements taken of consumer body 22 either by the consumer or by a third-party, extracted body measurements from raw scan data 172, statistically derived measurements from sizing survey data 178 or avatar statistical data 179, and/or any combination thereof.

Photographs 174 refer to supplemental photographs of the body from different angles, which may or may not include the other parts of the body (e.g. face, hands, etc). For example a user may take a photograph of the face of consumer body 22, and submit the photograph online, by which the system may map the person's face to consumer avatar object 171. Photographs 174 may not originate from a scanner, but rather may originate from a web cam, a single digital camera and may be user submitted. Photographs 174 shall not be confused with photographs originating from raw body scan data 172, especially in the case of the method of stereophotogrammetry as described below.

When creating an avatar, the highest precision in reproducing the shape, appearance and function may be desired, however, where precision in data is lacking, a combination of data types may be used to help supplement data or data precision that may be lacking. Therefore, in one embodiment, a combination of data types may be used to further increase the precision of the avatar.

For example, but not by way of limitation, one may use the following combination of data types for accurately reproducing the body shape of a human subject. These data types could include size survey data. Sizing survey data 178 refers to body measurement and shape data from a population of human beings. For example, but no by way of limitation, the widely used Size USA survey, provided by TC2, which contains raw scan data or extracted body measurements from over 10,000 people can be used. Such data may represent one or many populations with various demographic characteristics. Then, this data may be searchable or queried by a specific demographic or set of demographics. Then, additional information collected on the consumer or fit model such as, age, ethnicity, sex, residence, etc may be used to match the consumer to a specific population that is represented in sizing survey data. If a consumer is matched to a specific population, using demographic data in user data 177, then the body measurements or other shape data for that population may be used in part or in entirety to create the avatar of the consumer or fit model. In yet another embodiment, once a sufficient collection of consumer avatars 171 is gathered, statistics on body measurements and shape can gathered and stored as avatar statistical data 179 and may be used for statistical interpretation and later mined for trends that can further be used to constrain other estimates of the shape of the body, or further enhance those estimates.

Once information, of any data type, regarding the three data categories discussed above, is gathered, the next step is to interpret the data and create an avatar. However, in order to create an avatar, it may be useful to first create one or many base avatars 158. Base avatar 158 is a template avatar from which all other avatars can be made. Depending on the data type for the body shape category of data, the base avatar 158 can be morphed or conformed into the shape of consumer body 22 or fit model body 151

Figure 12:
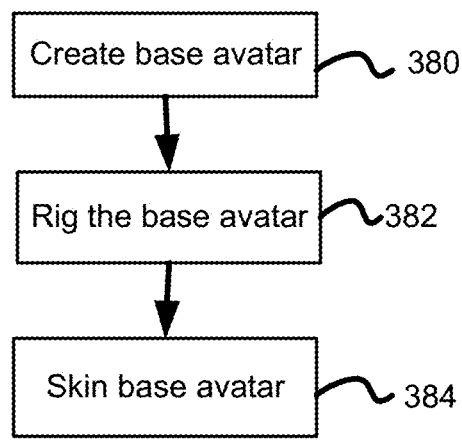
FIG. 12 is a flow diagram illustrating the steps for creating a base avatar according to one embodiment.

With reference to FIG. 12, a flow diagram illustrating the steps for creating a base avatar 158 according to one embodiment is shown. In step 380, a base avatar 158 may be created using avatar software application 904 in avatar processing system 160. In one embodiment, avatar software application 904 may comprise of built-in tools available in 3DS MAX or any 3D software that allows a user to create, edit and store mesh objects. Using 3DS MAX, a 3D artist may sculpt the arms, legs, torso, and other body parts. Then a 3D artist may join all the body parts together to form a single mesh of the base avatar 158.

In step 382, the base avatar 158 is rigged. A bone structure (or biped) may be inserted into the mesh using 3DS MAX tools, and may be sized and scaled appropriately so that the bone structure fits within the mesh properly. This process is known to those skilled in the art as rigging.

In step 384, within 3DS MAX, the bone structure may be attached to the vertices on base avatar 158 mesh so that when the bones move, base avatar 158 will move in accordance with how a human body typically moves. This process is known to those skilled in the art as skinning, and is not to be confused with putting skin on, which falls into the category of texturing. A file that holds the skinning data may be saved in avatar processing system 160 in avatar data storage 170.

Base avatars 158 can be created for male and females for any typical sample size (i.e., men's size 40, women's size 8, etc.). From these base avatars 158 made from sample sizes, new avatars can be made in any size and shape.

As discussed earlier, the use of the conforming or morphing techniques is dependent on the type of data received on consumer body 22 or fit model body 151. If the data type is raw scan data 172, then a mesh is created from the raw scan data, and the base avatar 158's mesh is conformed to it. In another embodiment, the received data type may be body measurements and other shape data 176. In such a case, the morphing technique may be used. In this case, the base avatar 158 mesh is morphed. The following discussion relates to the case where the data type is raw scan data 172.

Generally, in the prior art, consumer avatar 171, and fit model avatar 173 would be created by measuring the shape of a consumer's body, or a physical fit-model described above, by way of a set of measuring tools, such as lasers, cameras, structured light, radio waves, or other electromagnetic based tools. Such configurations of measurement are typically called direct or passive body scanners, and will be collectively referred to as body scanners herein. In one embodiment, stereophotogrammetry system 150 may comprise any of these prior-art types of body scanning technologies, or alternatively, stereophotogrammetry system 150 may include stereophotogrammetry body scan booth 152 described below. Stereophotogrammetry system 150 may also comprise any body scanning software for processing raw scan data to create 3D meshes or avatars. Alternatively, stereophotogrammetry system 150 may include body scanning software 154 described below. For example, companies that produce some of these types of prior art scanners include those available from Unique, 133 Troop Avenue, Dartmouth, NS, B3B 2A7, Canada, TC²/Imagetwin, located at 5651 Dillard Dr., Cary, N.C. 27518, Telmat Industrie, 6, rue de l'Industrie—B. P. 130—Soultz, 68503 GUEB-WILLER Cedex (France), and, or Human Solutions, GmbH, Europaallee 10, 67657 Kaiserslautern, Germany.

However, in one embodiment of the presently described system, stereophotogrammetry may be applied. Photogrammetry is the practice of determining the geometric properties of objects from photographic images. In the simplest example, the distance between two points that lie on a plane parallel to the photographic image plane can be determined by measuring their distance on the image, if the scale of the image is known.

A more sophisticated technique, called stereophotogrammetry, involves estimating the three-dimensional coordinates of points on an object. These are determined by measurements made in two or more photographic images taken from different positions. Common points are identified on each image. A line of sight (or ray) can be constructed from the camera location to the point on the object. It is the intersection of these rays (triangulation) that determines the three-dimensional location of the point. More sophisticated algorithms can exploit other information about the scene that is known a priori, for example symmetries, in some cases allowing reconstructions of 3D coordinates from only one camera position.

Algorithms for photogrammetry typically express the problem as that of minimizing the sum of the squares of a set of errors. This minimization is known as bundle adjustment and is often performed using the Levenberg-Marquardt algorithm.

Figure 13:
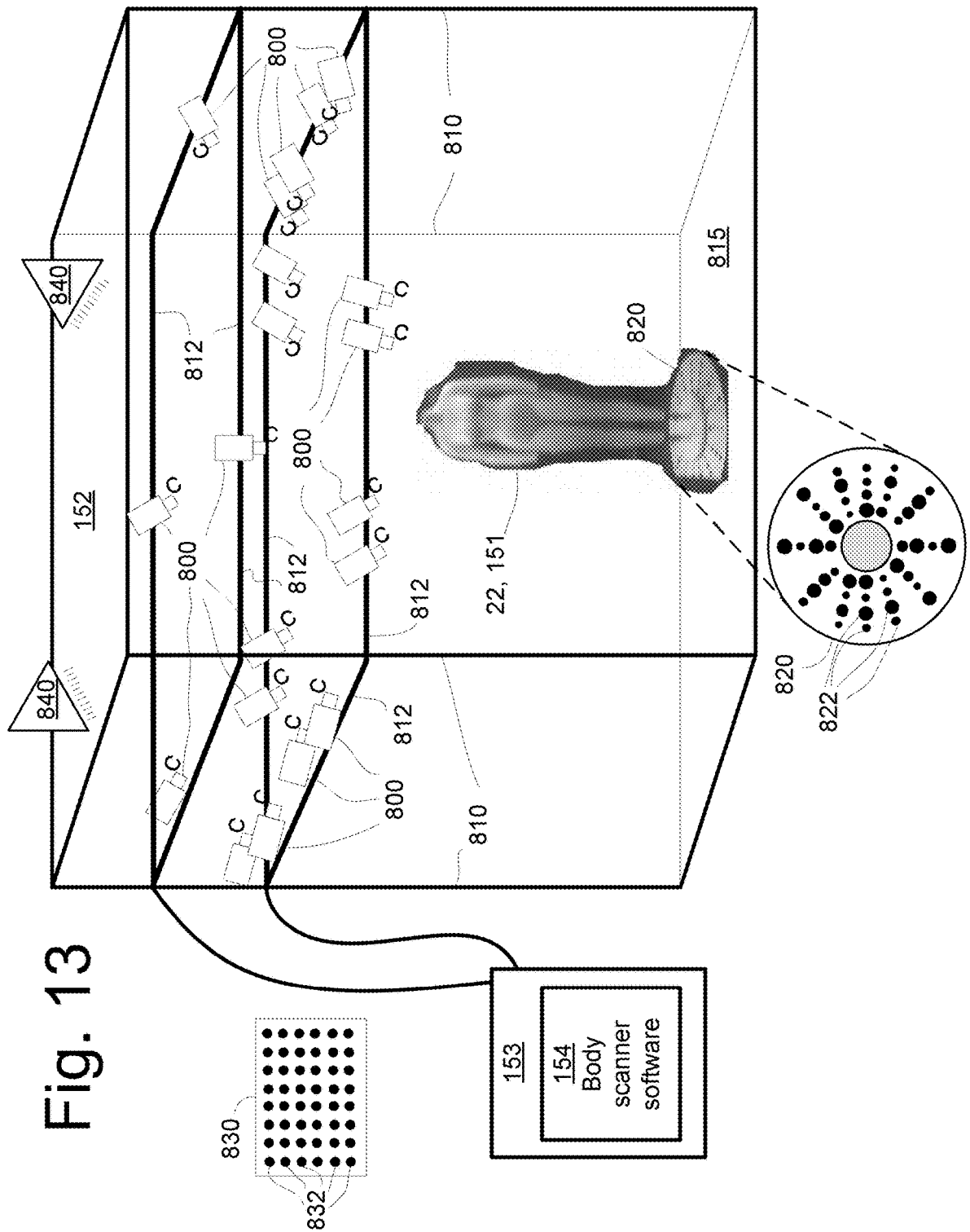
FIG. 13 is a diagrammatic right perspective view of a stereophotogrammetry body scan booth and a scan booth computing device containing body scanning software according to one embodiment.

The stereophotogrammetry method may have advantages in cost and features that other methods cannot achieve. With reference to FIG. 13, a diagrammatic right perspective view of a stereophotogrammetry body scan booth 152, and scan booth computing device 153 with body scanning software 154, is shown according to one embodiment. Briefly, using stereophotogrammetry, several cameras 800, for example twenty, may be positioned around the human body, and then simultaneously triggered to acquire multiple digital photographs. The resultant photographs may then be transmitted to scan booth computing device 153, which contains body scanner software 154. In other words, body scanner software 154 may trigger cameras 800 and acquire photographs from cameras 800. The body scanner software 154 may be used to mask and remove background colors, and may further be used proc to implement a process called segmentation to remove object(s) other than the subject of interest. Body scanner software 154 performs many of the previous mentioned steps using a program originally written using MATLAB software, available from Mathworks, Inc., MathWorks, Inc., 3 Apple Hill Drive, Natick, Mass. 01760-2098. However, those skilled in the art would recognize that many different software applications may perform similar functions. For example, the software may be written using the C++ programming language to perform the same functions implemented in the MATLAB software.

Furthermore, the refined photographs are then sent as inputs to 3DSOM PRO software available from About Creative Dimension Software, Ltd., Wey Court West, Union Road, Farnham, Surrey GU9 7PT, United Kingdom. This software then uses these photographs to create 3D mesh 159. However, those skilled in the art would recognize that many different software applications may perform similar functions. 3D mesh 159, is then imported into 3DS MAX, wherein the base avatar 158 is morphed to the dimensions and shape of 3D mesh 159.

Figure 14:
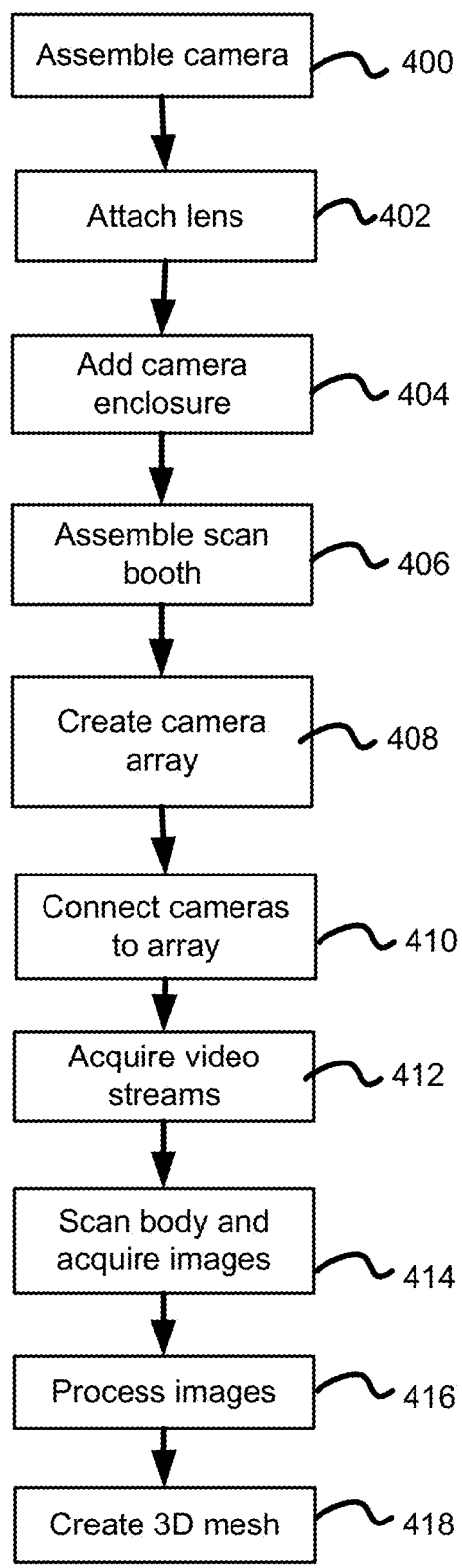
FIG. 14 is a flow diagram illustrating steps performed for scanning consumer body or fit model body using the stereophotogrammetry method of body scanning, as well as steps for converting the output of such body scanning method into a 3D mesh according to one embodiment.

With reference to FIG. 14, a flow diagram illustrates steps performed for scanning consumer body 22 or fit model body 151 using the stereophotogrammetry method of body scanning, as well as the steps for converting the output of this body scanning method into a 3D mesh.

In step 400, the camera 800 is assembled. Any standard charge coupled device (CCD) or complementary metal-oxide-semiconductor (CMOS) camera 800 can be used. In one embodiment, a CMOS 2 megapixel chip is used in order to maximize resolution while minimizing cost, such as that provided in the QUICKCAM 600 available from Logitech, Inc., 6505 Kaiser Dr., Fremont, Calif. 94555 USA. However, any CCD or CMOS commercially available digital camera, webcam, professional camera, industrial camera, or security camera could be used. The aforementioned QUICKCAM 600 has a 2 Megapixel sized CMOS chip providing 30 frames/second over a universal serial bus (USB) 2.0 connection. The camera 800 may be dissembled to retrieve only the circuit board with the CMOS chip attached and USB still connected. However, any megapixel size chip with any frame rate and other connections (e.g., Firewire), could also be used. Moreover, additional cameras could be added, a slightly rotating pedestal could be used, and/or mirrors could be used in place of some cameras. However, the method described herein was selected due to accuracy and cost-effectiveness.

In step 402, a wide angle lens may be attached to a spacer, attached to a camera enclosure, which encloses the circuit board to which the CMOS chip is attached. A wide field-of-view lens may be used in this embodiment so that the camera 800 can be positioned as close to the consumer body 22 or fit model body 151 as possible while keeping the subject within the field of view. Any distortion due to the lens may be corrected-for in 3D SOM PRO software using its lens calibration tools. In one embodiment, a 2.9-8.2 mm lens, provided by Computar, Inc., 55 Mall Drive, Commack, N.Y. 11725, may be used.

In step 404, a plastic project enclosure (for example, 3×2×1 inches), provided by RadioShack, Inc., may be used to house the camera 800. A 3-5 mm hole may then be cut open to make the CMOS chip visible. A 5 mm spacer with threads may be attached over the hole and the lens is screwed into the spacer.

Steps 400-404 may be repeated for each camera to be used.

In step 406, stereophotogrammetry body scan booth 152 is assembled. Standard zero structures 910 may be used to assemble the structure, for example, a 7 ft×7 ft×7 ft sized stereophotogrammetry body scan booth 152. A matte 920 with a specific pattern, which may be provided by 3D SOM, Inc., may be placed in the center of the floor 915. This is where the consumer body 22 or fit model body 151 stands. Cameras 800 and lights may be fixed to cross beams 912 that attach to the four pillars of the structure 910 along the perimeter. Electrical pipe may be built around the structure on the inside and outside of the zero pillars at the very top of the body scanning booth 152. Fabric may be hooked to the pipes to create drapes to enclose the structure from outside light, and to include a fixed color background behind the subject from all angles. Pre-fabricated structures could be used in a similar manner, where modifications may be made depending on the type of structure.

Referring again to FIG. 14, in step 408, the camera array may be created. 20-50 cameras 800 may be positioned along the walls of the stereophotogrammetry body scan booth 152. At least fifteen cameras 800 may be positioned at approximately eye level and distributed equally around the consumer body 22 or fit model body 151. However, any configuration could be used. At least an additional four cameras may be positioned at two feet higher than eye-level and distributed around consumer body 22 or fit model body 151. The last camera 800 may be positioned in an aerial view above the head of consumer body 22 or fit model body 151. The positioning of the all 20-50 cameras can vary depending on the user's choice, and is not limited to this configuration. In one embodiment, the matte and the entire subject may be visible in the field of view in all configurations, so as to take advantage of the features of 3D SOM PRO Software.

In step 410, the cameras 800 are connected in an array. Cameras 800 may be connected USB powered hubs in one embodiment. All hubs may be connected to a computer with USB ports. In other embodiments, the cameras may be wired for Bluetooth, Ethernet, wifi, or the like.

In one embodiment, stereophotogrammetry body scanning software 154, which may interface with or include software components, may also contain executable instructions to perform one or more of the following steps 412-418 described below. In step 412, the video stream of consumer body 22 or fit model body 151 is acquired. MATLAB software, which may be one of the software components of stereophotogrammetry body scanning software 154, is available from Mathworks, Inc., 3 Apple Hill Drive, Natick, Mass. 01760-2098, and which may be used to read the video streams from the cameras. Specifically, the image acquisition toolbox of MATLAB may be used to start and view all 20 video streams. Those skilled in the art would recognize that a variety of software programs may be used to perform the functions carried out by MATLAB.

In step 414, the images may be acquired from the video stream, wherein the main subject is consumer body 22 or fit model body 151, and may be placed in the middle of the stereophotogrammetry body scan booth 152 to stand on a matte, such that their body is in the field view of the cameras. The cameras are triggered to acquire images or single frames from each camera 800. In one embodiment, a manual trigger may be used with cameras that do not support hardware triggering. However, hardware triggering can be used to speed up image acquisition to prevent any lag time between cameras.

In step 416, MATLAB's image processing toolbox may be used to mask images, save them in any format that can be read by 3D SOM PRO, and send them to 3D SOM PRO Software. Software written using MATLAB may be compiled into a standalone executable file to perform this step.

In step 418, 3D mesh 159 is created using 3D SOM's software.

In one embodiment, the number of cameras 800 may be arbitrary. By way of example, and not by way of limitation, 20 or more, or less, cameras 800 may be used. Further, the position of the cameras 800 may be more or less arbitrary in one embodiment. A position calibration map 820 may be used for helping the 3D SOM PRO software determine the position of the cameras 800 in three dimensional space. In one embodiment, the position calibration map 820 may comprise a flat annular component having radial spaced black circles 822 printed thereon. Depending on the position of each camera 800, the black circles 822 are captured by each camera 800 with a different distortion, which 3D SOM PRO, or other software used to calibration position, is capable of interpreting to indicate the position of each camera 800. In one embodiment, the black circles 822 may preferably be of varying sizes.

Further, any number of various types of cameras 800 or sensors may be used. In one embodiment, webcams may be used because they are less expensive and may provide relatively higher resolution with CMOS sensors at the same price. However, more expensive digital cameras with CCD sensors with a broader color ranges may be used. Further, any type of lens may be used with the cameras 800. For example, the lenses are capable of having various focal lengths. For example, the types of lenses may be defined by variations in focal length, diameter, and/or magnification.

In order to calibrate the cameras for such variations in lens types, for example, a lens calibration map 830 having black circles 832 similar to those on the position calibration map 820 may be used. Each camera 800 may be calibrated for type of lens by pointing each camera at the lens calibration map 830 at a constant distance to and angle, taking pictures at various zooms. The 3D SOM PRO software may then use the varying images captured by each of the cameras 800 and/or lens types. The 3D SOM PRO software then takes the calibration images and correct for the varying cameras 800 and/or lens types.

With the above description of the stereophotogrammetry system 152, those of skill in the art would recognize that the stereophotogrammetry system 152, may comprise an arbitrary number of two or more cameras 800 for taking independent photographs of a physical object; a position calibration map 820 for providing three dimensional position data for the two or more cameras 800; each camera 800 having a lens, wherein each lens has a type, wherein two or more of the lenses are capable of being the same type; a lens calibration map 830 for each type of lens, wherein the lens calibration map is capable of correcting for non-linearity within the lens; a first set of instructions capable of execution on a processor 153 to acquire a set video streams from the two or more cameras 800; a second set of instructions capable of execution on a processor 153 to trigger the two or more cameras 800 substantially simultaneously to produce an image from each camera 800; a third set of instructions capable of execution on a processor 154 to download and save the image from each camera 800; a fourth set of instructions capable of execution on a processor 153 to mask the image from each camera 800 to produce a set of masked images; a fifth set of instructions capable of execution on a processor 153 to process three dimensional positional data from the position calibration for the set of masked images; and a sixth set of instructions capable of execution on a processor 153 to process a three dimensional mesh from the set of one or more masked images. The system 153 may have a variable number of cameras 800. The system 152 may include variable positions of the cameras 800. The position calibration map 820 may be modifiable according the number and position of the cameras 800. Further, the lens calibration map 830 may be modifiable according the types of lenses on the cameras 800. The size of the whole stereophotogrammetry system 154 may also be adjustable. The first, second, third and fourth software instructions may also comprise image acquisition and processing software instructions, which may all be embodied in the body scanner software 154. The image acquisition and processing software instructions may comprise MATLAB software instructions in one embodiment. The image acquisition and processing software instructions may comprise LABVIEW software instructions in another embodiment.

In one embodiment, the download of the images from the cameras 800 may occur using universal serial bus (USB), Firewire or wifi network devices.

The fifth and sixth software instructions may comprise three dimensional modelling software. In one embodiment, the three dimensional modelling software may comprise 3DSOM PRO. In another embodiment, the three dimensional modelling software may comprise compiled object oriented software instructions.

Lights 840 may be a part of the system 152, which may be used to create uniform lighting conditions to create the least amount of shadows. Reflectors may be used to further achieve ambient light conditions within the booth 152. A uniform background may be used within the walls of the booth to aid in the masking process. Those skilled in the art, for example, may find a green background generally aids in the masking process.

Finally, the size of the stereophotogrammetry body scan booth 152 may be variable or adjustable, generally having little effect on the operation of the booth 152. This allows for the booth 152 to be adjusted for use in different special arrangements as space may provide.

Figure 15:
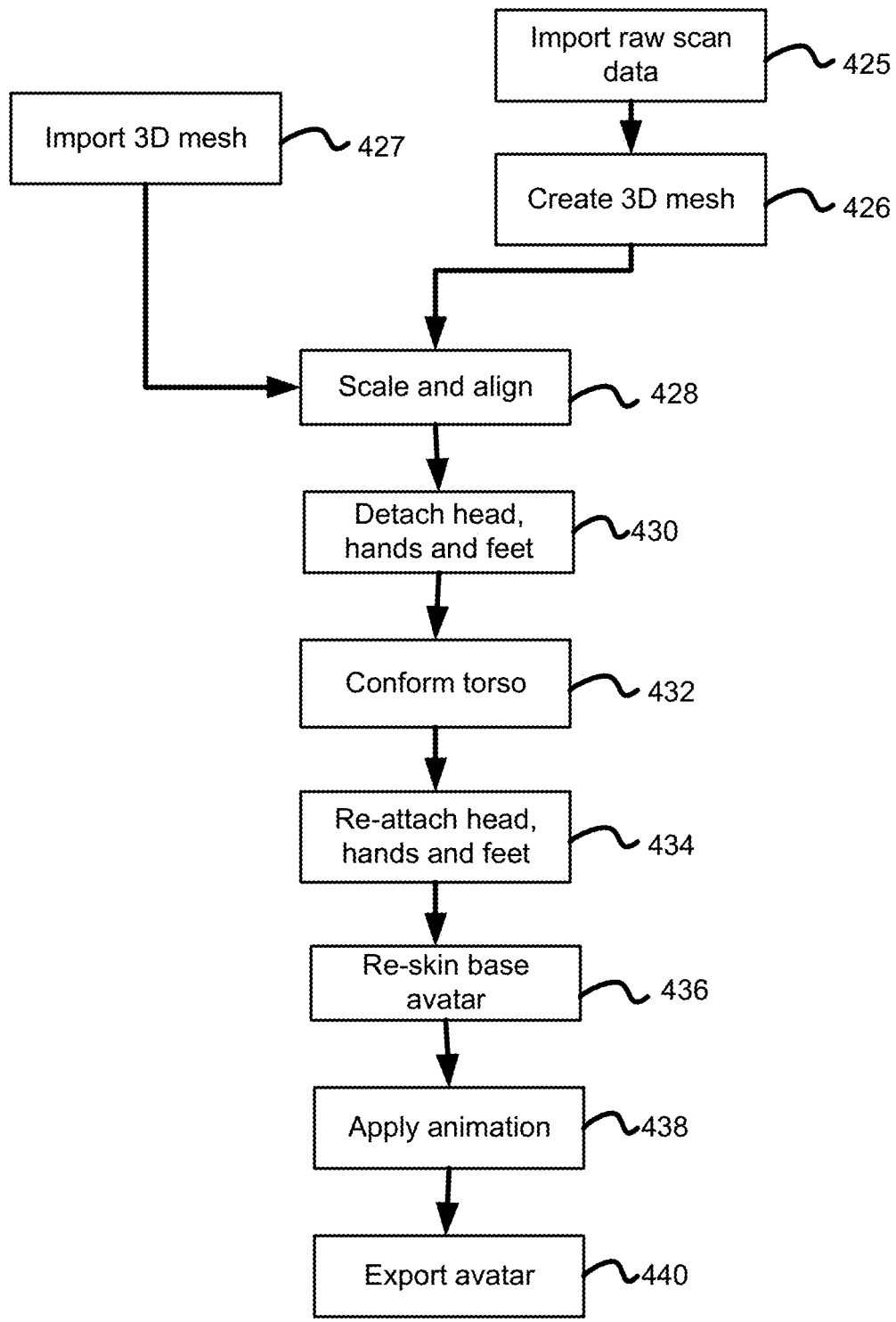
FIG. 15 is a flow diagram illustrating further steps performed by an avatar software application according to one embodiment.

With reference to FIG. 15, a flow diagram illustrates further steps performed by avatar software application 904. In one embodiment, 3D mesh 159, previously created in stereophotogrammetry system 150, may be sent to the avatar software application 904. Then, the initial step performed by avatar software application 904 is step 427, importing the 3D mesh 159.

In another embodiment, a prior art body scanner system 149 may be used in place of stereophotogrammetry system 150, where prior art body scanner 149 may refer to all currently existing forms of body scanners described in prior art, or alternatively all other body scanners contemplated by future technologies. Then, prior art body scanner system 149 may also provide a 3D mesh as an output. In this case, the initial step performed by avatar software application 904 is step 427, similarly importing the 3D mesh 159.

However, in another embodiment, output data from prior-art body scanner 149 may only provide raw scan data as input in step 425, and not a 3D mesh. Thus, in step 426 3D mesh 159 may be created from a prior-art scanner system's 149 raw scan data using MESHLAB software, a widely available open source application available form http://meshlab.sourceforge.net/, 3DS MAX, and/or any 3D software able to perform such function with raw scan data.

In step 426, 3D mesh 159 is imported in to 3DS MAX software.

In step 428, scaling and alignment of 3D mesh 159 with base avatar 158 may take place. Within 3DS MAX, the base avatar 158 may be superimposed on top of the 3D mesh 159. The base avatar 158 may then be scaled in size such that its height aligns with the height of the 3D mesh 159. When scaling up and down, the shape and proportion of the base avatar 158 may not change. In other words, the system grows or shrinks base avatar 158 so that 3D mesh 159 and base avatar 158 occupy a similar volume. Furthermore, the limbs of base avatar 158 may also be adjusted to align with the limbs from 3D mesh 159.

In step 430, the head, hands, and feet are detached from base avatar 158 in order to complete the next step.

In step 432, the torso of base avatar 158 is conformed to the torso of 3D mesh 159. MAXSCRIPT code, which is a scripting language provided by 3DS MAX, may be run, which can run within 3DS MAX. This script moves vertices of the torso of base avatar 158 to the torso of 3D mesh 159, such that their shapes and proportions are the same and they occupy the same volume. In running this script, the skinning may be lost and can be reproduced.

In step 434, the hands, feet and head of base avatar 158 are re-attached to newly conformed mesh.

In step 436, the conformed mesh is re-skinned using saved data stored in avatar data storage 170.

In step 438, animation is applied. This step may be to store a standard point-cache file which stores the animation components of consumer avatar 171 or fit model avatar 173.

If the subject was consumer body 22 then the conformed mesh may be referred to now as consumer avatar 171.

Otherwise, if the subject was fit model body 151 then the conformed mesh may be referred to now as fit model avatar 173.

In step 440, consumer avatar 171 or fit model avatar 173 is exported from 3DS MAX and stored in avatar data storage 170.

In one embodiment, consumer avatar 171 or fit model avatar 173 may be derived directly from body measurements 176 instead of 3D mesh 159, where body measurements and other shape data 176 may have been extracted from raw scan data 172, or from user data 177 (e.g. demographics) using avatar software application 904. Further quantitative information may include data originated from statistical analysis of historical body scans (sizing survey data 178) and/or avatar statistical data 179. If the consumer provides these measurements, they may do so by entering on computing device 24 which then stores the in user data 177. The computing device 24 may comprise any type of processing device, such as a personal computer (desktop or laptop), smartphone, iPHONE®, iPAD®, tablet pc, mobile computing device, kiosk, gaming device, media center (at home or elsewhere), or the like. For example, but not by way of limitation, the consumer may enter body measurements and/or select other avatars features using an html form or a client-side software application 28 running on computer device 24. The user's selection and entered data is then to ASP 100's avatar software application 904 running in avatar processing system 160.

Figure 16:
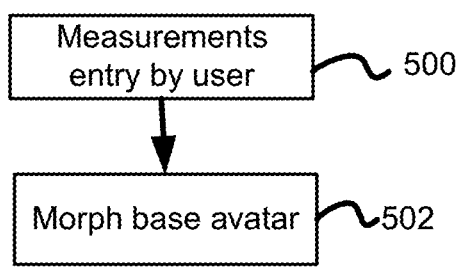
FIG. 16 is a flow chart illustrating steps for creating an avatar according to one embodiment.

With reference to FIG. 16, a flow chart illustrates the steps for creating an avatar from any combination of data entities 176, 177, 178, and 179, according to one embodiment. In step 500, the consumer body measurements and other shape data 176 are gathered. In one embodiment, by way of example, and not by way of limitation, there can be approximately between 5 and 50 points of measurements corresponding to consumer body 22.

Since the data type is body measurements and other shape data, base avatar 158 may be morphed to create the shape of consumer avatar 171 or fit model avatar 173.

One skilled in the art would recognize that in order to morph a mesh, one may require morph targets. Therefore, base avatars 158 may have morph targets, allowing them to be morphed. For extremely large and small human bodies, additional base avatars 158 may created with additional morph targets. A morph (sometimes called a control) is applied to the base avatar 158 that links to the morph target, and can be used to interpolate between the two objects, changing the size/shape of the base object to match the morph target's geometry either partially or completely. In other words, by adjusting the morph target, one can approximate the shape of a new avatar. When several morphs are adjusted such that the new avatar similarly match the consumer body 22's or fit model body 151's body shape and or measurements, then one has arrived at consumer avatar 171 or fit model avatar 173 respectively.

Each morph target may correspond to one or many points of measure. Points of measure are control points for a specific body measurement from body measurements and other shape data 176 (e.g. the circumferential waist measurement may have a control point). Therefore, when the point of measure needs to be changed to a specific body measurement value (given by the user, extracted from raw scan data, or derived by some other means), the morph target is adjusted.

With reference to FIG. 17, a graphic slide show illustrates an exemplary flow of the morphing process described above. For example, in slide 2000, the base avatar 158 is shown in its original shape. As shown in slide 2002, the morph targets are adjusted closer to the consumer measurement data. Finally, in slide 2004, the morph targets are reached, and the consumer avatar 171 is therefore created.

In step 502, base avatar 158 may be morphed as described above.

Another embodiment includes supplementing body measurement 176, user data 177, sizing survey data 178, or avatar statistical data 179 with digital images 174. Digital images 174 from a single camera may further enhance the process of creating consumer avatar 171 or fit model avatar 173. Multiple digital photographs may be used as references for sculpting the mesh of base avatar 158 within avatar software application 904, wherein sculpting refers to the process of adjusting the morph targets to match a visual contour of consumer body 22 or fit model body 151 given in a digital photograph.

Figure 18:
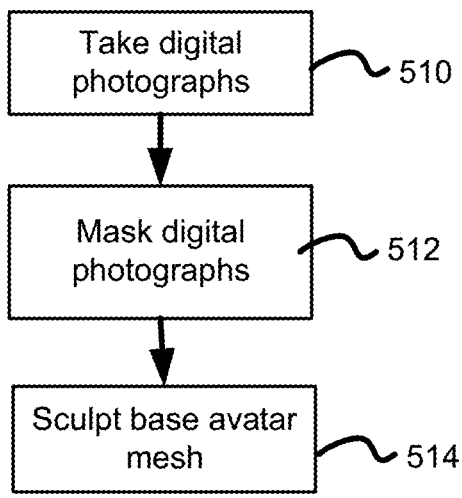
FIG. 18 is a flow diagram illustrating the steps for creating an avatar according to one embodiment.

With reference to FIG. 18, a flow diagram illustrates the steps for creating an avatar according to one embodiment. In step 510, digital photographs can be taken of a consumer body via a webcam or any digital camera. To create an avatar from multiple photographs, at least three photographs may be used (front, back and side), along with a height measurement. The digital photographs may be sent to the avatar software application 904. In step 512, the digital photographs can be masked such that everything besides the consumer body is removed from the image. This can be accomplished using MATLAB software, PHOTOSHOP by Adobe Systems Incorporated, 345 Park Avenue, San Jose, Calif. 95110-2704, or any image editing software.

In step 514, the base avatar mesh is sculpted. The digital photographs may be used as references to match the shape of the avatar to the real person. The photographs may then be mapped to planes in a 3D scene in 3DS MAX and placed around the base avatar's mesh. This makes it possible to use the photographs as references to the shape of the body that is being reproduced digitally. For example, if the photograph is front-facing, then the base avatar's mesh is also front-facing in the scene. Second, the base avatar's morph targets are adjusted to get the shape close to where it should be to match the silhouette of the reference image. Then, vertices in the base avatar's mesh are adjusted using soft selection methods to correct the avatar to match the references, and the measurements. When using photographs as references, photographs of the front, side and back of the body are adjusted digitally to correct errors in the photography as much as possible.

In yet another embodiment, the above methods described with respect to creating a consumer avatar 171 may be mixed, matched, and/or combined. For example, body measurements 176 can be further enhanced by adding images from a single camera of the body and face of consumer body 22 or fit model body 151.

Figure 19:
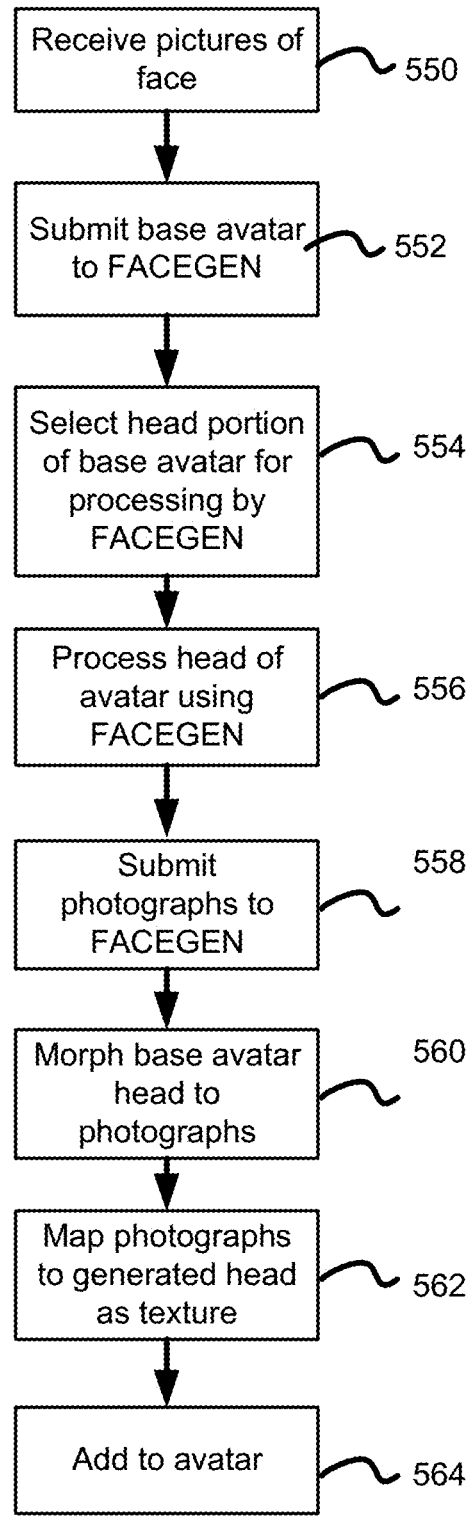
FIG. 19 is a flow diagram illustrating a method for modelling the face of consumer body or fit model body according to one embodiment.

With reference to FIG. 19, a flow diagram illustrates a method for modelling the face of consumer body 22 or fit model body 151. Whichever method described above is used to create consumer avatar 171 or fit model avatar 173, the face of consumer body 22 or fit model body 151 can be modelled using digital photographs from a webcam or digital camera. In step 550, three close-up images of the front profile, left profile, and right profile of the face of consumer body 22 or fit model body 151 may be taken and sent to the avatar software application 904. In step 552, FACEGEN Software, provided by Singular Inversions, 2191 Yong street, suite 3412, Toronto, ON. M4S 3H8, Canada, can be used to create a 3D mesh of the head. In step 554, a 3D mesh of the head can then be added to consumer avatar 171 or fit model avatar 173.

3D Virtual Try-on of Apparel on an Avatar

The next process may include draping the 3D virtual garment 183 on a consumer avatar 171 in an automated process on the web or computing device 24, resulting in consumer drape 1102. The process begins when the consumer chooses to virtually try-on 3D virtual garment 183. The consumer can request to virtually try-on 3D virtual garment 183 by way of a graphical user interface (GUI) on computing device 24, or by sending a request over the internet through a website.

Figure 20:
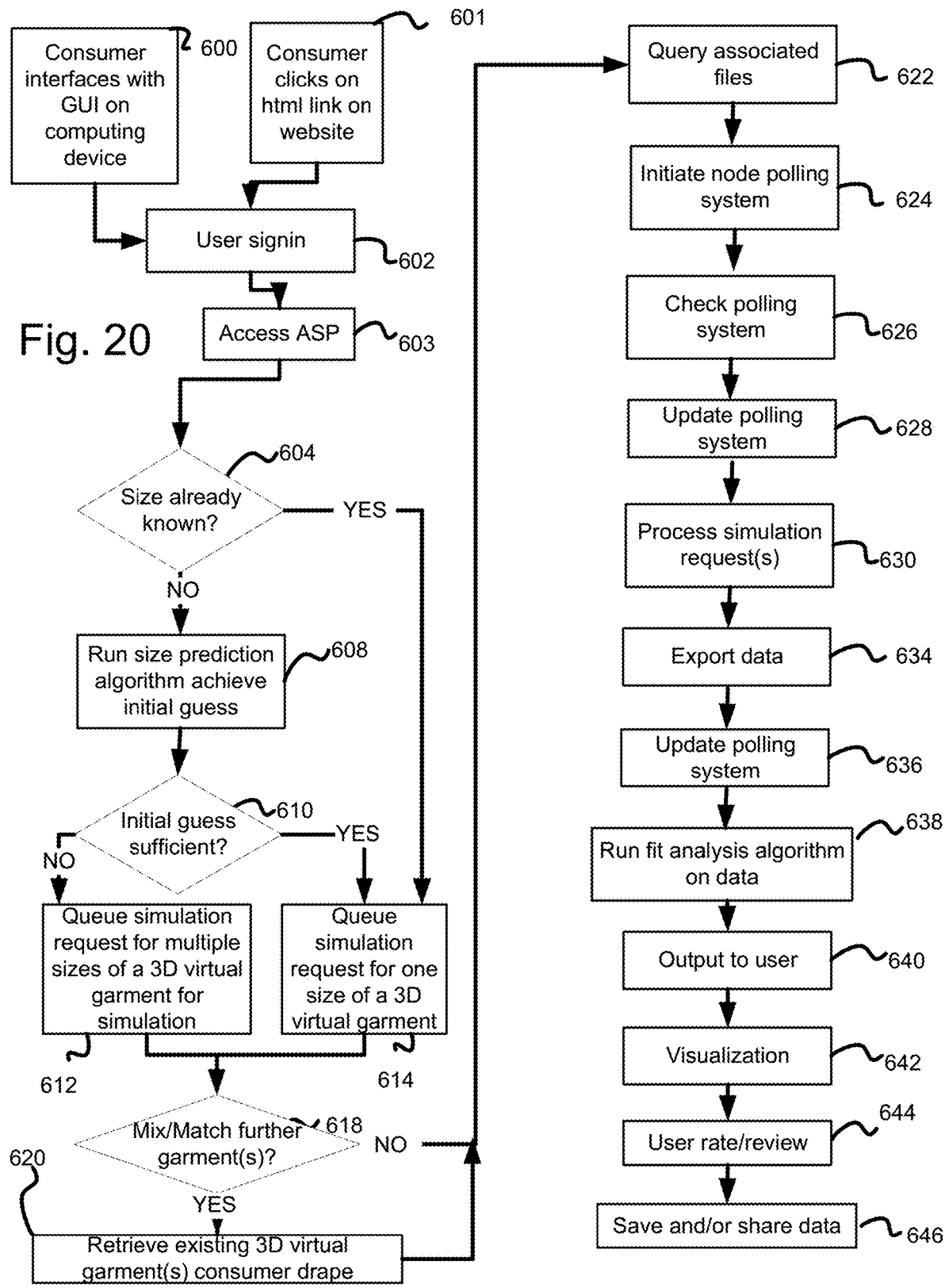
FIG. 20 is a flow chart that describes events that occur when a user decides to try on a virtual garment according to one embodiment.

In one embodiment, the consumer may send a request on the internet to virtually try-on a garment by clicking hyperlink 81 which may reside in retailer's online store 80, a third-party online store, or on an online store running ASP 100. Hyperlink 81 may be positioned next to a display of a 3D virtual garment 183, or a digital representation of production sample garment 59 available for virtual fitting. When a user presses hyperlink 81 using computing device 24, a sequence of events is started. With reference to FIG. 20, a flow chart describes the events that occur when a user decides to try on a virtual garment. In step 601, in this embodiment, the user may select hyperlink 81 or press the button next to 3D virtual garment 183 or a digital representation of production sample garment 59 on a website. The button or hyperlink 81 provides access to application service provider (ASP) 100 in step 602. The ASP 100 may communicate directly with retailer online store 80 or computing device 24 and may run 3D draping software application 900. With each request, data that signifies the user is included. In the asp-model, if the user is not known, then the user is prompted to sign-in or create a user profile with the ASP 100.

In another embodiment, referring to step 600, a user may run 3D draping software application 900 locally on computing device 24 enabling the user to virtually try on garments. This embodiment may require the user to sign in and exchange data with ASP 100 or retailer system 3D draping software application 900 may run computer device 24 or may run online in ASP 100 as an online service for retailers or consumers over a wide area network through a network connection. 3D virtual try-on processing system 1200 may exist at the retailer or may be hosted by a third party web server. In another embodiment, 3D draping software application 900 may run on kiosk 130. The user may click on a link or a button with a mouse, or interact with a touch screen on the display of computer device 131. The user may see the resultant output of the 3D virtual try-on process on 3D viewer application 132.

In step 604, it is determined whether the appropriate size for the consumer has already been determined. If so, processing moves to step 614. Otherwise, processing moves to step 608, to conduct size prediction algorithm 908.

In step 608, consumer's body measurements and other shape data 176 are queried from avatar processing system 160 and compared against 3D virtual garment measurements 184 of 3D virtual garment 183 at corresponding points of measure. The root mean square (rms) of the deviations of these two sets of measurements (body measurements 176 vs. 3D virtual garment measurements 184) is calculated for each size available for production sample garment 59. Ease added to digital pattern 180, may be added to the shape of the avatar to better assist in attaining a solution.

In step 610, it is determined whether the size that results in the lowest rms is sufficient for an initial guess. Those skilled in the art of statistical analysis may use chi-squared or other statistical tests to assess the strength of the initial guess which may depend on the accuracy of which the consumer avatar 161 accurately duplicates the size, shape and proportion of consumer body 22. Moreover the user may determine if the initial guess is sufficient. If it is determined that the size is sufficient to serve as the initial guess for draping, then processing moves to step 614 wherein the initial guess of the 3D virtual garment 183 is queued for draping on the consumer avatar 161. Otherwise, processing moves to step 612 wherein multiple sizes of 3D virtual garment 183 are queued for draping on the consumer avatar 161.

In both steps 612 and 614, queue simulation request(s) is/are performed. Once received, simulation requests are sent to a queue system 903 that is capable of maintaining lists of multiple simulation requests from multiple users.

It is also possible that the user may want to virtual try-on one garment with one or more other garments that either they have previously tried on. If the user has selected to try on multiple garments, step 618, then processing moves to step 620 where the system retrieves consumer drape 1102 that corresponds to the garment that the user wishes already display on their avatar before draping additional clothing.

In step 622, associated files for the simulation that are queued are then retrieved from data storages 110 and 170. For example, all or any combination of files stored in data storages 110 and 170 may be retrieved which may be required for the size algorithm, the simulation and the fit analysis described above.

In step 624, node polling system 912 is initiated. When the simulation request is read and all file locations have been verified, in step 626, the software running the queue system 903 checks the node polling system 912 to find an available GPU 1002. In one embodiment, GPU 1002 may reside in a GPU cloud computing center 1000.

In step 628, the polling system 912 is updated to reflect that the selected GPU 1002 is in use for the simulation request and not available for other simulations.

In step 630, 3D draping software application 900 then continues by processing the simulation on the selected GPU 1002.

The 3D draping software application 900 may be EFIT with slight modifications. For example, but not by way of limitation, 3D draping software application 900 may run EFIT without a GUI and user action. In other words, in one embodiment, 3D draping software application 900 is simply EFIT software that has been modified to run automatically by accepting simulation requests from the queue, loading the appropriate files, processing the simulation by draping the garment on one or more CPUs or GPUs, and then exporting the required output files Processing involves draping 3D virtual garment 183 on consumer avatar 161. The existing fit model drape 186 on fit model avatar 173 may be loaded onto consumer avatar 161. Then, the drape process may be continued to readjust to account for the difference in the two avatars. The resultant output is consumer drape 1102. Processing of cloth simulations in a 3D environment may be hardware-intensive. To those skilled in the art, GPUs 1002 are preferred for simulation of 3D graphics. However, when GPUs 1002 are not available, more traditional CPUs may be used in their place. In one embodiment, GPUs 1002 or CPUs can be run in parallel to increase simulation processing speed through multi-threading so long as the selected processor supports it.

Moreover, processing may include simulating for animation. In such a case, an animation file is loaded. The animation file may be of consumer avatar 161 walking, running, dancing, sitting, or performing any human motion. Draping is performed on each frame of animation of consumer avatar 161 and then stored in consumer drape 1102.

Figure 21:
FIG. 21 is a diagram showing an example of what a simulation and animation may look like on computer device in the context of a virtual fitting room according to one embodiment.

With reference to FIG. 21 a diagram shows an example of what the above simulation and animation may look like on computer device (24 in FIG. 1) in the context of a virtual fitting room according to one embodiment. In this embodiment, browser 26 is used as the interface.

Focusing back to FIG. 20, in step 634, data from resulting from the previous steps of FIG. 19 is exported. In one embodiment, the following data files may be exported and added to avatar data storage 170 and/or 3D virtual try-on data storage 1100 for later retrieval, by way of example, and not by way of limitation: consumer drape file 1102; 3D viewer data 1112; fit data 1104; and rendered media 1108.

In step 636, the node polling system 912 is updated to reflect that the selected GPU 1002 is now available.

In step 638, a fit analysis algorithm 906 may executed in order to determine qualitative and quantitative data with respect to the outcome of the simulation (the 3D virtual try-on process). A fit analysis object may be created to store this qualitative and quantitative data. The output of fit analysis algorithm 906 may also be fit data 1104 and/or rendered media 1108. Fit analysis may include deriving qualitative and quantitative data from a consumer drape 1102 for multiple sizes for a specific garment, or just one single size.

Fit analysis algorithm 906 may perform a stretch test to determine how much the virtual fabric is stretching in consumer drape 1102. Positive stretch values may indicate tighter fit areas, zero or a small stretch value may indicate areas of good fit or simply no-stretch. Negative stretch values may indicate areas of compression. In one embodiment, stretch values may be used to determine how well or how poor a garment fits an avatar. This data can then be stored additionally as fit data 1104.

Stretch can be calculated in many ways. For example, but not by way of limitation, stretch may be calculated by measuring the percent difference in a specific measurement before and after the drape. In other words, an initial garment measurement might yield one length. After draping the garment on an avatar, the draped garment measurement at the same location might have a length that has increased or decreased. In one embodiment, the percent difference in length for that specific measurement may be defined as the stretch value. In another embodiment, the stretch value may be calculated for many garment measurements, and the stretch value may refer to the total stretch of all garment measurements, or the average stretch value of all garment measurements.

Quantitative data may also include calculating the change in stretch in a similar fashion as described above, but with initial value set to the stretch value of the base size, and the final value being the stretch value of the selected size (if other than the base size). Furthermore, quantitative data may also include calculating the stretch value for specific points of measure, rather than for the entire garment, and then comparing them with the initial 3D virtual garment measurements from fit model drape 186. Moreover, quantitative data may also include calculating the total volume of space between the garment and the body and assessing how that total volume may increase or decrease from size to size. All data may be used together, or in pieces in a decision engine to establish a prediction of size. The decision engine may consider the total volume between the garment and the body, from size to size, versus the total stretch value, from size to size, and weight the two data types to arrive at the best fit of the garment to the body. It is well known to those skilled in the art that common procedures are available to determine how a garment is fitting using specific points of measure.

Figure 22:
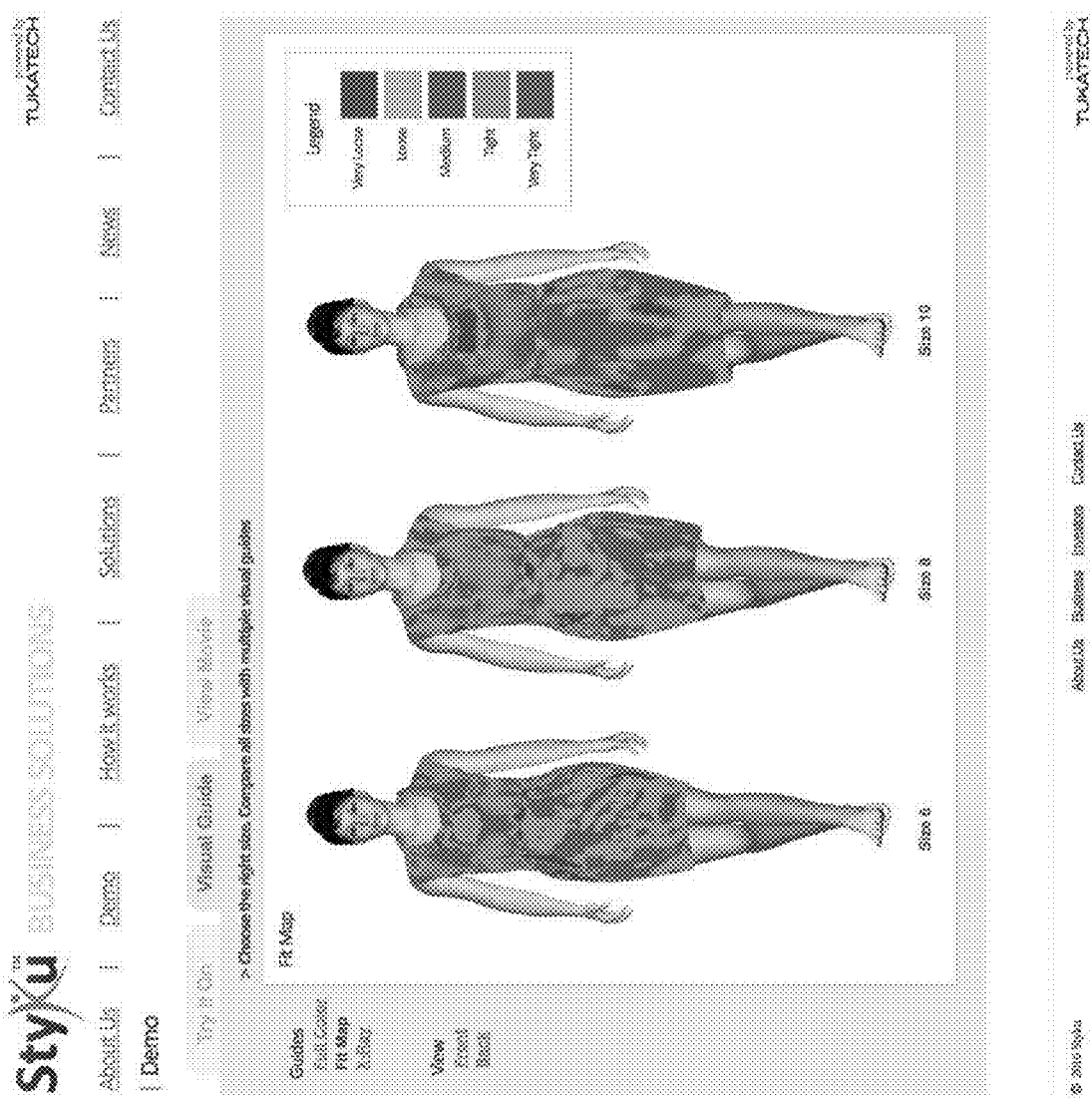
FIG. 22 is an example web page produced by a system according to one embodiment that illustrates how stretch values may be visually displayed using a color tension map.
Figure 23:
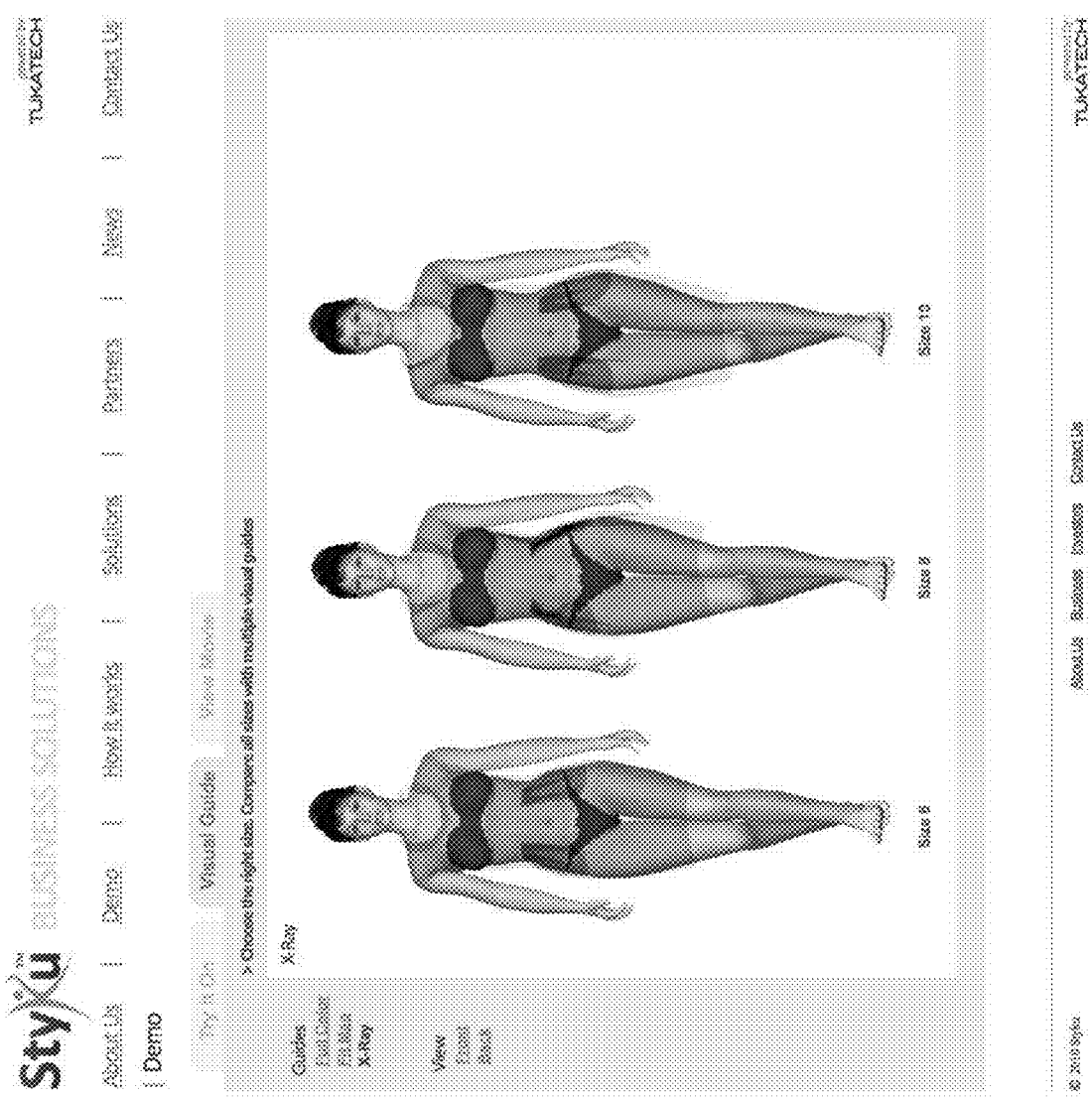
FIG. 23 is another web page produced by a system according to one embodiment that illustrates how another form of a visual representation of consumer drape may show the 3D virtual garment as partially transparent.

With reference to FIG. 22, an example web page produced by the system illustrates how stretch values may be visually displayed using a color tension map. These color tension maps can be viewed in any image format, on the web, or in any standard image viewing software. The color maps may also be viewable using 3D Viewer Application 82. The color tension map displays high stretch values in red, low stretch values in green, and negative stretch values in blue. data may include visual images of consumer drape 1102. Qualitative data may include a visual representation or image of the consumer drape using a color tension map to show the parts of the garment that are fitting tight, loose, or well. The color tension maps may be configured to show stretch values in certain directions with respect to the grain line of the fabric. For instance, a color tension map which display stretch values along the warp direction may be very different than a color tension map which displays stretch values along the weft or bias directions. Those skilled in the art may recognize different types of ways to present fit analysis data, including, by way of example, and not by way of limitation, using a color map showing shear, color map showing pressure on a body, color map showing pressure from air, color map showing drag force, color map showing tension color map showing compression, gray scale map showing shear, gray scale map showing pressure on a body, gray scale map showing pressure from air, gray scale map showing drag force, gray scale map showing tension or gray scale map showing compression With reference to FIG. 23, another web page produced by the system illustrates how another form of a visual representation of consumer drape 1102 may show the 3D virtual garment as partially transparent. This technique is referred to see-through mode, where the garment is partially transparent, and the user can see partially through the garment, revealing the avatar, and aiding the consumer in assessing how much space there is between the body and the garment. The opaqueness or transparency of the garment may also be adjusted.

Yet another form of visual representation of the consumer drape can be replacing the existing material texture of 3D virtual garment 183 with a one inch by one inch grid pattern, which is applied as a material texture, which reveals the slope or curvature of the garment along the body. Fit analysis algorithm 906 may perform many other types of calculations. For example, but not by way of limitation, fit analysis algorithm 906 may calculate the total volume of space, using methods in calculus, between 3D virtual garment 183 and consumer avatar 161 for all sizes of consumer drape 1102. This volume may aid in interpreting the correct size of the garment. Moreover, this calculation may aid in interpreting the fit of a garment.

The data gathered from the fit analysis algorithm, whether it be quantitative or qualitative or both, stored as fit data 1104, becomes extremely useful information to retailer system 50 and consumer system 50. More about this fit data will be discussed later Referring back to FIG. 20, in step 640, the output data may sent to the consumer's computing device 24 by way of either a browser 26 or software application 28.

In step 642, 3D viewer data 1112 and fit data 1104 are displayed in 3D viewer application 82 or 132. 3D viewer application 82 may be embedded in webpage viewed on browser 26 or is an application on consumer computing device 24. In another embodiment, 3D viewer application may run in ASP 100 and may be viewable in browser 26.

In one embodiment, 3D viewing application 82 or 132 is an interactive renderer java applet made with Java and Java 3D libraries, each available from Oracle/Sun, 500 Oracle Parkway, Redwood Shores, Calif. 94065, with built-in functionality to rotate, pan, zoom, and animate virtual garment 183 on consumer avatar 171. The user may also view the drape of one size larger or smaller than the estimated size. The user can also select to view the current virtual garment 183 with a color tension map, in x-ray mode, playback animation of the drape, or view the garment with the avatar hidden from view. Moreover, the user can render an image to save in common image formats. 3D viewer application 82 or 132 may also have other interactive features that allow the user to rotate, pan, and zoom the 3D content. The user may also be able to annotate the garment with comments. Moreover, live sharing and chatting may be implemented so that the user can share the content live with another user. Chatting and video applications may be embedded allowing users to communicate further and discuss the 3D content.

Discussed above was an embodiment of 3D viewer application 82 or 132 written in Java and Java 3D. However, it is important to note that 3D viewer application 82 may be an interactive renderer created using c++, python, or any programming language capable of creating 3D web applications.

In one embodiment, in step 644, the user can rate and/or review the fit of the garment by giving a thumbs-up or thumbs-down. In another embodiment, the user can rate and/or review the garment on a numeric scale. In yet another embodiment, the user can rate the garment as "Fits well, too tight or too loose". Other rating systems known to those skilled in the art can be used. All such reviews described above can be stored in 3D virtual try-on data storage 1100 as user reviews 1106.

In step 646, the user are given the option of saving consumer drape 1102 of 3D virtual garment 183 for future viewing or mixing with other garments for viewing (e.g., shirt and pants). If saved, virtual garment 183 appears in user's virtual closet 290 where the collection of consumer drapes 1102 are available for the user to view again. The user's subsequent action(s) are tracked within the application and/or webpage to determine whether they purchase the garment. If the user chooses to purchase the garment, an email notification may automatically be generated to the user notifying them that the virtual garment 183 has been saved in their user profile and can be viewed at any time by logging into the ASP 100's web portal using computing device 24.

Virtual closet 290 may be accessed when the user is logged into ASP 100. Virtual closet 290 may store consumer drapes 1102 of 3D virtual garments 183 that have been purchased and recently viewed. In one embodiment, virtual closet 290 may display these garments 183 as visual images of drapes that do not include the model.

Items in the closet may be viewed in 3D viewing application 30 can be viewed with other 3D virtual garments 183, for example, from the same retailer, or a different retailer, or mixed and matched in other ways.

In some embodiments, the virtual closet 290 may also provide for sharing between users. With social media integration, a user may share the results of their fit with contacts in facebook, myspace, yelp, and other social media sites, as well as personal websites or for viewing in applications in any computing device. The user may select a save image function that allows the user to take a picture or snap shot of the consumer drape 1102 of 3D virtual garment 183 on the avatar, and then upload it to their profile on a social media site.

Fit Analysis for Consumers

With the data collection (consumer drape 1102, fit data 1104, user reviews 1106, rendered media 1108, and consumer avatar 171) that is accomplished by system 10 described herein, such data may be analyzed to discover trends and draw conclusions, which can, for example, provide feedback into the system and provide further granular analysis (step 306 in FIG. 3). For example, fit analyses for consumers may be performed on the collected data. In this regard, there is a tremendous value in data analyses of the production garments 59 consumers have purchased and not-returned. The production garments 59 are a reflection of the consumers' buying behaviour. Tracking and studying the buying behaviour is known to provide valuable information to those skilled in the art. However in the past, analyses have been limited to color, size, and fabric information for apparel goods. For the first time using the presently described system, consumer buying behaviour can now include fit.

Figure 24:
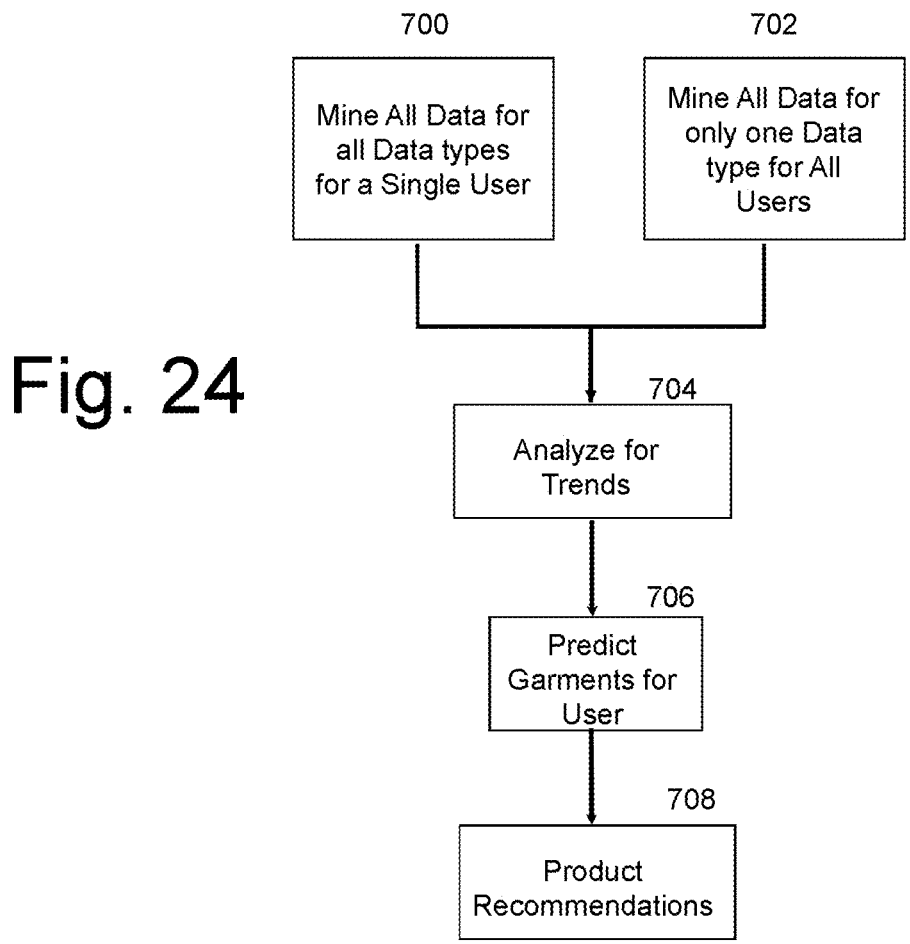
FIG. 24 is a flowchart that describes a process of analyzing fit data according to one embodiment.

FIG. 24 is a flowchart that describes a process of analyzing the fit data according to one embodiment. In step 700, data collection is performed. When a garment is purchased, a copy of the related consumer drape 1102 of 3D virtual garment 183 is stored in virtual closet 290. Fit data 1104, user reviews 1106, rendered media 1108, and consumer avatar 171 may also be stored as part of the user profile 190 on ASP 100. All this information together can be gathered together, in step 700, for a single user, or together, as in step 702.

Then, in one embodiment, in step 704, the data can be mined to find trends in buying behaviour, trends in consumer drapes from one garment to another, and or trends in body shapes with particular garments or particular retailers. For example, but not way of limitation, stretch factor calculations for relevant points of measure calculated for the virtual garment 183 could be analyzed across multiple garments for a single user, or multiple users.

Moreover, in step 704, trends in stretch factor, or other fit data may be correlated with demographics, retailer's, fit model's, sizes, fabric types, revealing valuable information. For example, but not by way of limitation, such analysis may reveal that a consumer fits better with a certain set of brands, then with another set of brands. Such information becomes useful in step 706. Moreover, such correlations may be easily recognized by those skilled in the art given the data the present system makes available, since brands often have fit models with distinctively different body shapes.

In step 706, the trends discovered in step 704 may be used to better predict the outcome of fits with virtual garments in system 10 and can be used as size prediction algorithm 908. Furthermore, fit may be a very subjective personal choice for consumers. For instance, two people of very similar body types may have dramatically different viewpoints on fit, where one person may prefer a tighter fit, or a size larger than the other. Therefore, by studying how variables that measure stretch across multiple garments for groups of similar bodies, and discovering trends, those trends may now be applied to predict other garments that may fit a user.

In step 708, a product recommendation engine is built to interpret predicted garments in step 706 and then suggest those garments to the user in ASP 100.

Finally, data collected can be used directly to make custom patterns and therefore custom garments for the consumer. The data may be used to develop block patterns, or customize the patterns of garments available by the retailer. Custom 3D garments and patterns may be sent to the retailer based on the analysis.

Fit Analysis for Retailers

Conversely, consumer drape 1102, fit data 1104, user reviews 1106, and rendered media 1108 may all contain extremely valuable information not only for aiding consumers in buying clothing online, but also for apparel manufacturers and retailers. Retailers can use such information to better understand their target market, make necessary adjustments to product development, distribution, production, merchandising, and other key decisions in supply chain and sales processes referred to above. Currently, retailers have no immediate perceivable method of determining how a garment truly fits on each of their customers. Often times, retailers depend on statistical studies to determine the body shape(s) of their target market. Moreover, they rely on third-party research organizations that study body shapes in certain populations. However, the shapes of human bodies are difficult to standardize and are constantly changing. In consequence, most retailers fall short in reaching the broad target market they were designing for.

Figure 25:
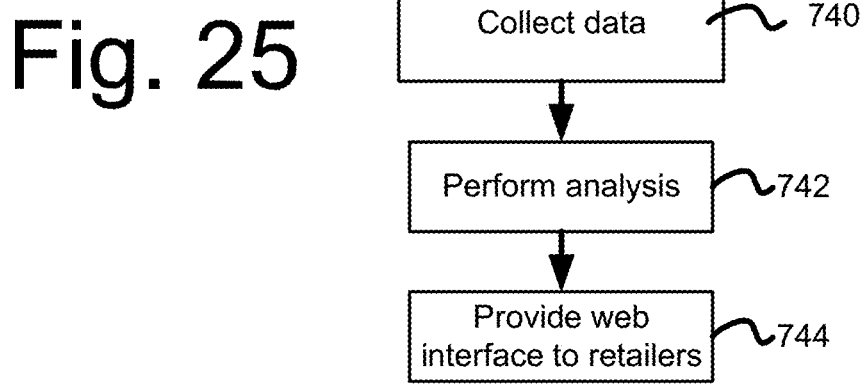
FIG. 25 is a flow diagram that illustrates steps to relate fit data and how retailers may interpret such relations according to one embodiment.

With reference to FIG. 25, a flow diagram illustrates steps to relate fit data and how retailers may interpret such relations. In step 740, data collection is performed. For example, the following data may be collected after each fit is performed on a consumer: (1) number of fits a consumer has in a set period of time; (2) percentage of fits that results in a sale; (3) number of times of consumer try's on a specific garment; (4) the average stretch factor for each fit; and (5) each consumer's fit history and measurement chart. In step 742, a data analysis may be performed on this data. This data can be used to determine which garments are fitting which body types. Correlations between body measurements, or sets of body measurements and purchases can be determined. Such correlations can be used to predict the probability that a certain consumer, based on their body shape, will or will not buy a specific garment. Additionally, a point-to-fit analysis may give retailers access to measure in real-time the fitting process with each of its site's visitors. Such information can be used to determine how garments are performing in the virtual fitting room. Furthermore, those results can help retailers determine if changes to the construction of the garment may or may not increase sales. In another embodiment, retailers may access consumer drape 1102 and derive their own fit data from the actual draped virtual fabric. Furthermore, retailers may compare these drapes with fit model drape In step 744, a web interface, may be made available to retailers. By logging on, retailers may have access to daily, weekly, monthly, quarterly, or yearly statistics on user data, which can be manipulated and searched.

3D Body Scanning Using Range Camera and Augmented Reality

Figure 26:
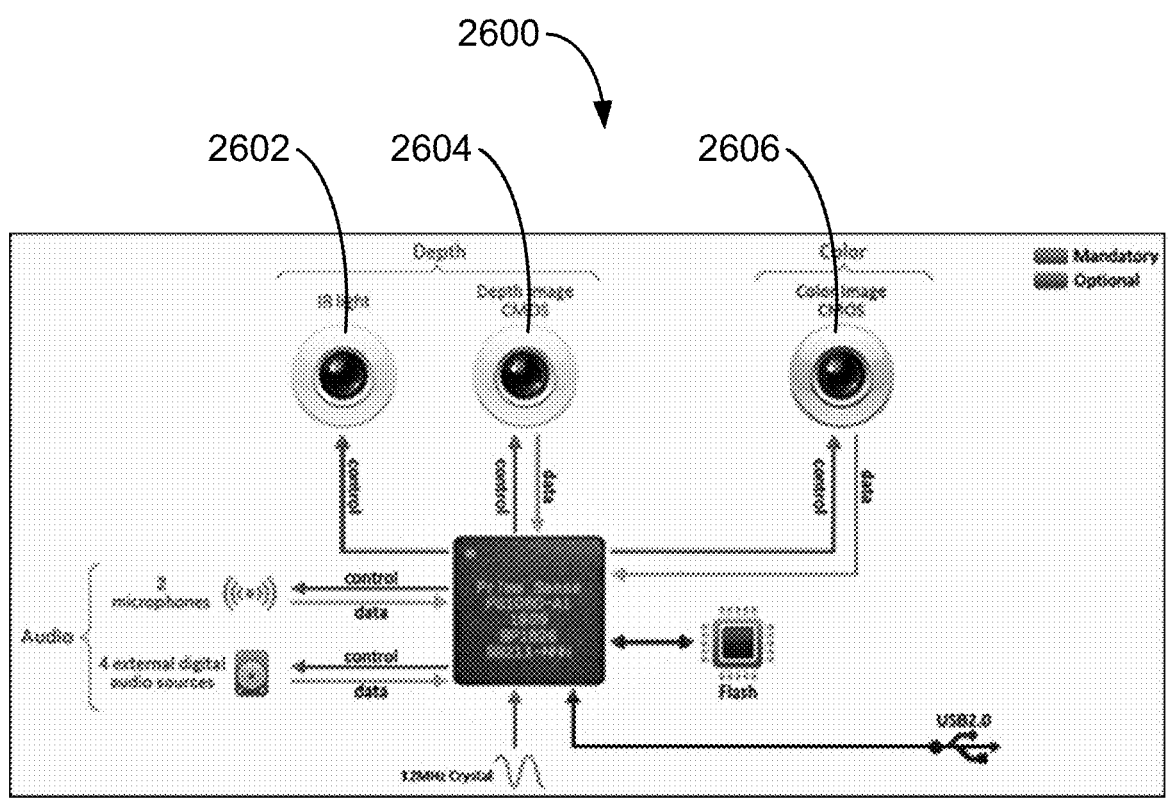
FIG. 26 is a diagram illustrating components of a prior art range camera device that could be used in one embodiment.

Range Cameras may include, for example, the Microsoft 3D Kinect device. With reference to FIG. 26, a diagram illustrates a prior art range camera device 2600 that could be used in one embodiment. A range camera device 2600 of this type may include, for example, a small shoebox sized attachment used for motion capture for video game consoles, or the like. This type of range camera device 2600 may include an infrared (IR) light emitter 2602 that emits structured infrared light, a red-green-blue (RBG) camera 2606, and a CMOS IR sensor 2604 for reading reflected IR light. The RBG camera 2606 is used to take visual images, whereas the IR emitter 2602 and CMOS sensor 2604 are used in conjunction to measure depth of objects within the field of view.

In one embodiment, the system described herein may use the depth images attained by the CMOS sensor 2604 to create a 3D model of a subject or object within the field of view. Further, a process of capturing depth images of a human subject and creating a 3D model or avatar of the subject may be performed by one embodiment.

Figure 27:
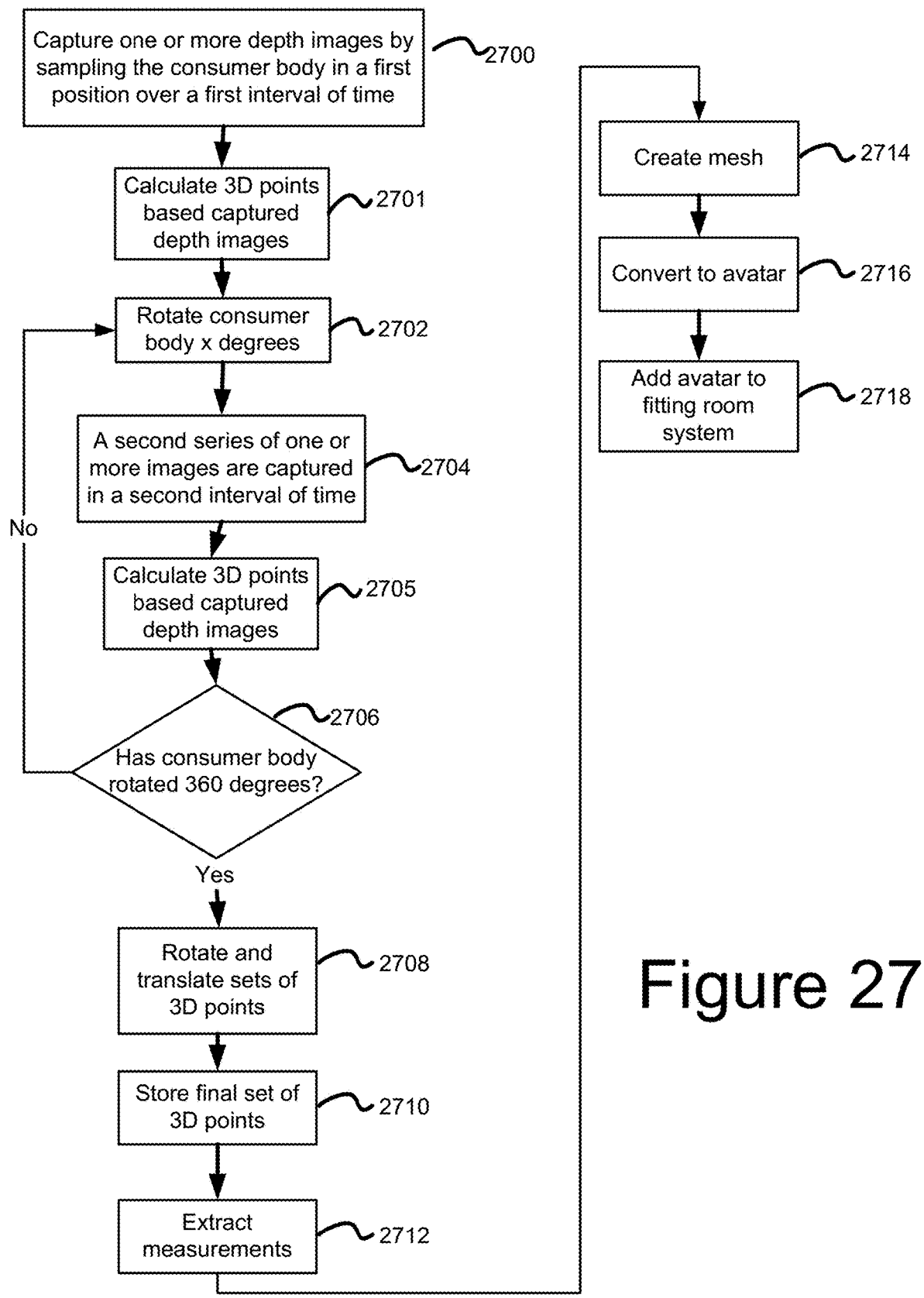
FIG. 27 is a flow diagram illustrating steps that may be performed using a range camera of FIG. 26 in one embodiment.

With reference to FIG. 27, a flow diagram illustrates steps that may be performed in one embodiment for scanning consumer body 22 using range camera device 2600. In step 2700, a set of computer instructions, which is written and available from OpenNI™, may be used to capture one of several depth images by sampling consumer body 22 in an interval of time and in a fixed position in space with respect to the range camera device 2600. OpenNI™ is middleware that is part of the free software development kit (SDK) provided by PrimeSense, located at 28 Habarzel St. 4th floor, Tel-Aviv, Israel, 69710.

Each depth image may contain the depth or distance to the body, as well as the xy position of each part of their body, also called 3D position data.

In step 2701, a library routine of OpenNI™ may be called to calculate actual 3D points from the captured depth images from step 2700. In step 2702, consumer body 22 may next be rotated or rotate to a secondary position, by way of example, and not by way of limitation, 90 degrees.

With reference to FIG. 90, a diagram describes a scanning system that uses a mechanical or electrical rotation device 8700 controlled by computing device 153 that may be used in step 2702 to rotate consumer body 22.

Next, in step 2704, a second series of one or more images may be captured in a second interval of time. In step 2705, the library routine of OpenNI™ may be called to calculate actual 3D points from the captured depth images from step 2704.

In one embodiment, the operator of the scanning system begins rotation of the rotation device 8700 while the range camera device 2600 captures 30 depth images per second of the consumer body 22 being rotated by the device, resulting in the capture of depth images of the consumer body from different angles.

The process is repeated until the subject has rotated 360 degrees, as indicated by decision diamond 2706. The result is a series of 3D points, one set for each capture of images at a rotation stop point as described above.

In step 2708, each set of 3D points corresponding to a rotation of the consumer body 22 is rotated and translated such that they all are able to fit together to form a final set of 3D points to represent the entire consumer body 22. This final set of 3D points are stored in step 2710.

Next, in step 2712, measurements may be extracted. This may be performed various convex-hull algorithms, for example, the Graham scan algorithm or the Andrews monotone convex-hull algorithm.

In step 2714, a 3D mesh is created from the 3D points. This can be performed by various methods that are commonly used to convert 3D points to a 3D mesh. For example, ball pivoting algorithms, Poisson surface reconstruction, or the like, may be used for this step.

In step 2716, the mesh may be converted into 3D consumer avatar 171 as described above. For example, the mesh could be rigged, skinned, and have a texture applied so that it could be animated and customized to look like the consumer body 22. In step 2722, the consumer 22 could then use this consumer avatar 171 for an online fitting room as described above. As described above, clothing could be modelled as a 3D mesh, as in the case with digital patterns, and then using the cloth simulation algorithms described above, clothing may be simulated on the avatar in 3D, allowing for the consumer 171 to view in real-time how a garment will look and fit their own body.

In some embodiments, another sensor could be put behind the consumer 22, or several at different angles. However, to keep hardware cost down and to make the system more practical for in-home use, consumer 22 may alternatively be asked to rotate their body to capture their body from multiple angles as described above.

In step 2714, the corrections in change of posture may be made by using a pose tracker library by OpenNI. The OpenNI library contains functions for tracking poses by assigning a skeleton to the consumer body 22. For example, if the arm position has changed from the first series of images, to the next series of images after the body was rotated, then using the pose tracker, the new position of the arm can be used to translate the 3D points associated with the arm to the old position of the arm in 3D space, thereby, correcting for movement by the user.

Alternatively, the consumer avatar 171 could also be drawn on a monitor or flat-panel display connected to a computer or gaming system, and then be synced with the consumer's movements, such that the consumer could control its movements.

Using a technique known as augmented reality, one skilled in the art of augmented reality systems would recognize that 3D graphics could be displayed on a live video stream from RGB camera 2606. Those 3D graphics could be consumer avatar 171.

3D virtual garment 183 draped on consumer avatar 171 could also be displayed using augmented reality and dynamically draped using GPU cloth simulation. In this respect, 3D virtual garment 183 may be simulated with animation in real time on consumer avatar 171 no matter what position or posture consumer avatar 171 takes in real time.

Moreover, consumer avatar 171 could be hidden from view such that it would appear to the consumer 22 that the 3D virtual garment 183 were actually on consumer body 22 as they see it in real time on the monitor.

For example, consumer body 22 may change poster wherein the arm may change position in 3D space, using the pose tracking algorithm developed in OpenNI™, consumer avatar 171 may adjust its position to match the new position of consumer body 22. Since the consumer avatar 171 hidden, this will thus cause 3D virtual garment 183 to re-simulate using the cloth simulation algorithm resulting in a new drape consistent with consumer body 22's new posture.

3D Body Scanning Using Multiple Range Cameras
Introduction

Inexpensive depth sensor technology, sometimes called range camera technology, has become readily available by multiple vendors for consumer and commercial applications. Moreover, open source software libraries and software development kits (SDK) have been provided by those vendors to develop new applications utilizing this technology. Presented here is a new application that utilizes multiple range cameras to create a 3D human full or partial body scanner (hereafter 3D body scanning system). In one embodiment, the 3D body scanning system is mounted on a pole or several poles, vertically or horizontally, or mounted on a wall or several walls within a booth or within a room of any size. Additionally, the sensors may be angled. The sensors are configured to scan, via software, either all at once, within some timing of each other, or in some predefined order, to capture depth and 3D position data of a subject. An associated RGB camera may also be used to assign a color for each 3D position data point (a collection of such 3D position data points hereafter referred to as a "point cloud"). The resultant point clouds, with or without color information, can then be registered or transformed into one common coordinate system, via a registration algorithm, creating one point cloud representing a full subject or parts of a subject. Then, that point cloud may be interpreted by a meshing algorithm, using standard practices or a novel method, to create a triangular or polygon mesh (hereinafter mesh). Finally, that mesh can be used for a virtual try-on (as described above). Described below are multiple sensor position configurations, multiple registration algorithms and calibration assemblies, multiple sensor timing and ordering schemes used for capturing depth images, and multiple meshing algorithms used for converting the resultant 3D point cloud into a mesh.

Range Cameras

Figure 28:
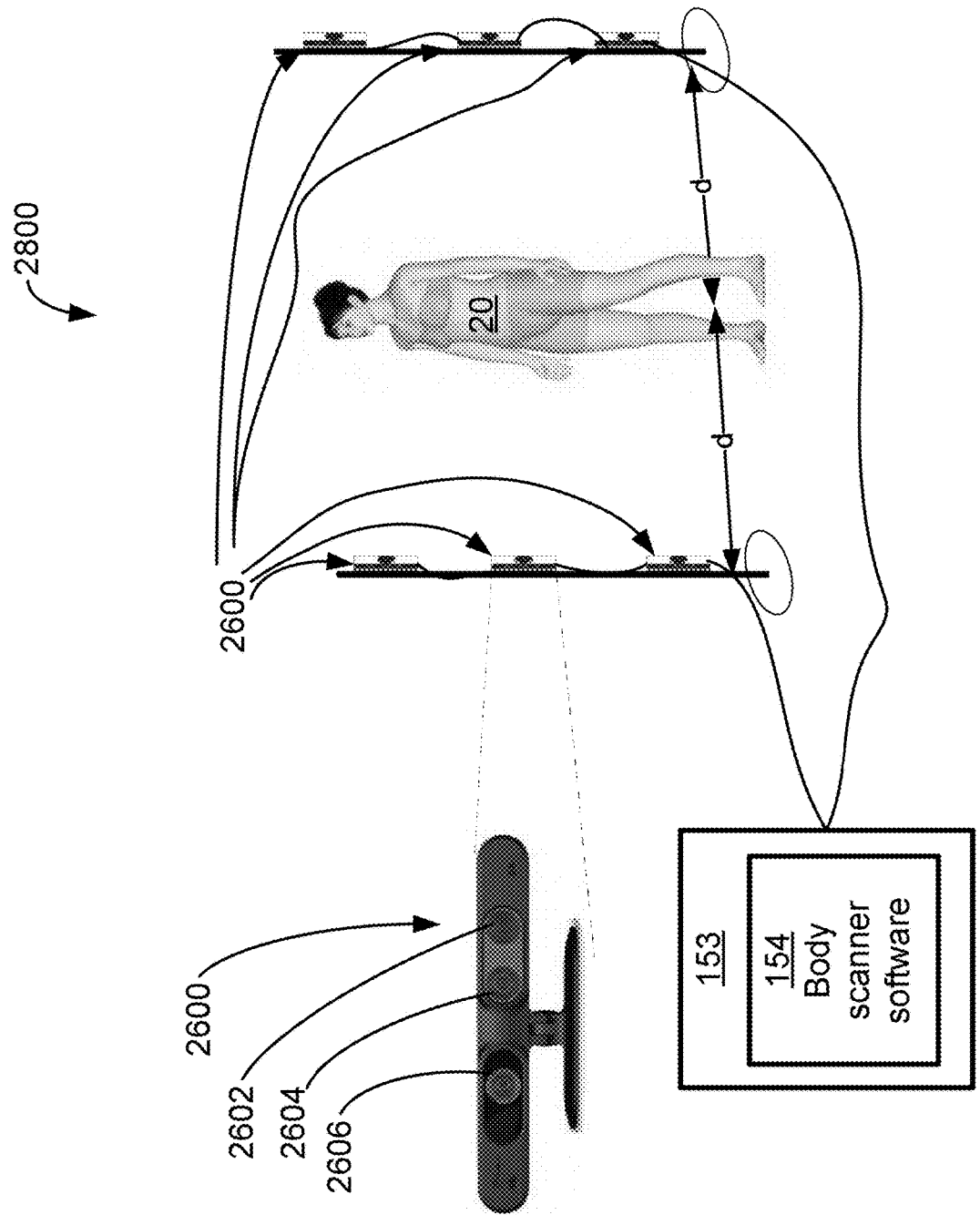
FIG. 28 is a diagrammatic illustration of a two pole-type scanner system according to one embodiment.

Range cameras may comprise, by way of example and not by limitation, devices available from PrimeSense, 28 Habarzel St., Tel-Aviv, 69710, Israel, the Xtion Pro or Xtion Pro Live from ASUS Computer International, 800 Corporate Way, Fremont, Calif. 94539, the Kinect available from the Microsoft Corporation of Redmond, Wash., or devices from other vendors that use range sensors or cameras. With reference to FIG. 28, a range camera 2600, such as the Asus Xtion Pro Live (depicted), may include an infrared (IR) light emitter 2606 that emits structured infrared light, a red-green-blue (RBG) camera 2604, and a CMOS IR sensor 2602 for reading reflected IR light. The RBG camera 2604 is used to take visual images, whereas the IR emitter 2606 and CMOS sensor 2602 are used in conjunction to measure depth of objects within the field of view.

Figure 29:
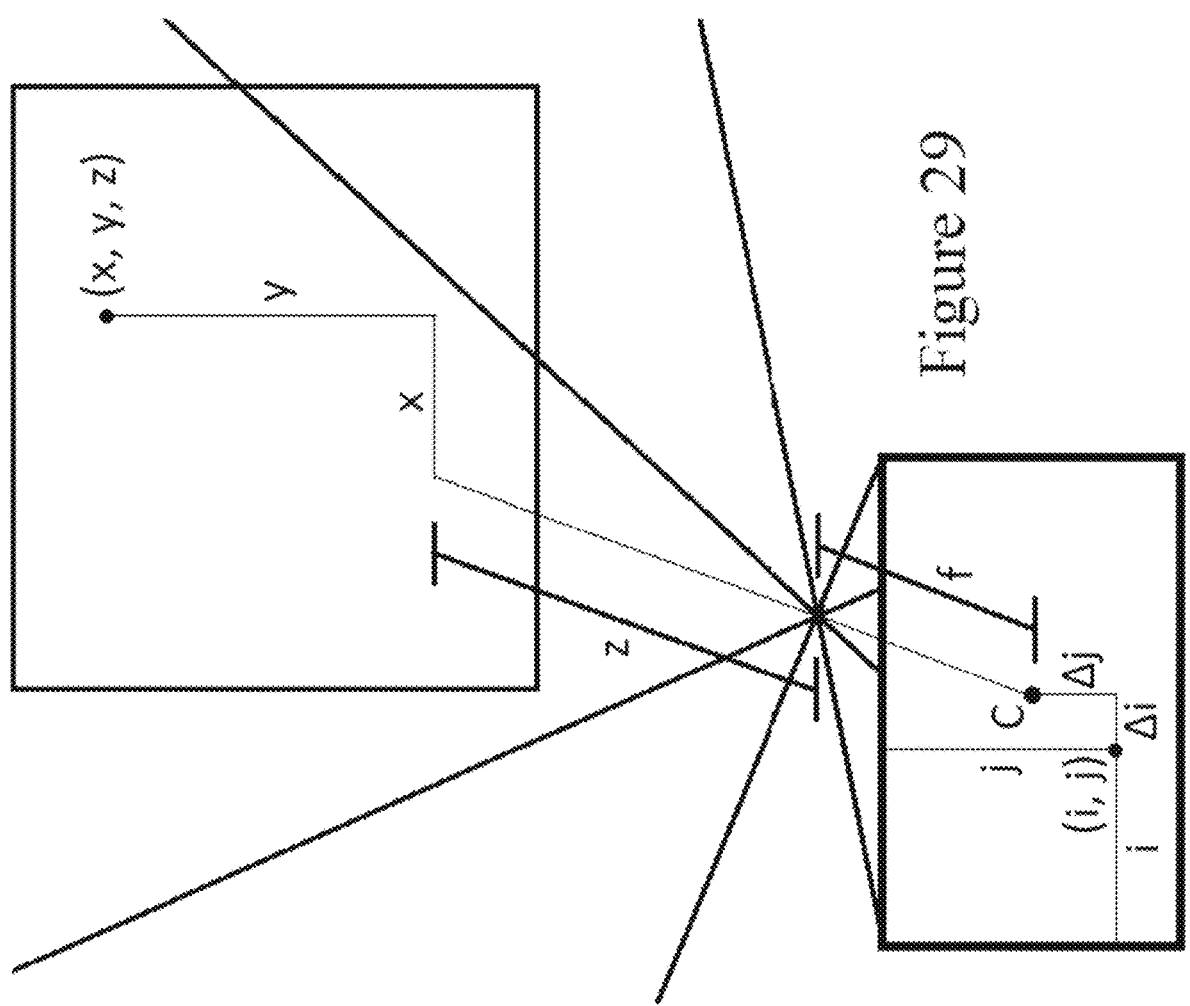
FIG. 29 is a diagrammatic illustration of a two dimensional range image generated by a range camera according to one embodiment.

With reference to FIG. 29, in embodiments utilizing one of the range cameras outlined above, a 2D range image generated by such a range camera is depicted. For each pixel with coordinates (i, j) in the range image, a corresponding real world point is represented by a range value z, which is the distance between the range camera focal point and the plane that is parallel to the image plane and contains point. Each (i, j, z) tuple may then be converted into Cartesian coordinates (x, y, z) relative to the range camera by using the range camera focal plane distance parameter f and 2D image centered pixel coordinates (Δi, Δj), the offset from the image center C, in the following equations:

$$x = \frac{(z)(\Delta i)}{f},$$

$$y = -\frac{(z)(\Delta j)}{f}$$

Body Scanning System Configuration

The following describes multiple relative placements of range cameras around a subject, hereinafter referred to as body scanning system configuration or range camera configuration.

Figure 30:
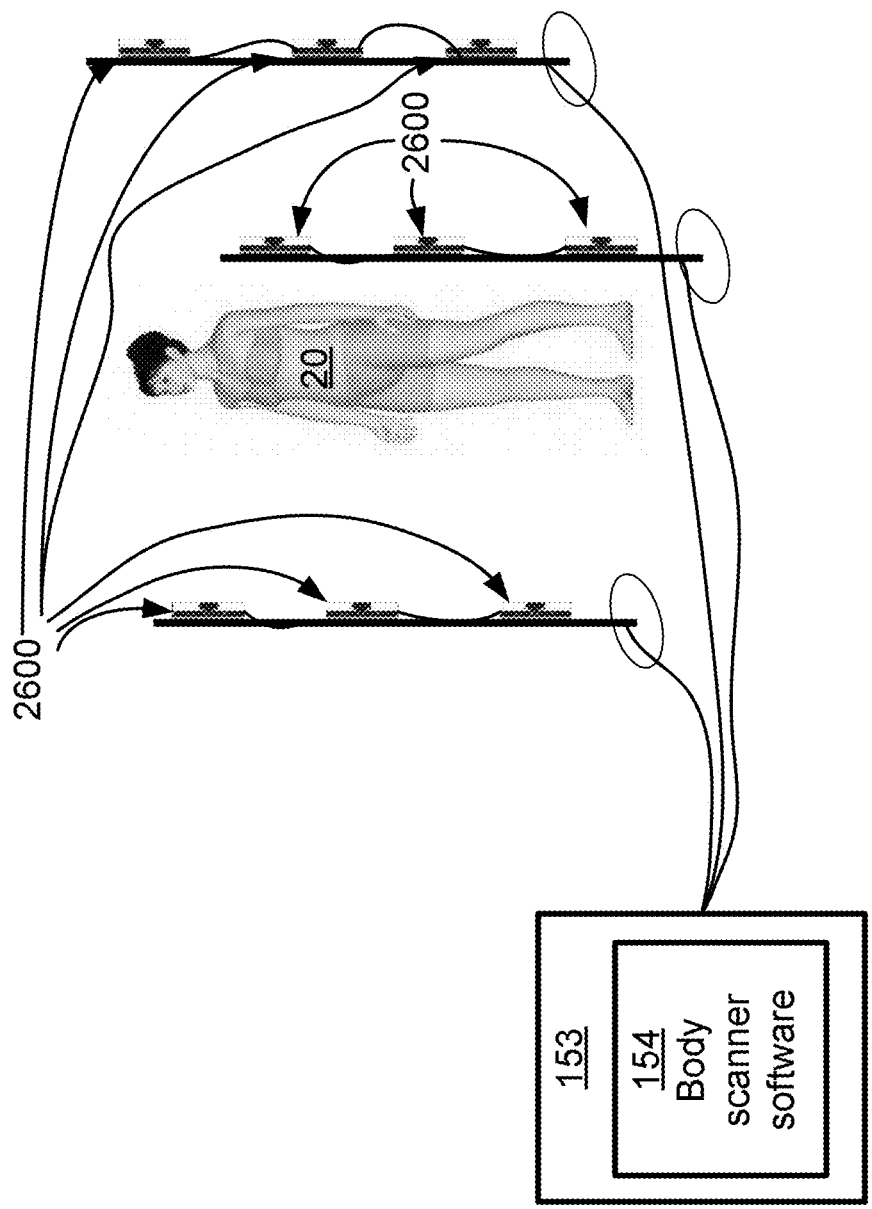
FIG. 30 is a diagrammatic illustration of a three pole-type scanner system according to one embodiment.
Figure 31:
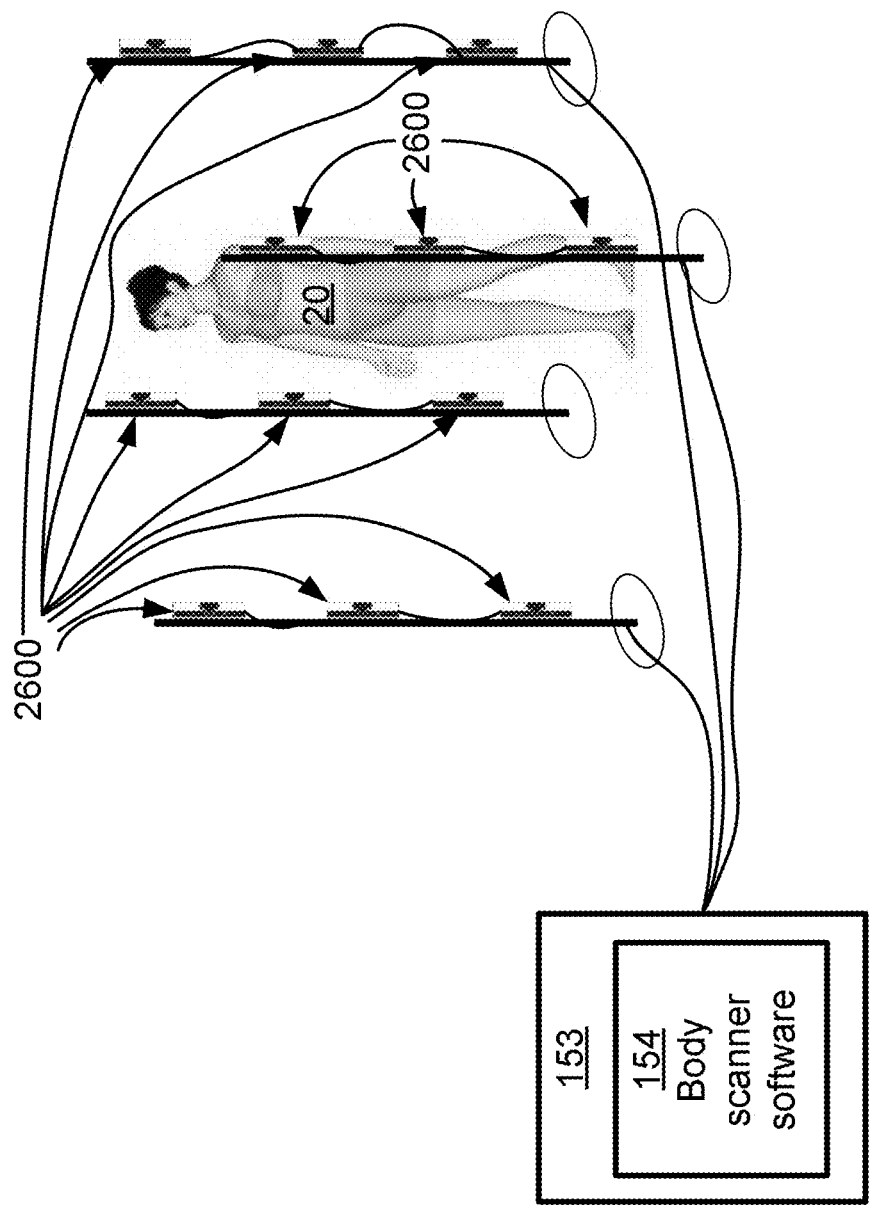
FIG. 31 is a diagrammatic illustration of a four pole-type scanner system according to one embodiment.
Figure 32:
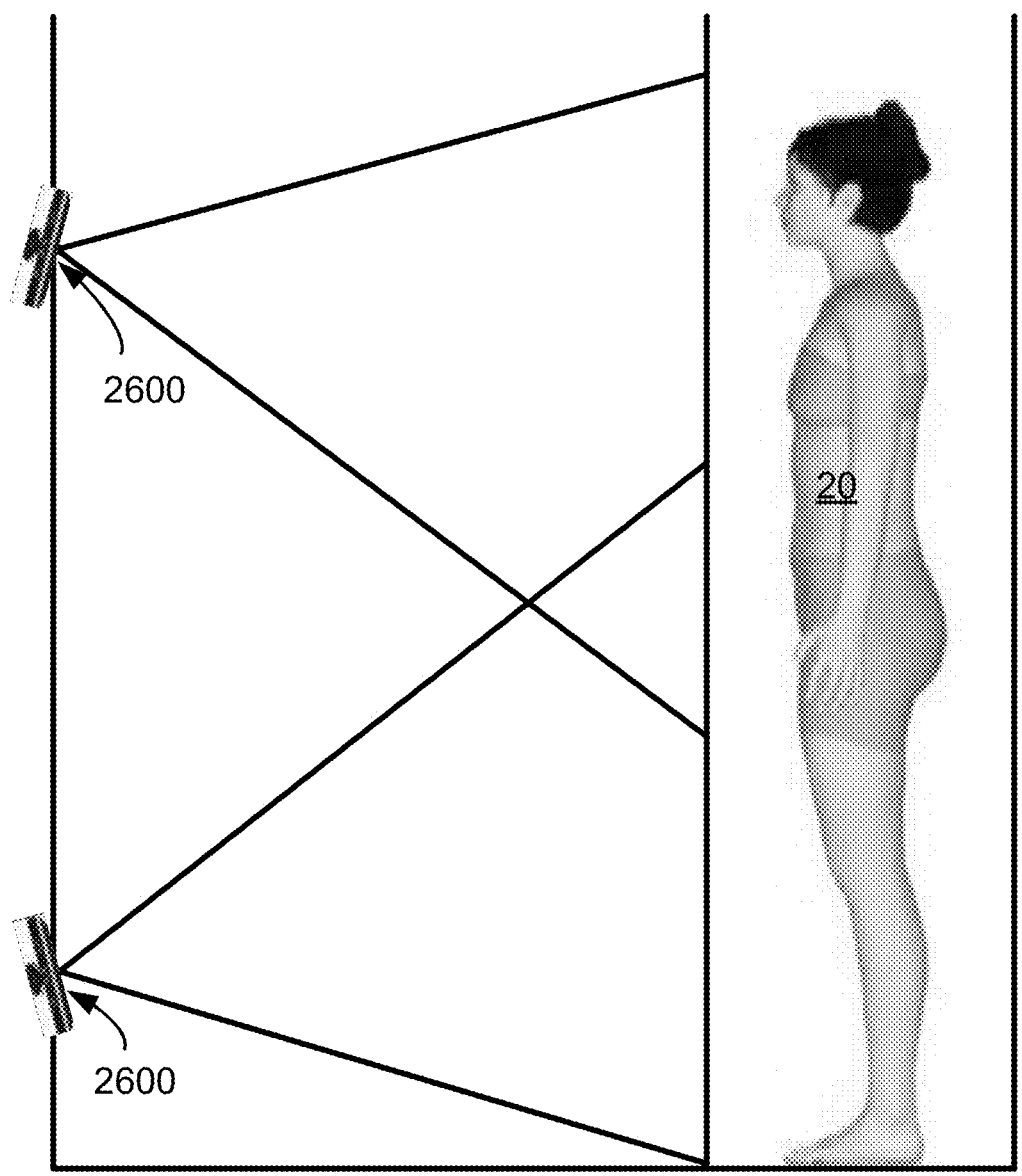
FIG. 32 is a diagrammatic illustration of a range camera pair positioned on a pole according to one embodiment.
Figure 33:
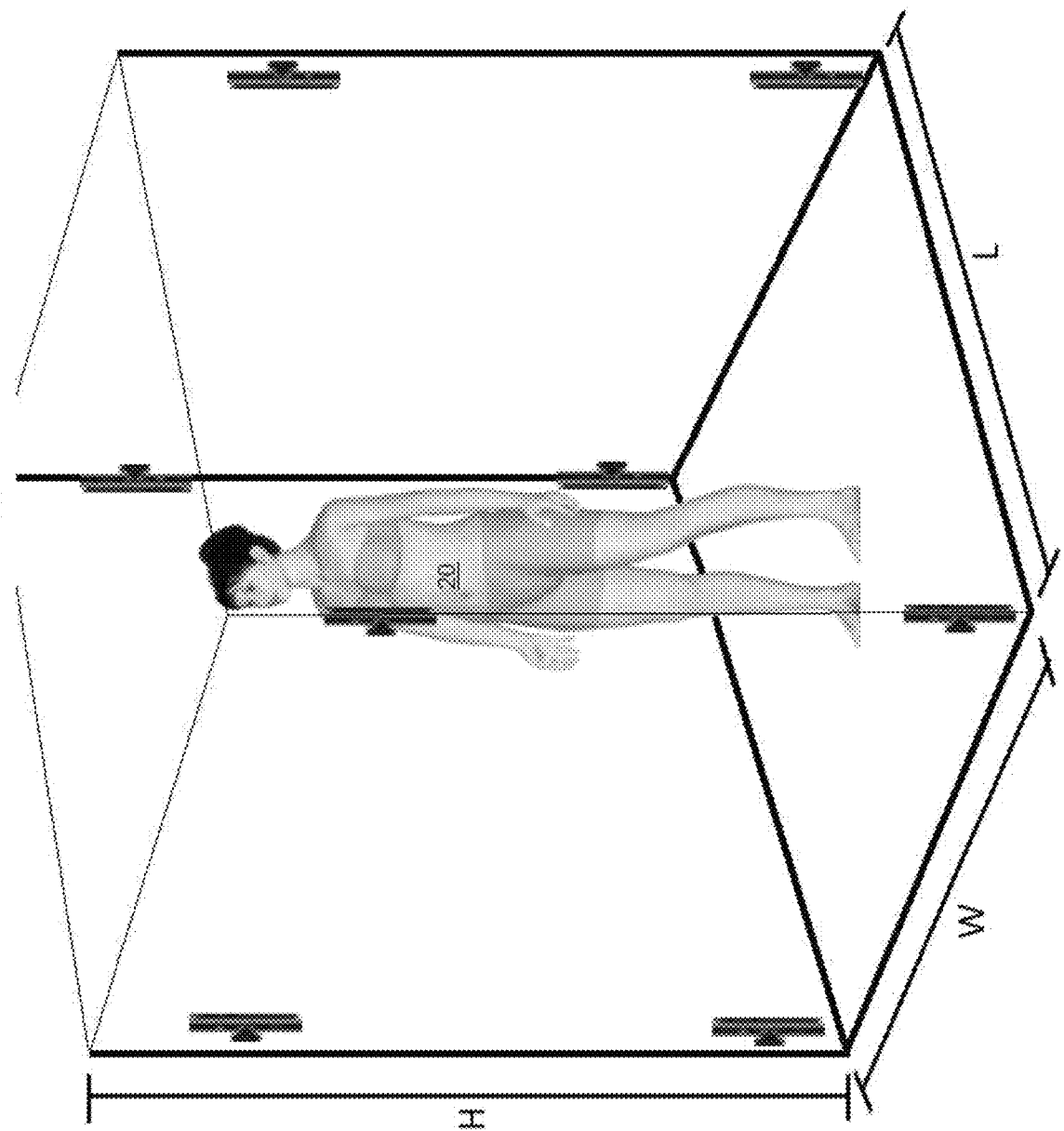
FIG. 33 is a diagrammatic illustration of a sample placement of range cameras positioned on walls of a room.

In several preferred embodiments, one or more cameras may each be positioned along two or more vertical axes surrounding the scan area. By way of example and not by limitation, with reference back to FIG. 28, a body scanning system 2800 may consist of, in addition to computing device 153 and software 154, six total range cameras 2600, three each placed on two axes which may be positioned directly in front and behind a subject 20. In another embodiment, with reference to FIG. 30, three sensors 2600 may be placed on each of three vertical axes. The three vertical axes may be positioned such that one is directly behind a subject 20 and the other two are positioned in front, to the left and the right of a subject. These vertical axes may be placed such that their intersections with the ground form vertices of a triangle. That triangle may be an isosceles, equilateral, or scalene. In another embodiment, with reference to FIG. 31, four vertical axes are positioned as if at the vertices of a rectangle, with the subject 20 facing one side of this rectangle. In another embodiment, with reference to FIG. 32, a pair of range cameras 2600 may be placed on one or more vertical axes. Moreover, the range camera pair, in one embodiment, may consist of one range camera positioned near the floor and angled upwards, and one range camera positioned near the ceiling and positioned downwards. In other embodiments, any number of range cameras may be positioned along an axis, axes may be horizontal or aligned in some other direction, and/or range cameras may be positioned without regard to any axis. Range cameras may be affixed to a pole as shown in the aforementioned Figures, to one or more walls as shown in FIG. 33, or to some other structure.

Figure 34:
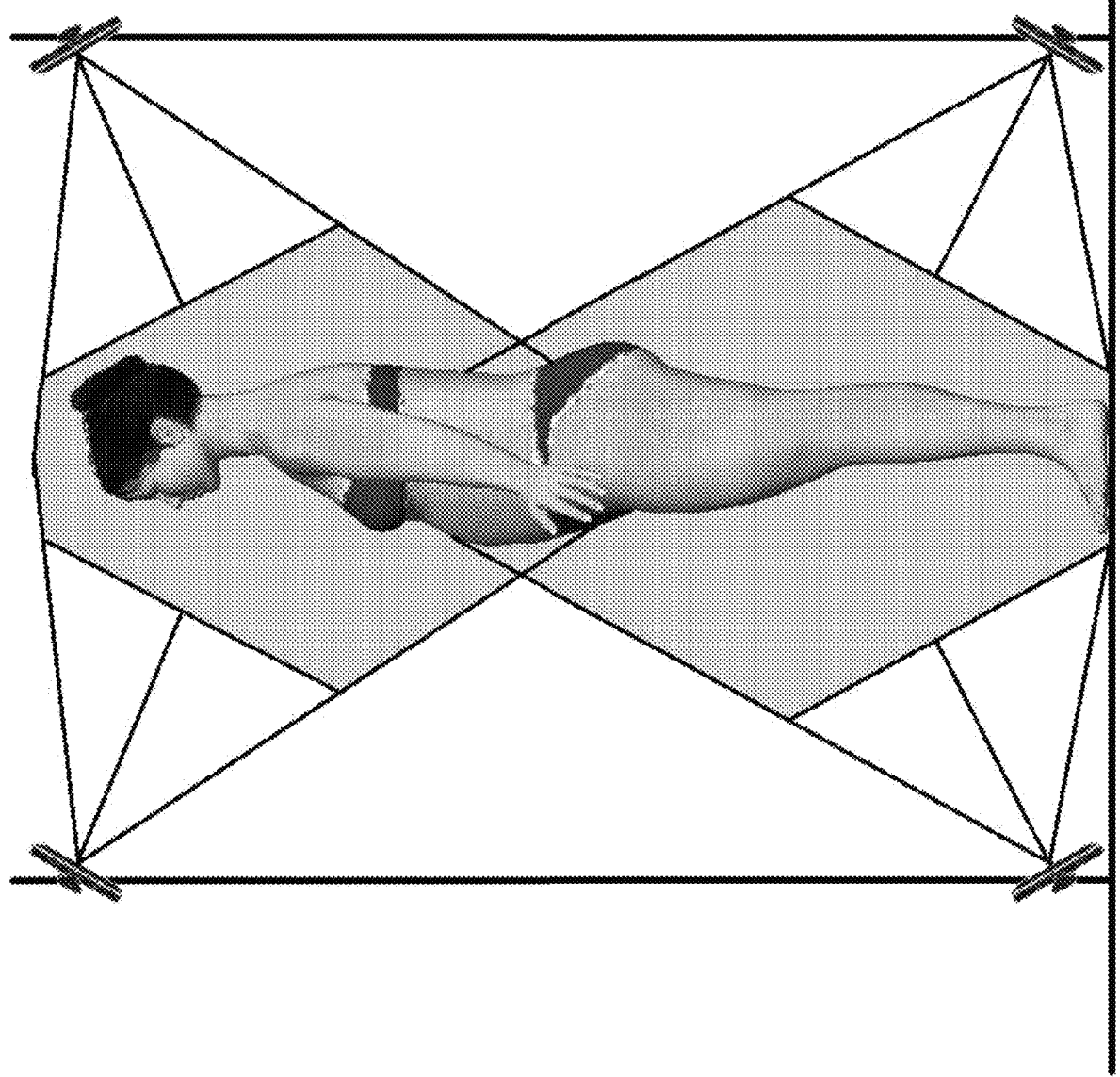
FIG. 34 is an illustration of how the range camera vertical field of view and minimum detectable depth, as well as the height and girth of a subject, may determine each range camera's height, tilt angle, and distance from the subject.
Figure 35:
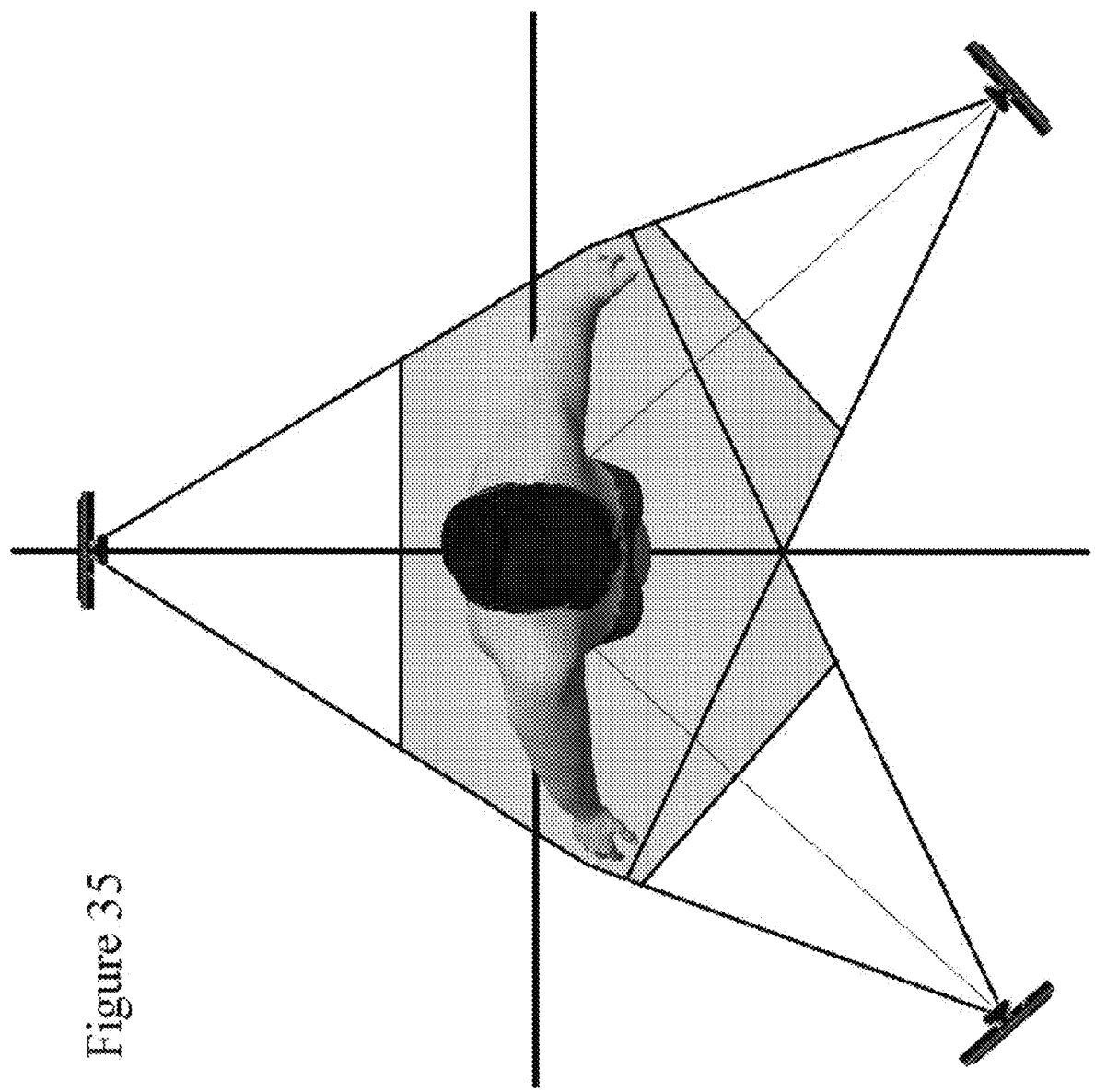
FIG. 35 is an illustration of how the range camera horizontal field of view and minimum detectable depth, as well as the pose and arm placement of a subject, may determine each range camera's line-of-sight azimuth angle, and distance from the subject.

Several constraints may limit the range camera placement described above. Some of those constraints are as follows: (1) the volume available for the 3D body scanning system (by way of example and not by limitation, with reference back to FIG. 33, the length L, width W, and height H of a dressing room), (2) the overall size of a subject to be scanned (height and girth), (3) the size and position of features of a subject being captured or scanned (by way of example and not by limitation, with a human subject, features such as feet, crotch, buttocks, gut, arms, breasts, head, and other features of a body), and (4) range camera parameters/characteristics (by way of example and not by limitation, horizontal and vertical field of view, pixel resolution, minimum and maximum detectable depth, interference between sensors, depth resolution, noise, and bias). Different combinations of constraints may necessitate different embodiments for different applications. By way of example and not by limitation, FIG. 34 illustrates how range camera vertical field of view and minimum detectable depth, as well as the height and girth of a subject, determines each range camera's height, tilt angle, and distance from the subject. Again by way of example and not by limitation, FIG. 35 illustrates how range camera horizontal field of view and minimum detectable depth, as well as the pose and arm placement of a subject, determines each range camera's line-of-sight azimuth angle, and distance from the subject.

Figure 36:
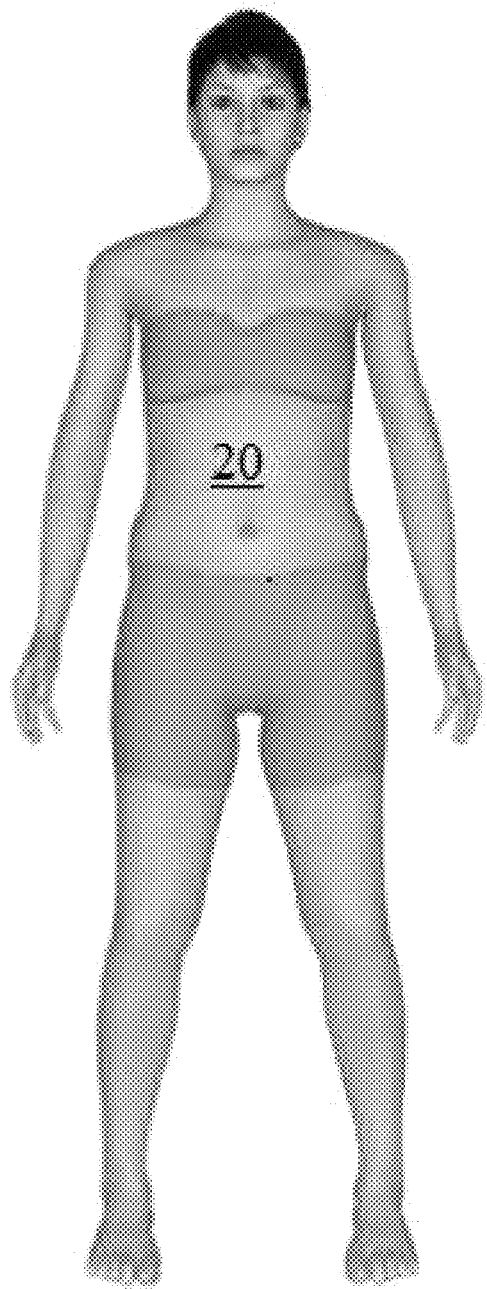
FIG. 36 is an illustration of a person who may be a scanning subject in a pose for scanning.

With reference to FIG. 36, in one embodiment, the subject 20 is required to hold the pose shown: standing straight, legs slightly apart, and arms to the side, slightly away from the body. This pose is designed to fit the subject within the range cameras' fields of view, allow various features of the subject to be seen by the range cameras, prevent incorrect meshing, and be comfortable for the person being scanned. Other range camera configurations may allow or necessitate other body poses.

Sensor Timing and Ordering

Sensor timing is affected by several constraints, including range camera frames per second and range noise/accuracy. Inaccurate range measurements may in some embodiments necessitate taking the average or taking the median of depth or RGB values of multiple range images from a particular camera or multiple cameras. Additionally, it is important to note that increased accuracy and precision comes at a cost of longer scan time, and a longer scan time increases the risk of a human subject, in one embodiment, changing their posture or moving their body. By way of example and not by limitation, one embodiment captures 10 frames per range camera, but other embodiments may capture fewer or greater number of frames per range camera. In another embodiment, the number of frames captured by each range camera could vary, depending on the camera.

One consequence of using multiple range cameras that rely on projected patterns to acquire range data is that different cameras may interfere with each other if their fields of view overlap each other, resulting in one or more range cameras attempting to capture data of the same region at the same time, resulting in interference and therefore missing range data. This necessitates a scan order, where individual range cameras or groups of range cameras are turned on and off sequentially or within some timing of each other. Because range camera interference is dependent on relative placement to each other, the timing and ordering scheme used for an embodiment may be dependent on each range camera's position and line of sight relative to each other.

Additionally, turning on/off the range cameras may also require an amount of time. Therefore, in embodiments that utilize a scan order, the group of cameras first in the scan order is turned on prior to a scan of a subject. These cameras may also aid in positioning of the subject in the scan area.

Figure 37:
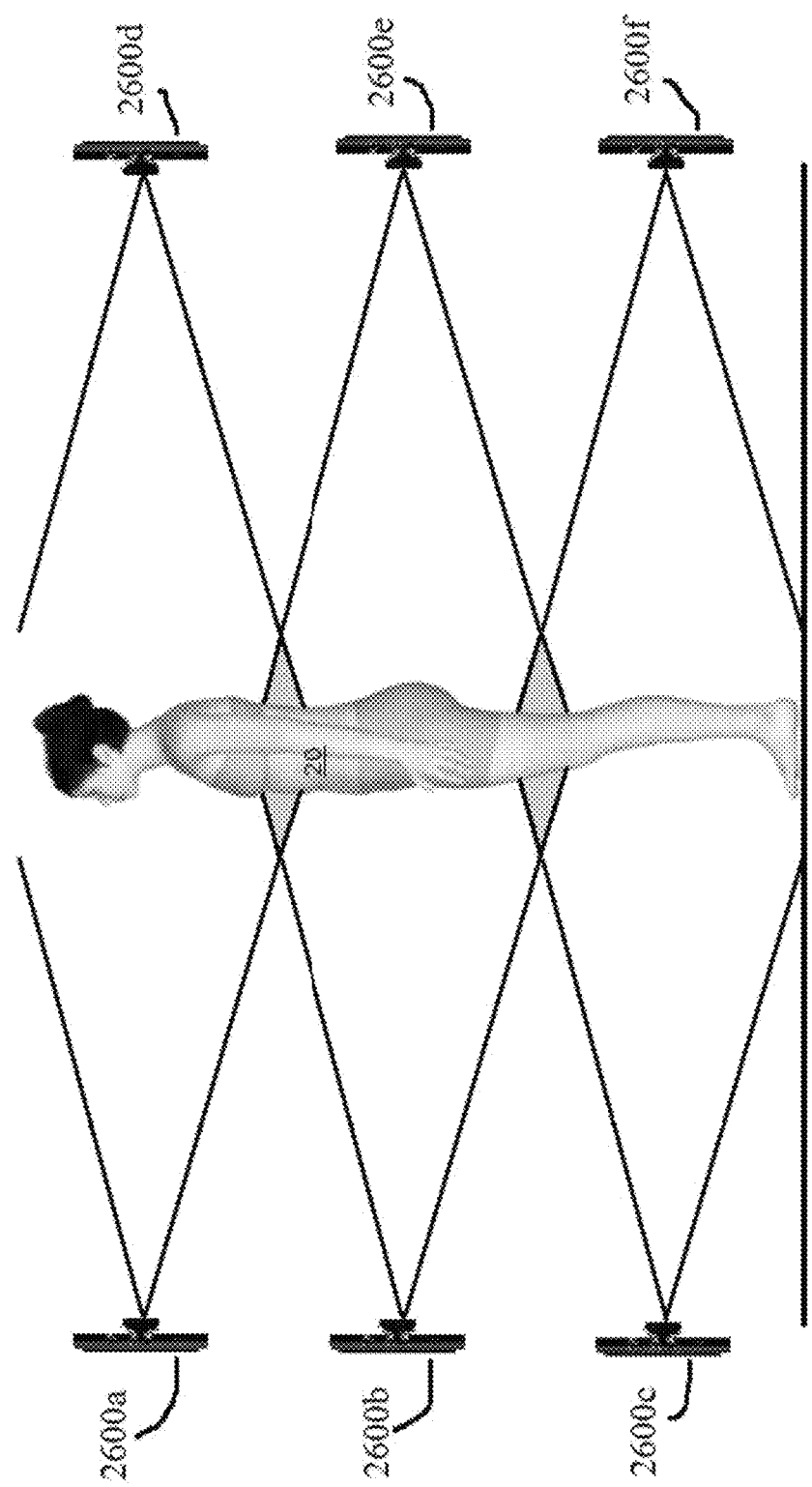
FIG. 37 is an illustration of a sample six range camera configuration for a scanner according to one embodiment.

By way of example and not by limitation, with reference to FIG. 37, in one embodiment, a range camera configuration using six range cameras is shown, where 3 range cameras each are mounted on two axes. Note that range camera 2600b has overlap on the surface of subject 20 with range cameras 2600a and 2600c. Likewise, range camera 2600e has overlap on the surface of subject 20 with range cameras 2600d and 2600f. Range cameras 2600a, 2600b, and 2600c do not interfere with range cameras 2600d, 2600e, and 2600f because different body surfaces are within the respective range camera groups' fields of view. In this embodiment, the scan order is such that range cameras 2600a, 2600c, and 2600e are turned on first. Once these range cameras finish collecting data, they are turned off and range cameras 2600b, 2600d, and 2600f are turned on. This scan order is designed to minimize both scan time and interference between range cameras.

Range Camera Registration

Figure 38:
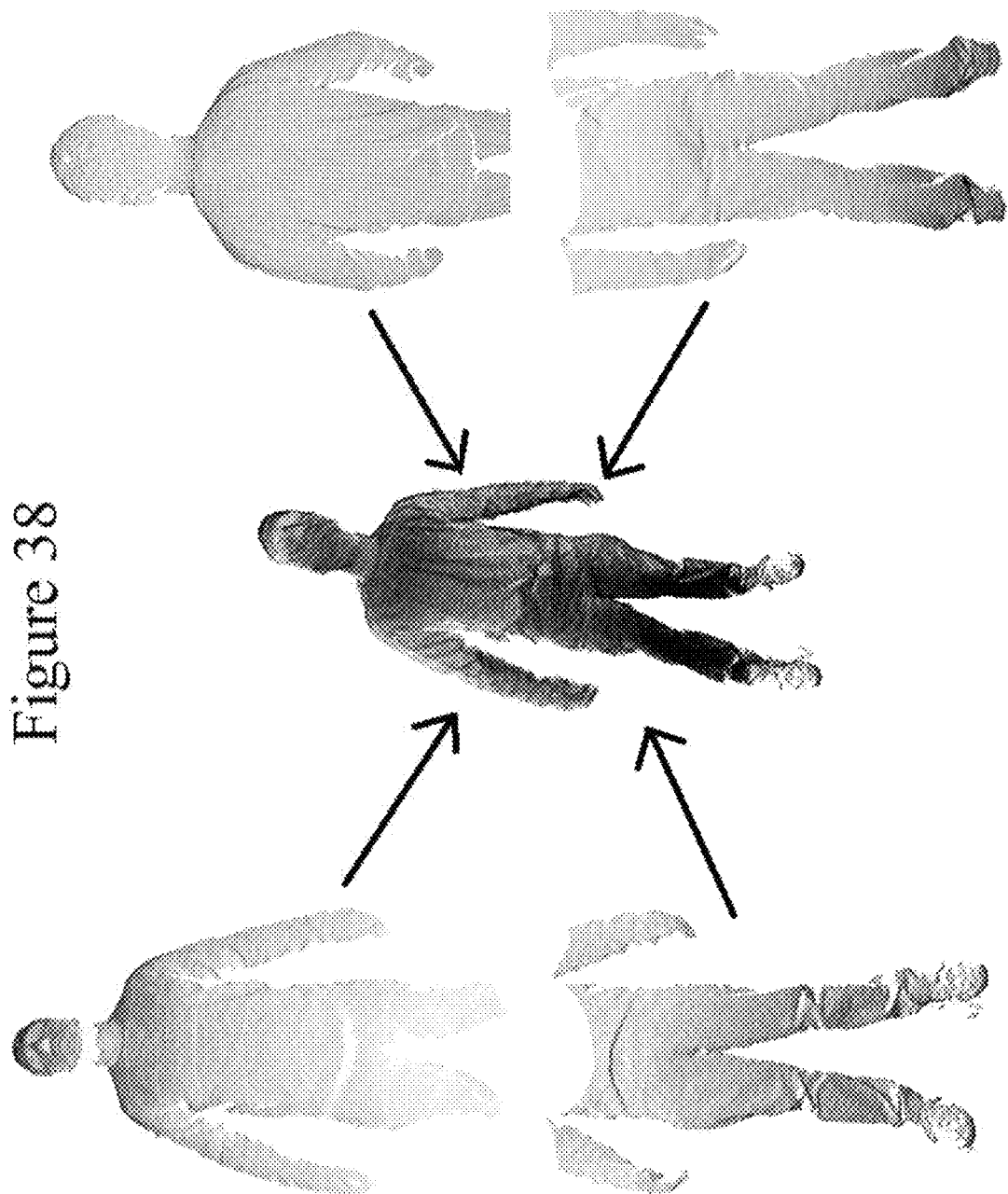
FIG. 38 is a diagrammatic illustration of how point clouds from four range cameras may be registered into a single, complete point cloud according to one embodiment.

The following section describes multiple methods for registering each range camera's point cloud into a common coordinate system, which may be one of the range camera's coordinate systems or any other coordinate system, effectively aligning together the point clouds from each range camera. Registration into a common coordinate system may be required to generate a complete point cloud of a subject. FIG. 38 illustrates how point clouds from four range cameras may be registered into a single, complete point cloud.

In one embodiment, each range camera's point clouds are registered via an iterative closest point (ICP) algorithm, known to those skilled in the art of machine vision. An initial estimate of the parameters required to register a range camera point cloud to another, hereinafter referred to as transformation, may be determined by the range camera configuration described above. Each pair-wise transformation may then be refined using the ICP algorithm, and the refined transformation data may be saved for future body scans. ICP may be used, for example, where there is sufficient overlap between each camera's point cloud. ICP may also be used in combination with other methods. ICP is described in detail in A Method for Registration of 3-D Shapes by Besl & McKay, which appears in IEEE Transactions on Pattern Analysis and Machine Intelligence, vol. 14, no. 2, pp 239-256, February 1992.

Figure 39:
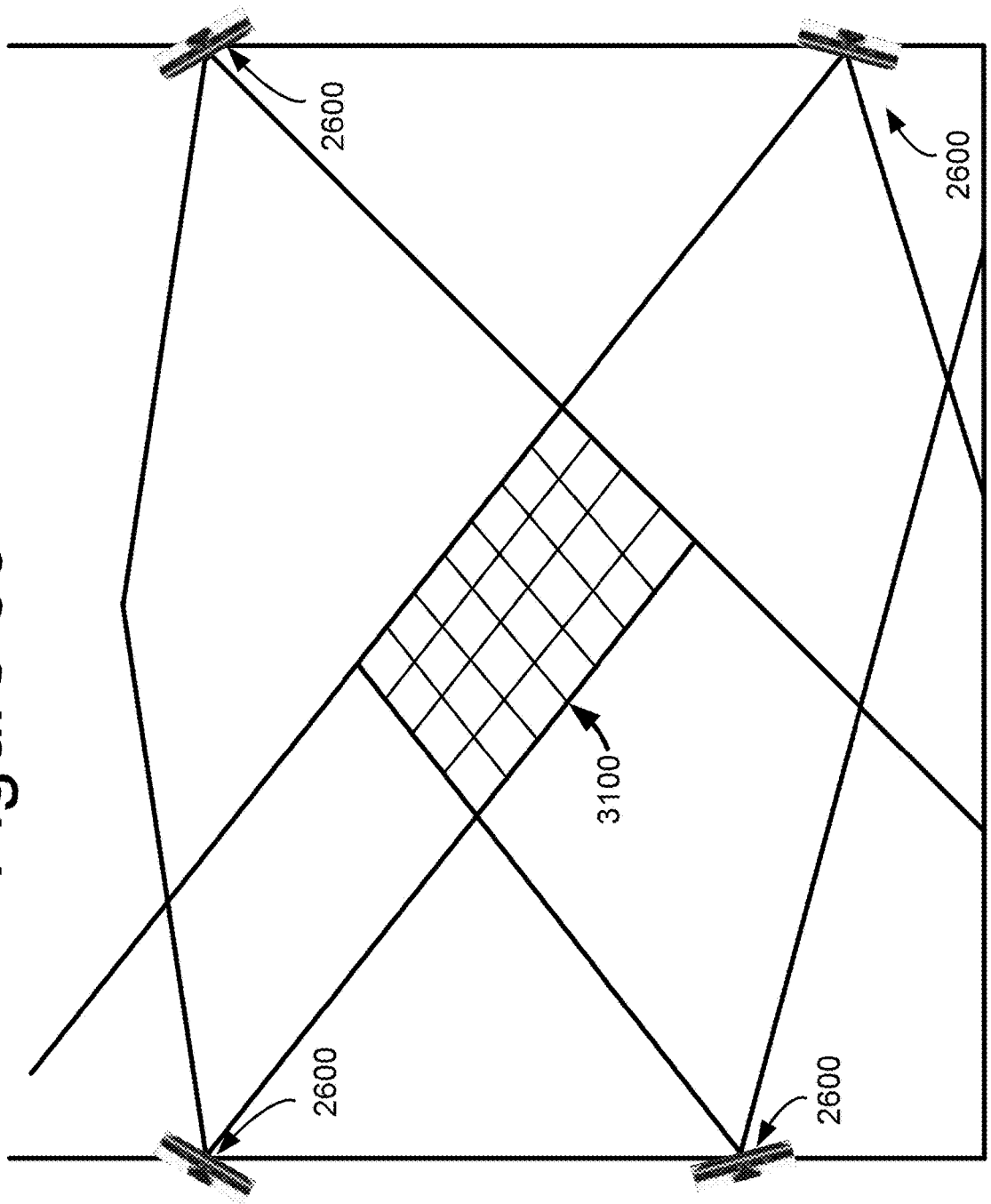
FIG. 39 is a diagrammatic illustration showing where a calibration assembly may be placed for a scanner.
Figure 40:
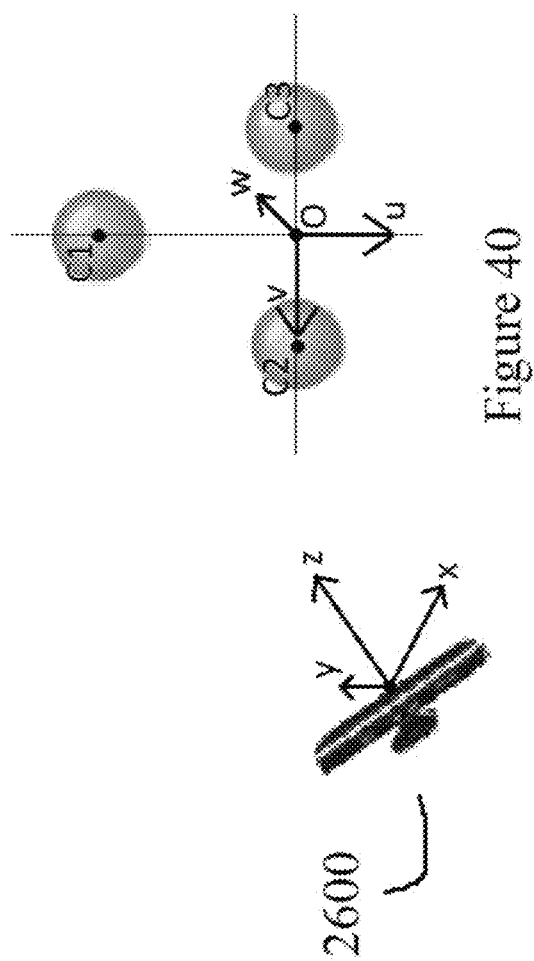
FIG. 40 is a diagrammatic illustration of an calibration assembly for creating a transformation matrix according to one embodiment.

In other embodiments, one or more objects, possibly in a predefined configuration. By way of example and not by way of limitation, the objects could be a triangular arrangement. The predefined configuration will be referred to herein as a calibration assembly, which may be used to facilitate registration. With reference to FIG. 39, a calibration assembly is positioned such that the objects that make up a calibration assembly, hereinafter referred to as calibration objects, are within the intersection 3100 of the fields of view of all range cameras 2600. Scans may be taken of the objects, and the data processed in such a way to determine a transformation from a range camera's coordinate system to a coordinate system common to the registered point clouds, hereinafter referred to as global coordinate system. It is known to those skilled in the art of computer graphics that such a transformation may be determined by defining the origin and axes of a global coordinate system in terms of a range camera's coordinate system. Also known to those skilled in the art of computer graphics, a fully defined coordinate system may require one common point, hereinafter referred to as an origin point, and two or more non-collinear vectors, hereinafter referred to as calibration vectors, all of which may be determined from a minimum of three common points, hereinafter referred to as calibration points. By way of example and not by limitation, with reference to FIG. 40, a transformation, in matrix form, from a coordinate system (x, y, z) of a range camera 2600 to a global coordinate system (u, v, w) centered at origin point O, may be determined if orthogonal vectors u=(ux, uy, uz), v=(vx, vy, vz), and w=(wx, wy, wz), as well as origin point O=(Ox, Oy, Oz) are known, with the subscripts x, y, and z denoting coordinates in a range camera's coordinate system. The transformation matrix T that transforms a point P=($p_x$, $p_y$, $p_z$) into global coordinates ($p_u$, $p_v$, $p_w$) may be defined in the following way, with • denoting a vector dot product:

$$T = \begin{bmatrix} u_x & u_y & u_z & -O \cdot u \\ v_x & v_y & v_z & -O \cdot v \\ w_x & w_y & w_z & -O \cdot w \\ 0 & 0 & 0 & 1 \end{bmatrix} \text{ s.t. } \begin{bmatrix} p_u \\ p_v \\ p_w \\ 1 \end{bmatrix} = T \begin{bmatrix} p_x \\ p_y \\ p_z \\ 1 \end{bmatrix}$$

Figure 41:
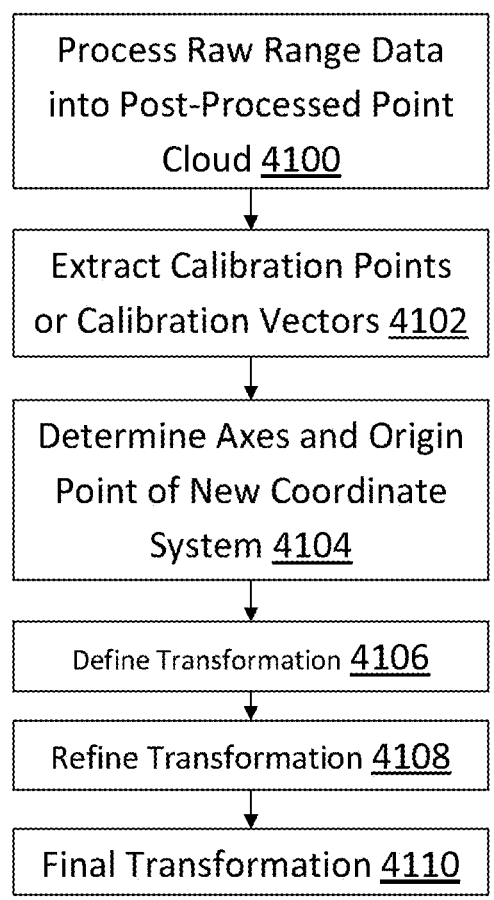
FIG. 41 is a flow diagram that illustrates the steps performed in one embodiment of a process of calibration, which may be performed by each range camera and utilizing such a calibration assembly.

In embodiments where a calibration assembly is used, a calibration procedure may be required prior to scanning a subject. With reference to FIG. 41, a flow diagram illustrates the steps performed in one embodiment of a process of calibration, performed by each range camera and utilizing such a calibration assembly. In step 4100, the raw range data obtained from a scan of the calibration assembly is converted into point clouds, one for each calibration object in the calibration assembly. In step 4102, calibration points and/or calibration vectors are determined from the point clouds obtained from step 4100. In step 4104, an origin point and set of orthogonal vectors of a global coordinate system are determined in a range camera's coordinates. In step 4106, a transformation from a range camera's coordinate system to a global coordinate system is determined. Optionally, in step 4108, the transformation may be refined further. The process described above produces a final transformation 4110. What follows are descriptions of multiple calibration assemblies, multiple methods for extracting calibration points and/or calibration vectors from a range image, multiple methods of defining a coordinate system from calibration points and/or calibration vectors, and multiple methods of defining and refining a transformation from range camera coordinates into global coordinates.

Figure 43:
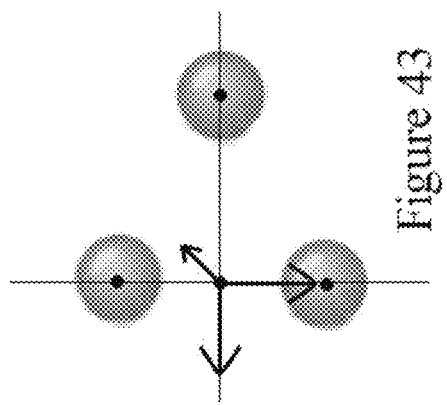
FIG. 43 is a diagrammatic illustration of another embodiment of a calibration assembly.
Figure 42:
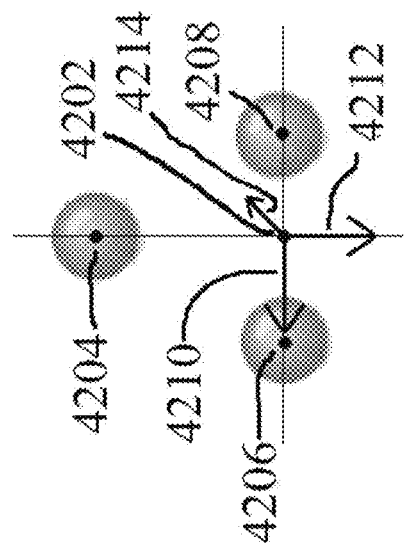
FIG. 42 is a diagrammatic illustration of a calibration assembly according to one embodiment.

With reference to FIG. 42, in one embodiment, a calibration assembly may comprise spherical objects arranged in a triangle whose base is parallel with the ground plane. Three calibration points may be found by determining the three sphere centers, determined in step 4102 of FIG. 41. With reference back FIG. 41, in an example of further detail of the process of step 4104, an origin point 4202 may be defined as the projection of a calibration point 4204 onto the line formed by the other calibration points 4206 and 4208. Then a vector 4210 may be defined as extending from 4208 to 4206, a perpendicular vector 4212 may be defined as extending from 4204 to 4202, and a third vector 4214, perpendicular to both vectors 4210 and 4212, may be defined as the cross product of 4210 and 4212. Therefore an origin 4202, as well as three orthogonal vectors obtained by normalizing the vectors 4210, 4212, and 4214, may define a coordinate system. By way of example and not by limitation, other embodiments may use a different origin point (the average of three calibration points or a calibration point itself) and/or different perpendicular vectors relative to the calibration points (the normal to the plane containing the calibration points, or the cross product of two non-collinear vectors). With reference to FIG. 43, in another embodiment, the aforementioned triangle of spherical objects may be placed on its side, or in some other orientation.

Figure 44:
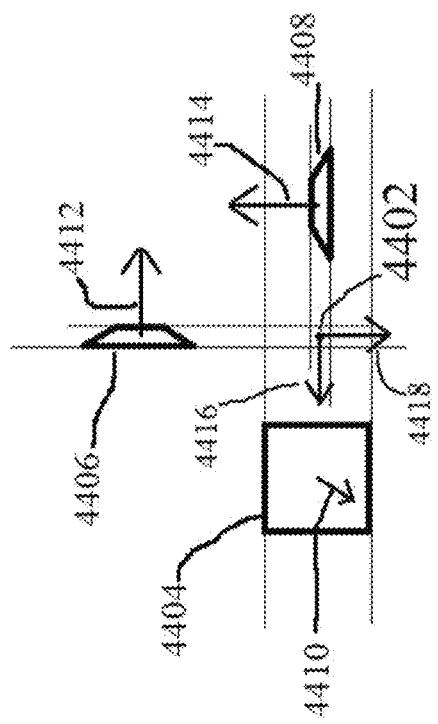
FIG. 44 is a diagrammatic illustration of a calibration assembly using flat plates according to another embodiment.

With reference back to FIG. 41, in another example of further detail of the process of step 4102, in some embodiments, planar objects of any shape may be used in a calibration assembly, where calibration points may be determined by the 2D center or some other feature relative to the planar surface. In some embodiments, normal vectors may be estimated from planar objects of any shape by fitting a plane to the object's point cloud. Plane fitting is a method known to those skilled in the art of machine vision. These vectors may then be used directly to define a coordinate system. With reference to FIG. 44, in one embodiment, an origin point 4402 may be determined by the intersection of plane equations fitted to planar calibration objects 4404, 4406, and 4408 with non-collinear normal vectors 4410, 4412, and 4414, respectively. Additionally, the cross product of two normal vectors, by way of example and not by limitation, 4410 with 4414, may be taken to obtain the vector 4416, and the cross product of 4410 with 4416 may be taken to define vector 4418. In this manner the origin point 4402 and the three vectors 4410, 4416, and 4418 define a coordinate system.

In some embodiments, a combination of shapes and other objects may be used in a calibration assembly. Some embodiments may use poles, rods, strings, or some other method for holding the calibration objects from the bottom, from the sides, or some other position. Some embodiments may use a combination of calibration assemblies and methods described above.

Figure 45:
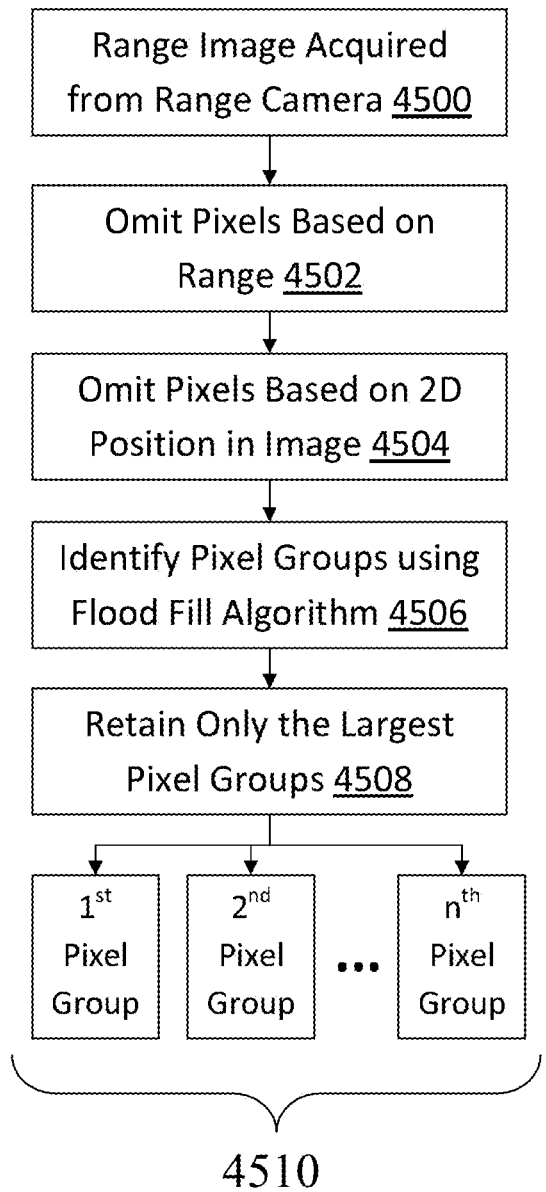
FIG. 45 is a flow diagram illustrating steps performed in one embodiment for converting raw range data into pixel groups originating from calibration objects.
Figure 46:
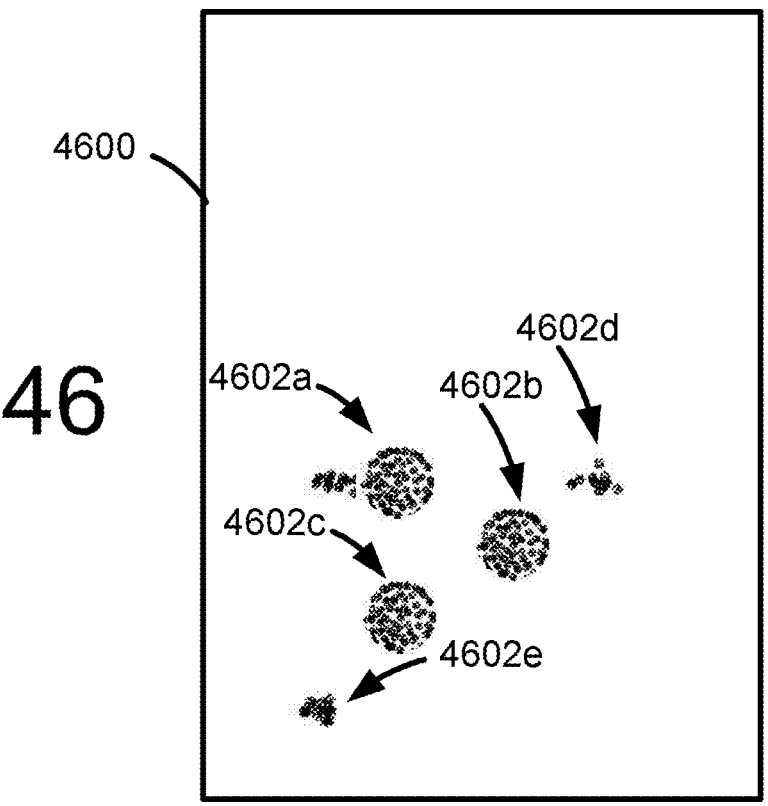
FIG. 46 is a sample of images captured by range cameras during calibration according to one embodiment.

With reference to FIG. 45, a flow diagram illustrates in detail the steps performed in one embodiment of a process of converting raw range data into pixel groups originating from calibration objects. Beginning with step 4500, a 2D range image of calibration objects is acquired from a range camera. In step 4502, a cutting plane may be used to remove pixels originating from the background, which by way of example and not by limitation may consist of the floor, walls, and other range cameras. In step 4504, pixels may be omitted based on location in the 2D range image, again to remove pixels originating from the background, as well as pixels originating from structures which hold the calibration objects. In step 4506, the surviving pixels are subjected to a flood fill algorithm, known to those skilled in the art of computer graphics, to cluster (group together) pixels that may originate from the same object. With reference to FIG. 46, range image 4600 may contain, by way of example and not by limitation, multiple pixel groups 4602*a*, 4602*b*, 4602*c*, 4602*d*, and 4602*e*. Pixel groups 4602*a*, 4602*b*, and 4602*c* represent calibration objects, while pixel groups 4602*d* and 4602*e* represent, by way of example and not by limitation, structures that hold the calibration objects, background objects not previously filtered out, or range camera artifacts. In the case where pixels from multiple calibration objects are adjacent, one embodiment may call for further segmentation based on range, but this step may not be required if the calibration objects are at least one pixel apart. In step 4508, also with reference to FIG. 46, to filter out pixel groups 4602*d* and 4602*e* originating from, for instance, background noise or structures that hold the calibration objects, the pixel groups that contain the most pixels, 4602*a*, 4602*b*, and 4602*c*, collectively 4510 in FIG. 45, are retained. The number of pixel groups retained equals the number of calibration objects, and the remaining pixel groups 4602*d* and 4602*e* are discarded.

Figure 47:
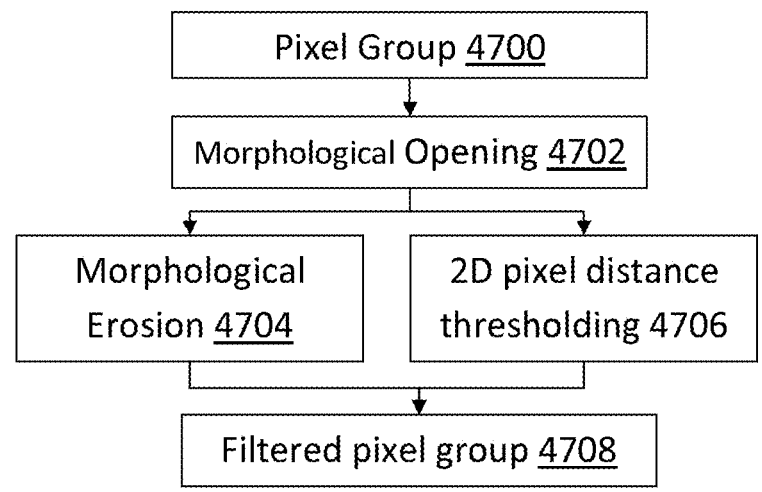
FIG. 47 is a flow diagram illustrating the steps performed in one embodiment of a process of filtering out unwanted pixels from a pixel group of FIG. 45 according to one embodiment.
Figure 48:
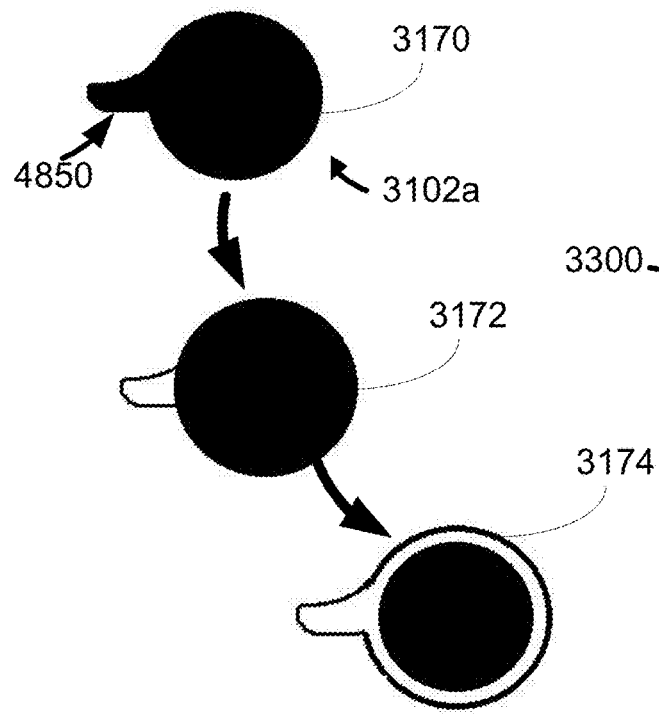
FIG. 48 is an illustration showing elimination of pixels from a pixel group of FIG. 45 according to one embodiment.

With reference to FIG. 47, a flow diagram illustrates the steps performed in one embodiment of a process of filtering out unwanted pixels from a pixel group 4700, which is one of the pixel groups 4510 from FIG. 45. In step 4702, with reference to FIG. 48, the pixel group 3170 may contain pixels 4850 originating from structures that hold the calibration object (which may be a finger-shaped region). The pixels 4850 may be eliminated by performing a morphological opening operation, known to those skilled in the art of image processing, resulting in pixel group 3172. In either step 4704, or step 4706, inaccurate range measurements at the edge of the calibration object may also be eliminated, resulting in pixel group 3174. In step 4704, a morphological erosion operation, known to those skilled in the art of image processing, may be performed on pixel group 3172. Alternatively, in step 4706, edge pixels may be removed by finding the 2D centroid pixel and removing those greater than a specified distance or a specified distance percentile, by way of example and not by limitation, 80%. This yields one filtered 2D pixel group 4708 for each calibration object, which may be converted into a 3D point cloud for each calibration object, as previously referenced in FIG. 29.

Figure 51:
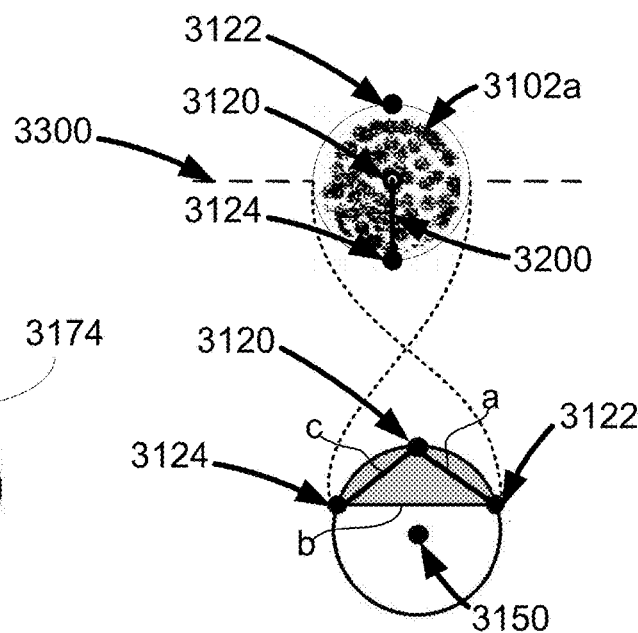
FIG. 51 is another diagram further illustrating the method for determining the distance from a range camera to a center of a calibration object according to the embodiment of FIG. 50.
Figure 50:
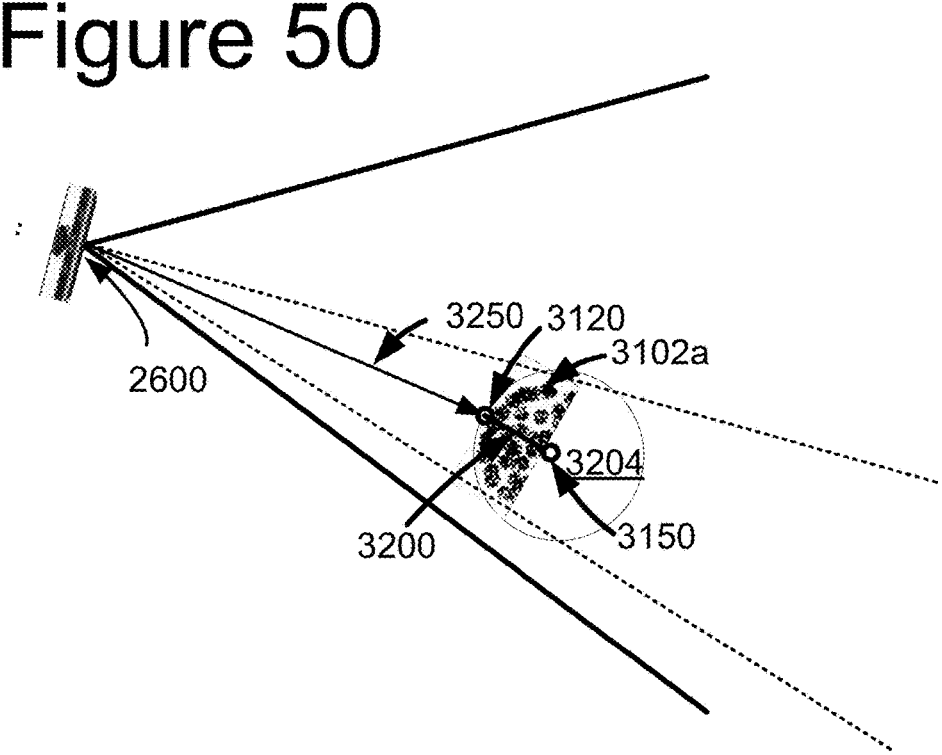
FIG. 50 is a diagram illustrating a method for determining the distance from a range camera to a center of a calibration object according to one embodiment.
Figure 49:
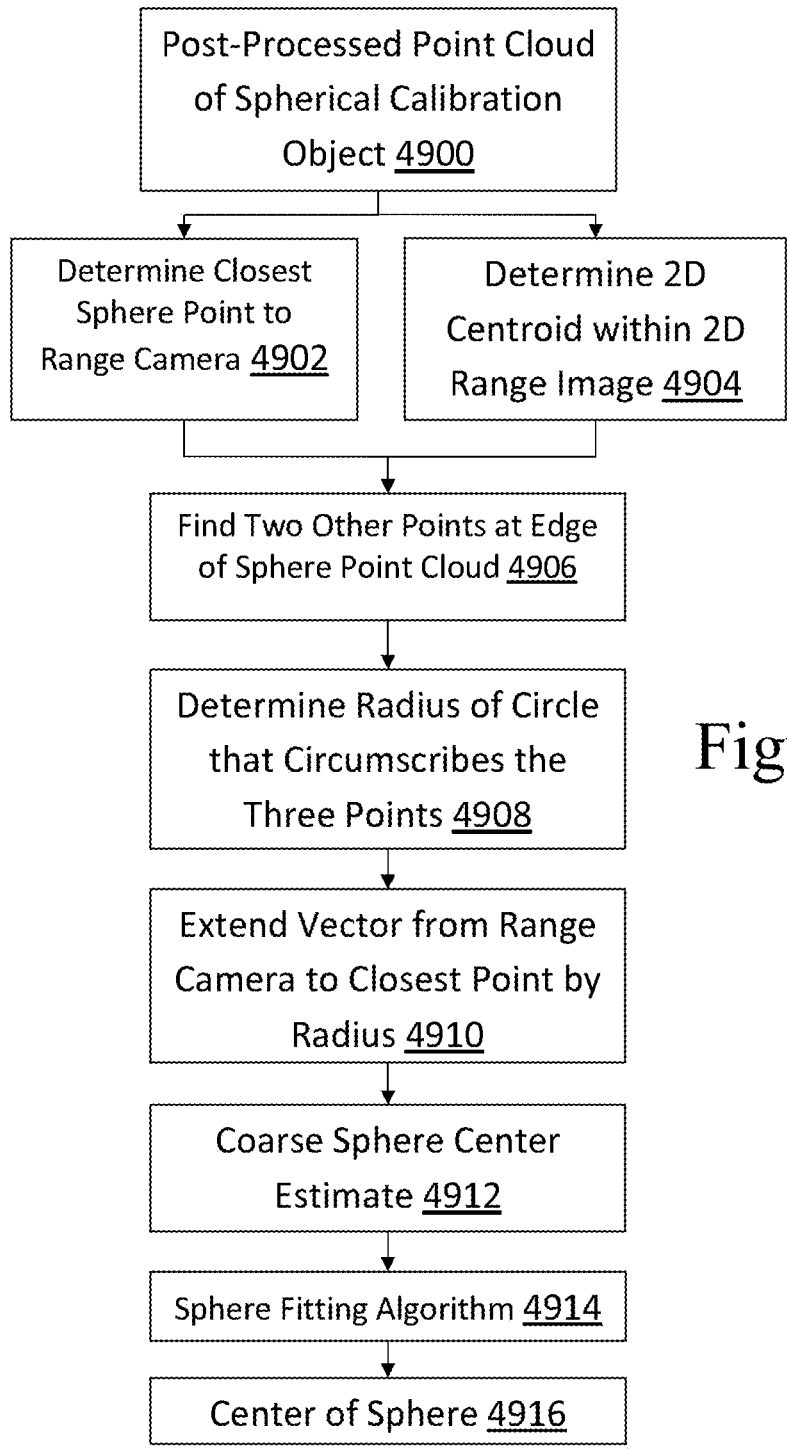
FIG. 49 is a flow diagram illustrating the steps performed in a process of determining a calibration point for embodiments utilizing spherical calibration objects according to one embodiment.

One or more calibration points and/or vectors may then be extracted from each object's point cloud. With reference to FIG. 49, a flow diagram illustrates in detail the steps performed in a process of determining a calibration point for embodiments utilizing spherical calibration objects. In this embodiment, the 3D center of a sphere, estimated from a point cloud 4900 which may be less than a hemisphere, is used as a calibration point. In step 4902, with reference to FIGS. 50 and 51, the sphere center may be initially coarsely estimated by finding the point 3120 on the sphere 3204 closest to the range camera 2600 (based on, by way of example and not by limitation, raw range or an average of nearby points). As an alternative, in step 4904, the 3D point corresponding to the 2D centroid pixel of the calibration object in the 2D range image may be used as point 3120. In step 4906, edge points 3122 and 3124 are determined by, in the 2D range image, stepping out vertically or horizontally from the 2D pixel corresponding to point 3120 to the edge of the pixel group 3102*a*. The 3D point corresponding to each pixel is taken to be points 3122 and 3124, respectively. In step 4908, three distances a, b, and c between points 3120, 3122, and 3124 are used to calculate the radius 3200 of the circle that circumscribes points 3120, 3122, and 3124 via the following equation, known to those skilled in the art of mathematics:

$$\text{radius} = \frac{abc}{\sqrt{2a^2b^2 + 2b^2c^2 + 2c^2a^2 - a^4 - b^4 - c^4}}$$

In step 4910, the vector from the origin of range camera 2600 to point 3120 may then be extended by the radius estimate, which yields a coarse sphere center estimate 4912. In step 4914, this estimate 4912 may then be used as an initial guess to a nonlinear least squares least fit algorithm, known to those skilled in the art of computer graphics, to attain a more accurate estimate of the sphere center 4916.

In reference back to FIG. 41, in step 4102, in embodiments utilizing planar objects in the calibration assembly, a plane (and normal vector) may be fit to a point cloud (originating from a planar calibration object) using a linear least squares method, known to those skilled in the art of machine vision and other mathematical arts. In one embodiment, the normal vector to a plane may be used as a calibration vector. In one embodiment, the calibration assembly may be designed such that the intersection of three planes may be used as a calibration point.

In reference back to FIG. 41, in step 4108, in some embodiments, camera resolution, noise, or other constraints may necessitate further processing to attain accurate transformations from each range camera into the aforementioned global coordinate system. In embodiments where there is enough overlap between adjacent cameras' point clouds, ICP may be used to refine the transformations. Another embodiment utilizes an ICP-like algorithm to match a point cloud to an ideal model representing the position and pose of the objects in the calibration assembly.

In reference back to FIG. 41, in step 4108, some embodiments may require a specific global coordinate system. For instance, the origin may be located on the ground between the subject's feet and/or the vertical axis may be perpendicular to the ground plane. In such embodiments, additional processing may be needed to transform the subject point cloud from the aforementioned global coordinate system (relative to the calibration assembly) into a specified coordinate system, particularly if it is defined by objects or features not visible to all range cameras. In embodiments that require ground plane detection, points originating from the ground may be grouped together, and a plane may be fitted to these points, similar to the method for extracting normal vector information from planar calibration objects described above.

Meshing

Figure 52:
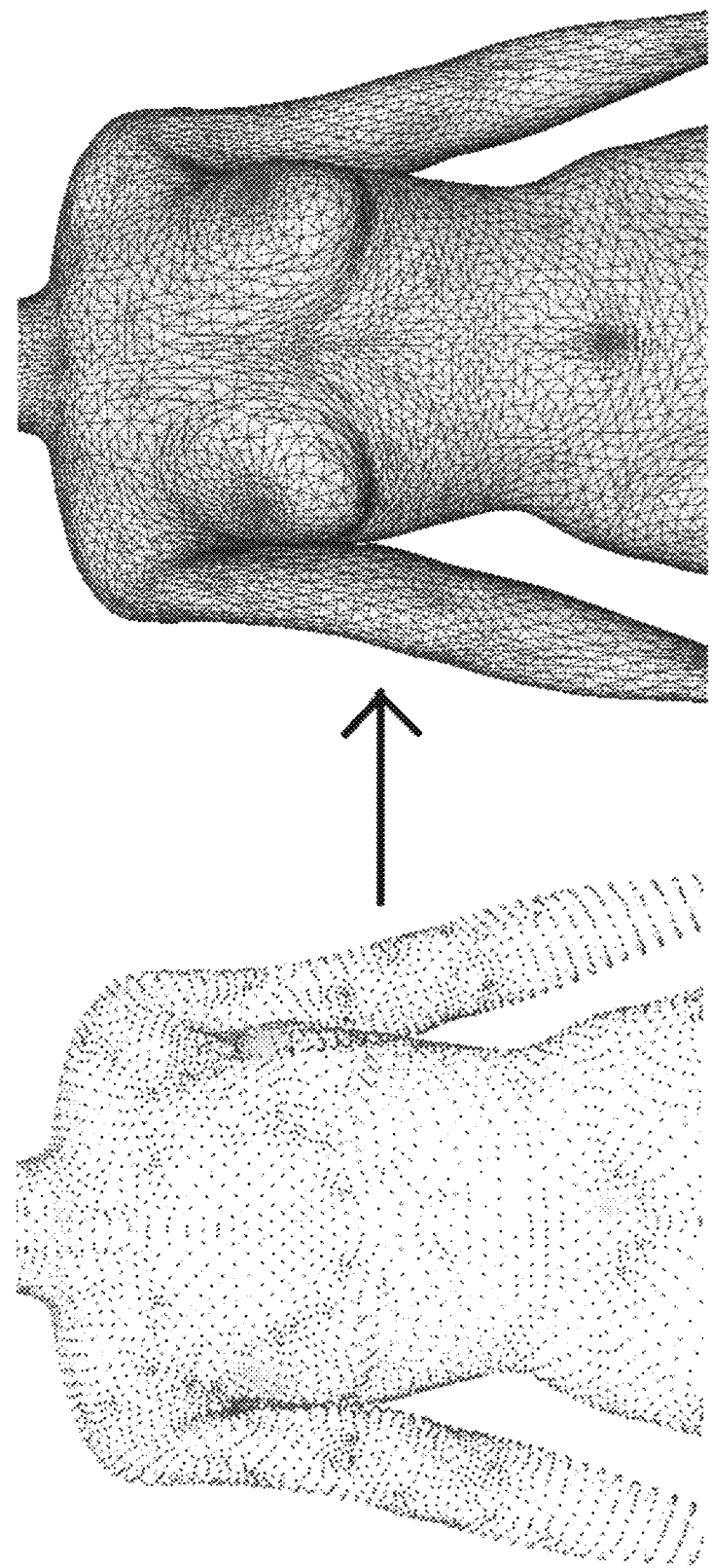
FIG. 52 illustrates a conversion of a registered point cloud into a triangular mesh for virtual try-on according to one embodiment.
Figure 53:
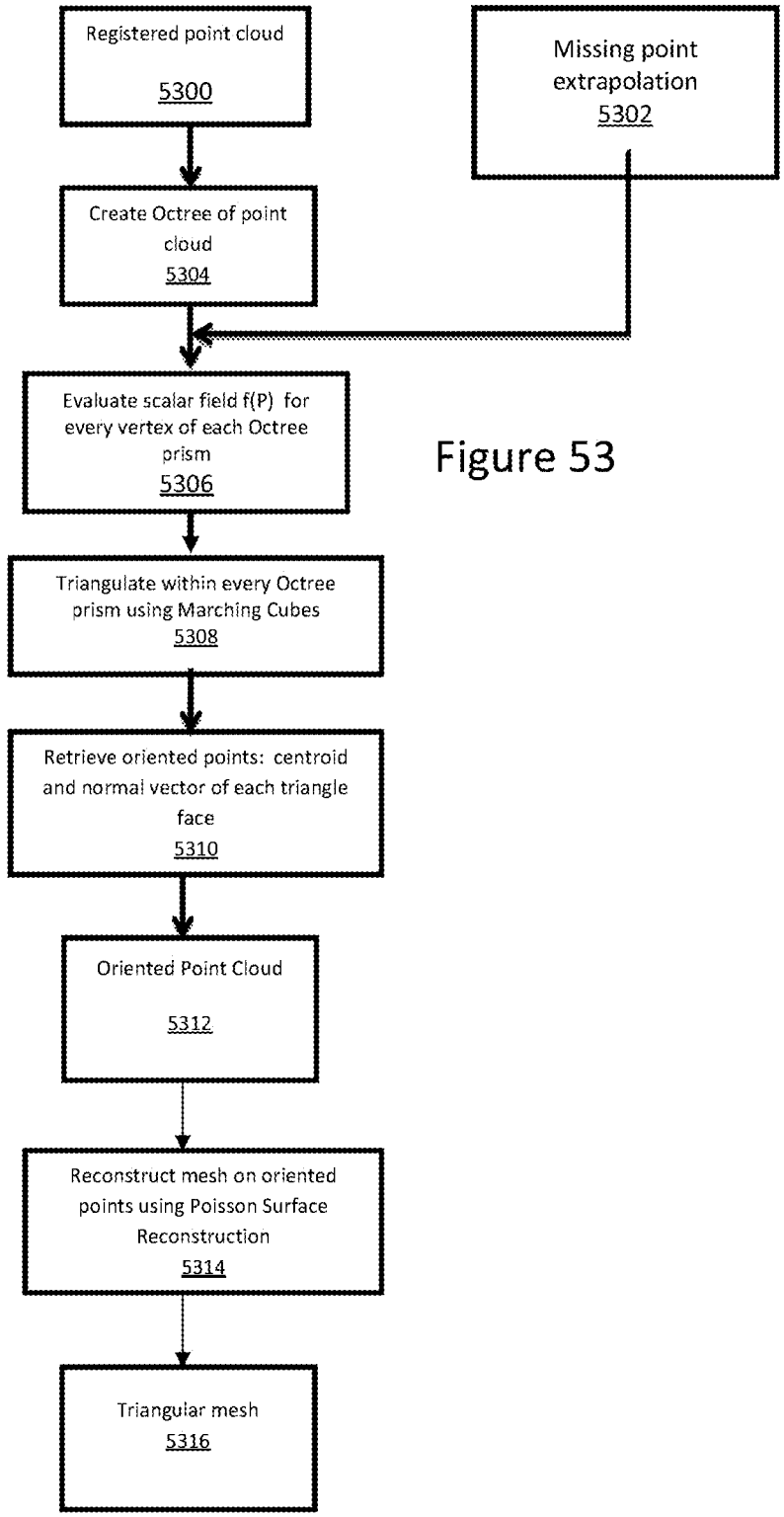
FIG. 53 is a flow diagram illustrating steps performed in a method of point cloud preprocessing prior to PSR according to one embodiment.

In one embodiment, a method based on Poisson surface reconstruction (PSR), known to those skilled in the art of computer graphics, is used to, with reference to FIG. 52, convert a registered point cloud into a triangular mesh needed for virtual try-on. PSR is an implicit surface (also known as iso-surface) extraction method, where an implicit surface is defined as a contour of a continuous scalar field in 3D space. PSR is described in detail in Poisson Surface Reconstruction by Kazhdan, Bolitho, and Hoppe, published in the Proceedings of the Fourth Eurographics Symposium on Geometry Processing, pp 61-70, 2006. With reference to FIG. 53, a flow diagram, illustrating steps performed in a method of point cloud preprocessing prior to PSR, is shown according to one embodiment, where a registered point cloud 5300 is transformed into a point cloud where each point has associated with it a surface normal, hereinafter referred to as an oriented point cloud 5312. A detailed description of this point cloud preprocessing follows.

Figure 54:
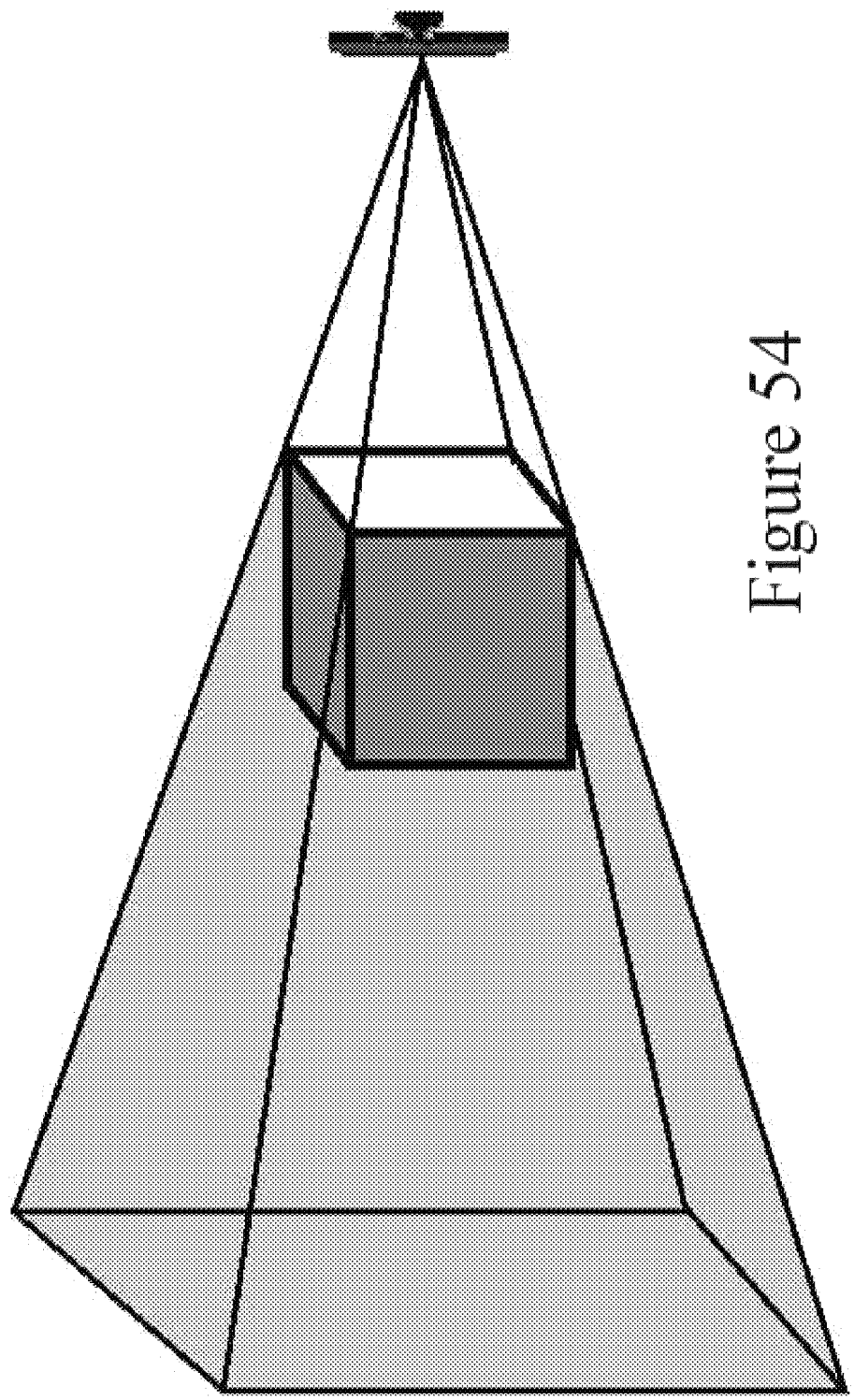
FIG. 54 illustrates the shadow volume made by an object in the field of view of a range camera.

In step 5306, in some embodiments, a scalar field f(P) is utilized, which may or may not be the same as that used in PSR. In one embodiment, the scalar field is defined such that a point (not necessarily part of the point cloud) inside the body is assigned a different value than a point outside the body, and thus calculating the value of the scalar field at a point reduces to determining whether a point is inside the body. One embodiment uses the concept of shadow volume, known by those skilled in the art of computer graphics, with each range camera analogous to a light source and the range camera's line of sight analogous to light rays. FIG. 54, by way of example and not by limitation, shows the shadow volume made by an object in the field of view of a range camera. With respect to a camera's 2D range image, a point P transformed into a camera's 2D pixel coordinate system is considered within the camera's shadow volume if: (1) P's pixel location has a valid corresponding range value in the 2D range image, and (2) P's range value is greater than that of the corresponding value in the 2D range image. In other words, P is within the shadow volume if it is behind the surface defined by the 2D range image. Then P is considered inside the body if, for all cameras whose field of view contains P, P is within each camera's shadow volume. In one embodiment, f(P) may be determined by applying the above method to multiple points (P1 . . . Pn) in the neighborhood of P, and f(P) takes on the value of a weighted average of f(P1) . . . f(Pn). In one embodiment, f(P) may be defined in terms of distance away from the surface defined by each range camera's 2D range images. In one embodiment, f(P) may defined such that it is guaranteed to be continuous. An embodiment may take on characteristics of some, all, or none of the embodiments outlined in this paragraph.

In step 5302, in one embodiment, due to, for instance, missing depth values in the raw 2D range images, perspective differences between cameras, and inconsistent range/pixel resolution, the 2D range images used for determining shadow volume of each range camera are constructed from points originating from multiple cameras. In another embodiment, the aforementioned range images are constructed from the entire point cloud of the subject. In either embodiment, 2D range image construction is performed by transforming points into each camera's 2D projective coordinate system and, for each pixel, using the smallest range value.

In step 5304, in one embodiment, to obtain a set of oriented points, also known as an oriented point cloud, which may be used as input to PSR, the point cloud of the subject is inserted into an octree (also oct-tree) data structure, known to those skilled in the art of computer graphics. The octree assigns a rectangular prism volume to each data point. A detailed description of the octree is contained within Oct-trees and their use in representing three-dimensional objects by Jakins & Tanimoto, published in Computer Graphics and Image Processing, Volume 14, Issue 3, November 1980, pp 249-270. Then, in step 5306, f(P) for each of the eight vertex points of the rectangular prism are determined, after which, in step 5308, the marching cubes algorithm, known to those skilled in the art of computer graphics, may be used to triangulate within the rectangular prism. A detailed description of the marching cubes algorithm is contained within Marching cubes: A high resolution 3D surface construction algorithm by Lorensen & Cline, published in ACM SIGGRAPH Computer Graphics, Volume 21, Issue 4, July 1987, pp 163-169. Then, in step 5310, every centroid of each triangle face is retained along with its corresponding normal vector, defined as the normal to the triangle face in a consistent direction. In one embodiment, this direction is inside the body, while in another embodiment, this direction is outside the body. The retained oriented point cloud 5312, used as input to PSR 5314, may contain a different set of points than the original point cloud 5300 of the subject. The output of PSR is a triangular mesh 5316. In other embodiments, the marching cubes algorithm alone may generate a triangular mesh.

Figure 55:
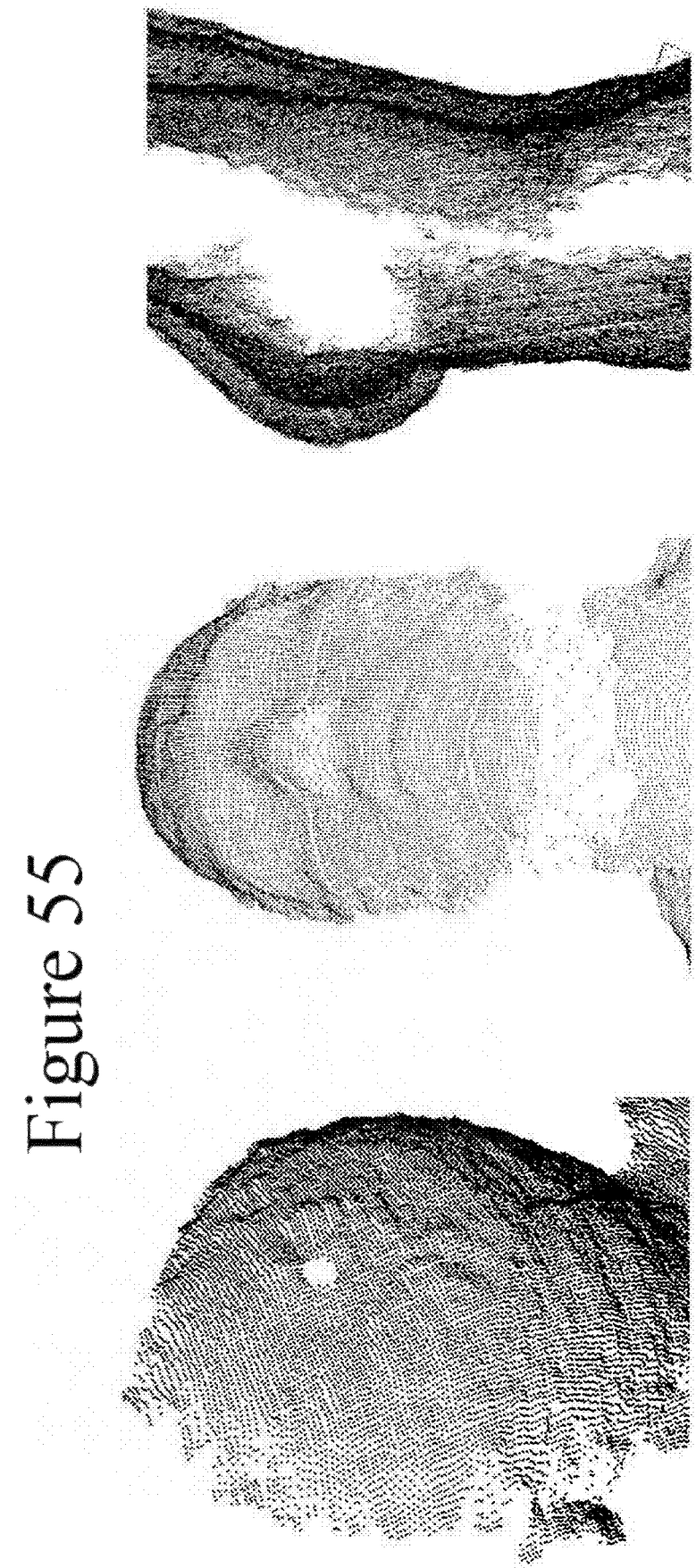
FIG. 55 shows examples of anomalies in a point cloud.

In some embodiments, parts of the body surface may be sparsely represented by points in the point cloud of the subject and/or there may be gaps in the point cloud. FIG. 55 shows examples of such anomalies in a point cloud. In such embodiments, the aforementioned octree data structure is modified intermittently while the aforementioned marching cubes algorithm is performed on each node. If a leaf node (which, in an unmodified octree, would contain only one point from the point cloud of the scanned subject) has a tree depth less than a specified threshold (by way of example and not by limitation, common values for the aforementioned tree depth threshold are 8, 9, and 10, with a larger value denoting higher surface resolution) and generates at least one triangle as per the marching cubes method described above, the node (and its children fulfilling the same criteria) may be split and re-triangulated with marching cubes. A splitting operation on an octree consists of dividing the rectangular prism volume of the node into equally sized octants and creating a child node for each octant. Because centroids of triangles within each node volume, not necessarily the points in the original point cloud, are used as input to PSR, splitting an octree node according to the above criteria effectively fills in surface regions underrepresented by points in the original point cloud. In an alternative embodiment, the rectangular prism volume may be checked in lieu of the tree depth. In yet another embodiment, different parts of the body surface may use different threshold values and hence have different resolution.

In one embodiment, the oriented point cloud determined by marching cubes may be more dense than required. To save on processing time during PSR, this oriented point cloud may be thinned out based on a radius threshold. That is, for each oriented point, other oriented points within a distance threshold may be removed from the oriented point cloud.

In one embodiment, it may be desirable to smooth the surface of the triangular mesh created by PSR. By way of example and not by way of limitation, Laplacian smoothing, known to those skilled in the art of computer graphics, may be applied.

In one embodiment, since the processing of a node in an octree is independent of the processing of any sibling node, the above steps may be parallelized. This may result in significant runtime efficiency.

In one embodiment, elements of the preceding preprocessing steps may be merged with PSR. This can be done since PSR uses an octree data structure. By way of example and not by way of limitation, calculating f(P), using marching cubes triangulation to define surface normals, and/or splitting octree nodes during marching cubes may be performed on the same octree used by PSR.

The meshing method used in any embodiment may use elements from a combination of the embodiments described above.

Product Customization and Personalization

Most apparel produced and purchased today is built with standard grading or sizes conceived by the retailer, brand, or manufacturer. That sizing was pre-selected by the retailer, brand, or manufacturer using internal or published data on body shapes in various markets.

However, body scanning and subsequent measurement extraction paves the way for retailers, brands, and manufacturers to create a custom size for an individual. That custom size essentially reflects either a new draft of a digital or paper pattern that reflects the consumers body measurements and additional ease or fit requirements set by the consumer or retailer, brand, and manufacturer. In other cases, the custom size is simply an alteration of an existing size, that again, reflects the body measurements of the consumer.

The process of adjusting or automatically drafting a new customized digital pattern uses techniques that one skilled in the art of pattern making would easily recognize.

Additionally, a consumer may customize the decoration or design of a garment by selecting colors, textures, prints, and other artwork and placing it on any part of the garment. A user interface that runs on multiple platforms may provide the consumer the ability to customize the design of the apparel. The design process may occur on a 2-dimensional digital pattern displayed in the user interface, or a 3D rendering of the garment draped on an avatar. The avatar may be of the consumer with a simulated drape of the garment in a chosen or recommended size or a default of an avatar. If the design process occurred in 3D, using a 3D renderer or 3D images, the final design may then be translated back into the 2D geometry of the pattern including process-related elements necessary for garment production, including sewing allowance, bleed area for dying and other elements, and then be sent to a manufacturer for production.

The manufacturer may dye, print, and cut, in any order, depending on the technology the manufacturer has adopted, and then sew the final garment for delivery.

Automatic spreaders or manual spreaders may be used to lay fabric in preparation for cutting each individual piece of the customized garment.

Automatic cutting technology may be used to automatically cut each individual piece of the customized a garment. In another embodiment, manual cutters may be used in place of automatic cutting machines.

In another embodiment, wherein the customization is centered on only the design or decoration of the garment, but not the adjustment or automatic creation of the pattern, pre-cut pieces in various sizes may already be produced and kept as inventory.

Waterless printing and chemical free dyeing technology may be used to automatically print and dye the design of each piece already cut, or cut specifically for the consumer.

In another embodiment, pre sewn garments may be used and designs may be placed on the pre-sewn garments, often called blanks, using screen printing or sublimation printing technology.

The user interface may display the final design to the consumer and then enable them to purchase a garment before production takes place. In the case that automatic printing and dyeing technology is used to print and dye on-demand on each piece, and the pieces are cut on-demand, a retailer, brand and manufacturer could keep zero inventory, and thus, wait for an order or transaction from the consumer before beginning production.

Figure 56:
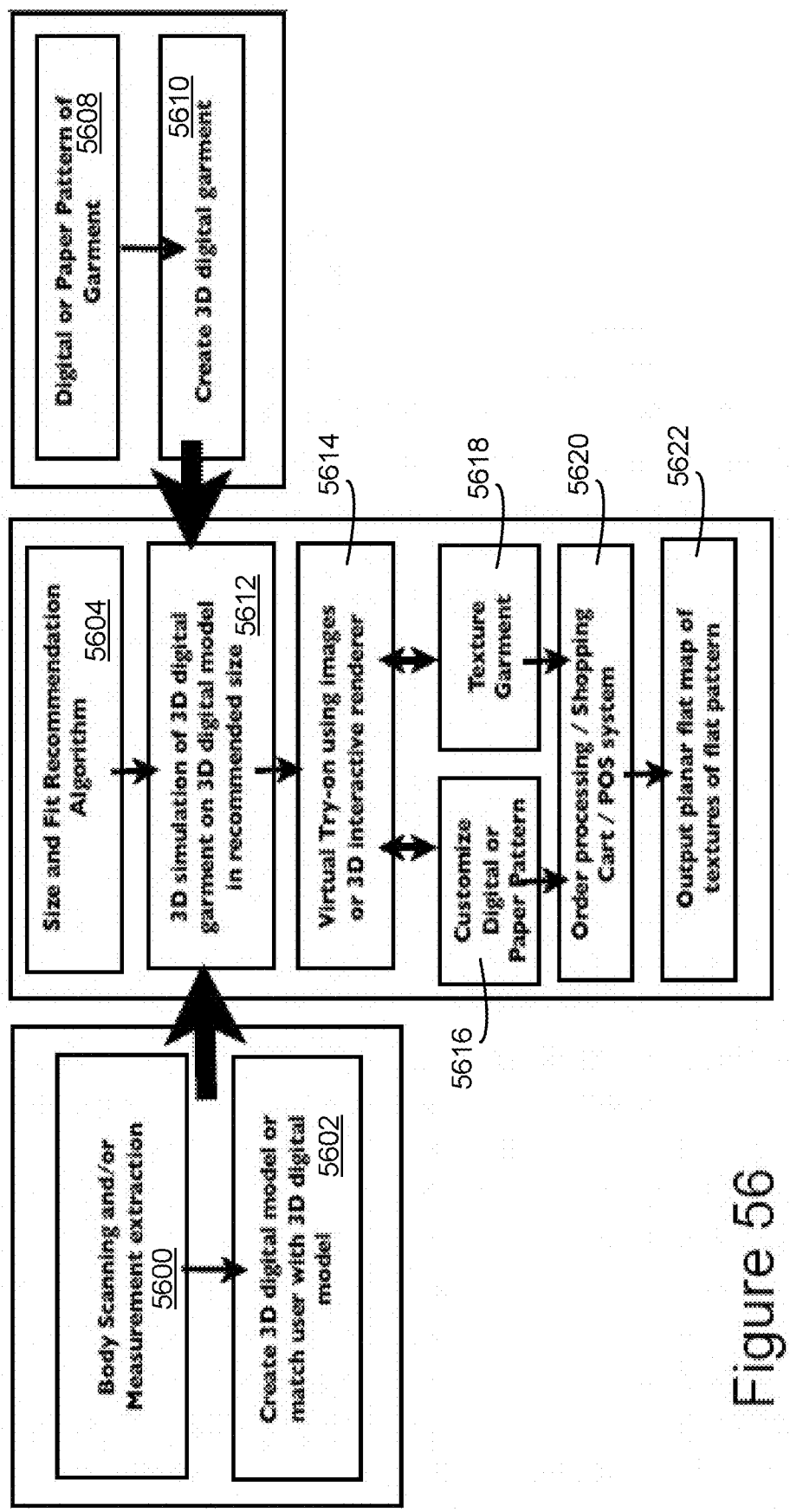
FIG. 56 is a flow diagram illustrating the steps of a method for designing and fitting of a custom garment according to one embodiment.

With reference to FIG. 56, a flow diagram illustrates the steps of a method for designing and fitting of a custom garment according to one embodiment. In step 5600, either the person's body is scanned, or measurements are extracted. In step 5602, a 3D representation of the person is created or matched. In step 5604, the system may determine a size and fit recommendation for the person. A digital or paper pattern 5608 of the garment is converted to a 3D digital garment in step 5610. In step 5612, the system may simulate the recommended size of the digital garment on the 3D representation of the person. In step 5614, the system may display the recommended size of the garment on the 3D representation of the person. In step 5616, the system may create a digital paper pattern for the garment, and in step 5618, the system may texture the garment. In step 5620, the person's order for the garment may be processed, and in step 5622, the system may output a planar flat map the textures of the flat pattern.

Figure 57:
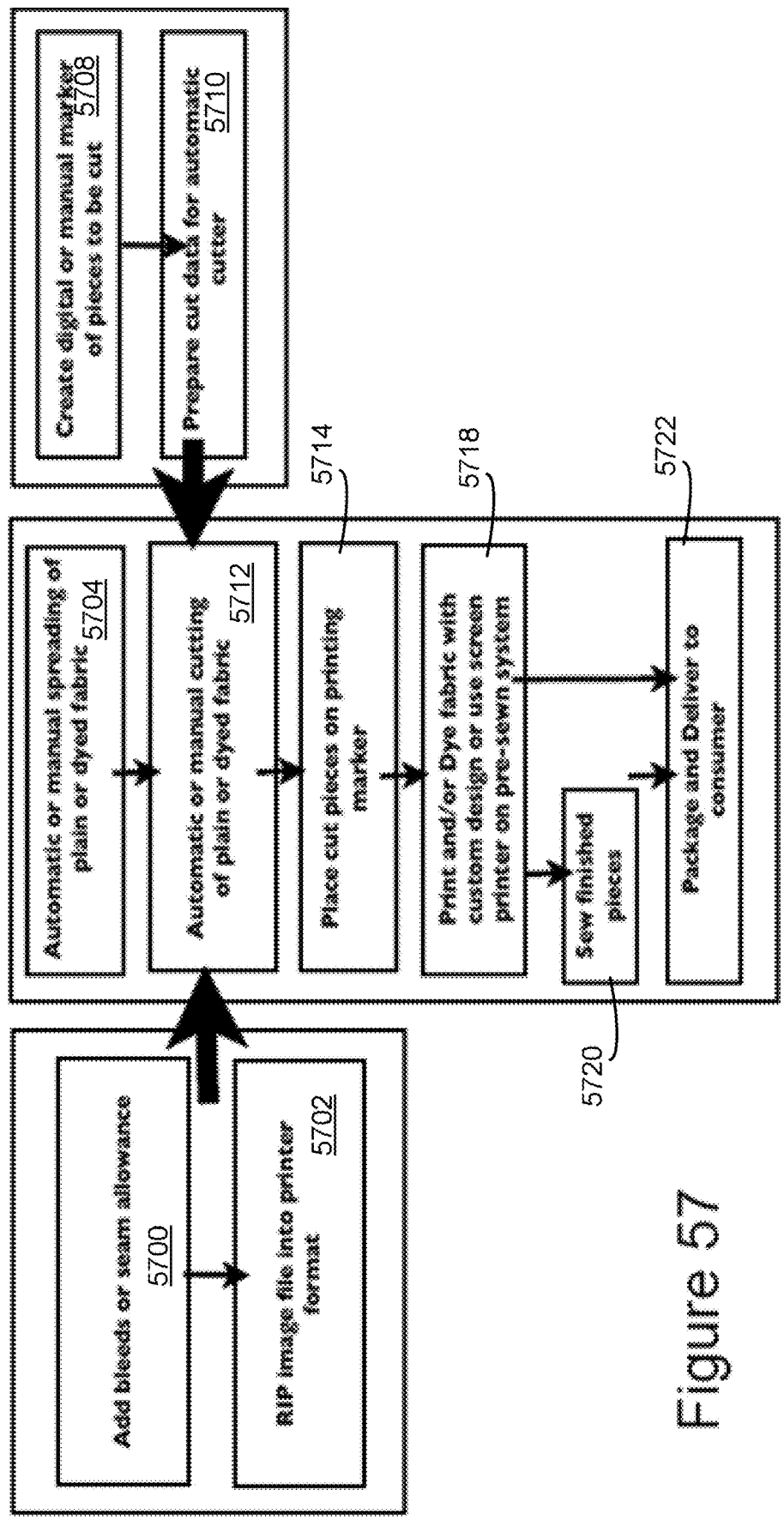
FIG. 57 is a flow diagram illustrating the steps of a method for manufacturing a customer garment according to one embodiment.

With reference to FIG. 57, a flow diagram illustrates the steps of a method for manufacturing a custom garment according to one embodiment. In step 5700, bleeds and seem allowances are added. In step 5702, the RIP image is converted in to printer format. In step 5702, the fabric is spread. In step 5708, marks of pieces to be cut are created. In step 5712, the fabric is cut. In step 5714, the cut pieces are placed on the printer marker. In step 5718, the custom design for the garment is printed on the garment. In step 5720, the finished pieces are sewn. In step S722, the garment is packaged and shipped to the customer.

Cloud Storage

Figure 58:
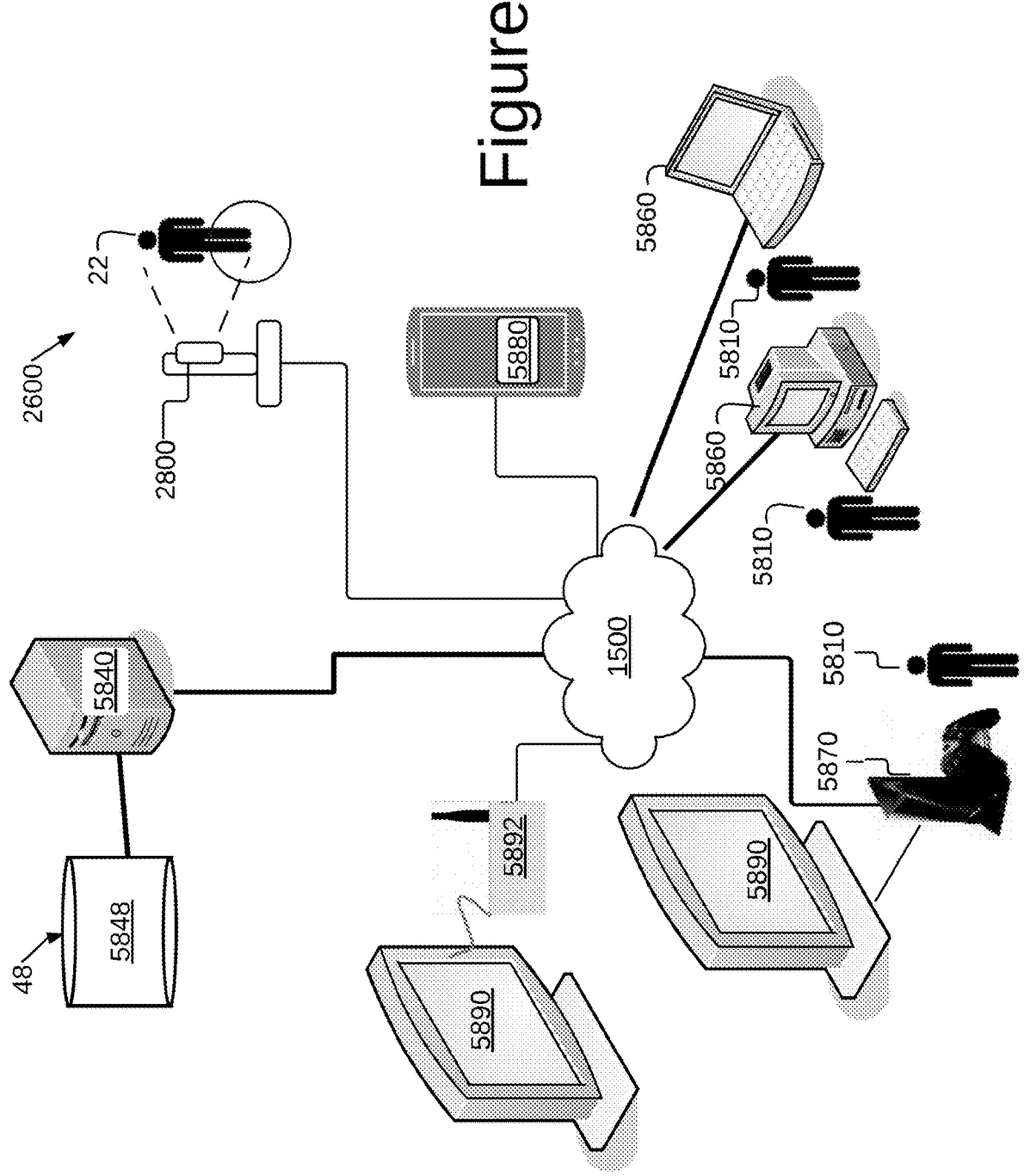
FIG. 58 is a diagrammatic representation of an exemplary internet-based system in which the system and method may operate according to one embodiment.

With reference to FIG. 58, a diagrammatic representation of an exemplary internet-based system is shown in which the system and method may operate according to one embodiment. As is typical on today's internet 5100, users 5810 may connect to and use the internet 1500 over several platforms. In some embodiments, users 5810 may fitness experts, doctors, or the consumers 22 themselves who get scanned. Those platforms may include personal computers 5860, mobile phones or tablets 5880, or the like. One of the latest ways to connect to the internet includes using internet protocol television, or IPTV, boxes 5892. These IPTV boxes 5892 include a wireless or wired device that has a memory and storage for applications or apps that connects to the internet 1500. Through an IPTV box 5892, users may use the apps contained therein to display videos, pictures, and internet sites on a television (TV) 5890. The television is typically connected to the IPTV box 5892 via an HDMI cord, component cable, or audio/video (A/V) input lines.

Over and above the mobile phones and tablets 5880, computers 5860, and the like, discussed above, other popular devices, such as modern game consoles 5870, are now capable of video play. Game consoles 5870 such as the XBOX®, Playstation®, Nintendo®, Wii®, and others, provide for internet video presentation. Just as with the IPTV box 5892, game consoles 5870 typically connect to a TV 90 on which videos may be viewed and games played.

One or more servers 5840 may include one or more storage devices 5848 containing one or more databases. One or more scanning systems 2600 with having a range camera 2800 is further connected to the internet as described above in more detail.

Figure 59:
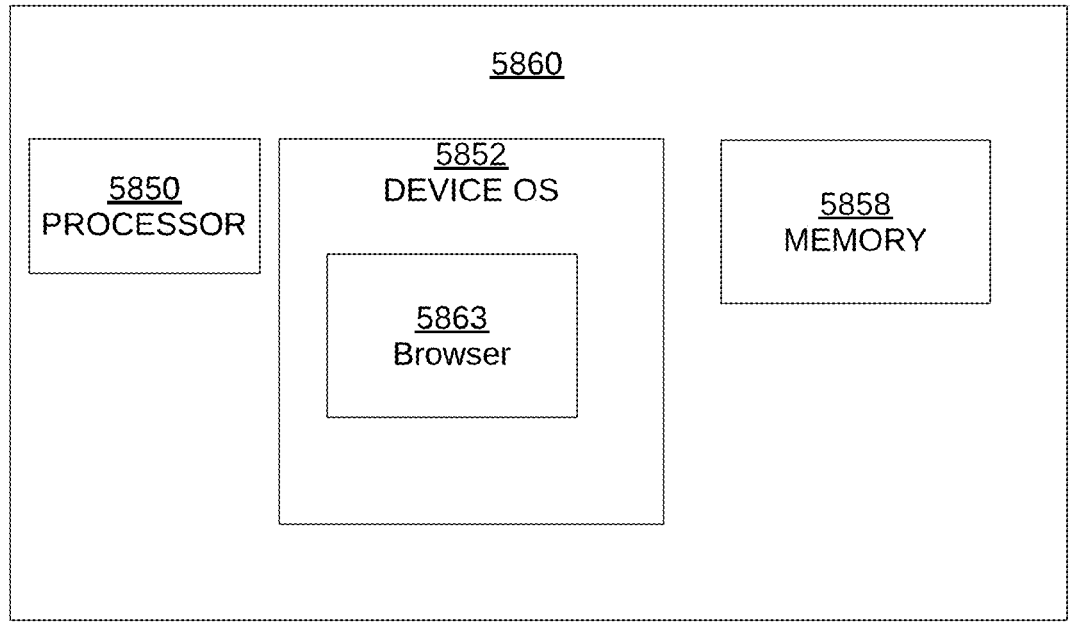
FIG. 59 is a diagrammatic representation of the internal components of one or more of the user devices of FIG. 58.

With reference to FIG. 59, a diagrammatic representation of the internal components of one or more of the user devices 5860 (5892, 5870, 5880 in FIG. 58) is shown. As those skilled in the art would recognize, each user device 5860, 5892, 5870, 5880 may include a processor 5850 and operating system 5852, on which executable instructions of a browser app 5863 may execute. As those skilled in the art would recognize, the browser app 63. Further, the user devices 5860, 5892, 5870, 5880 may each have a random access memory (RAM) 5858 that may be used for running browser app 5863, loading programs, and storing program variable data.

Figure 60:
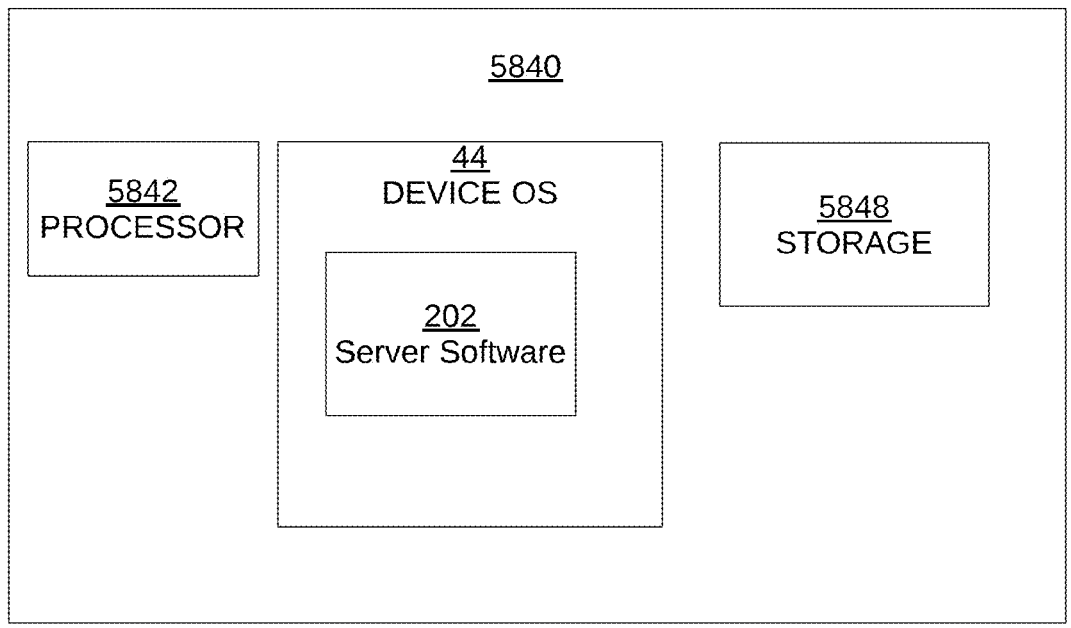
FIG. 60 is a diagrammatic representation of the internal components of the server device of FIG. 58.

With reference to FIG. 60, a diagrammatic representation of the internal components of the server device 5840 of FIG. 58 is shown. As those skilled in the art would recognize, the server device 5840 may include a processor 5842 and server operating system 4844, on which executable instructions of server software 202 may execute. As those skilled in the art would recognize, the computer program, which may embody server software 202, may be loaded by an operating system 5844 for running on the server 5840.

Figure 61:
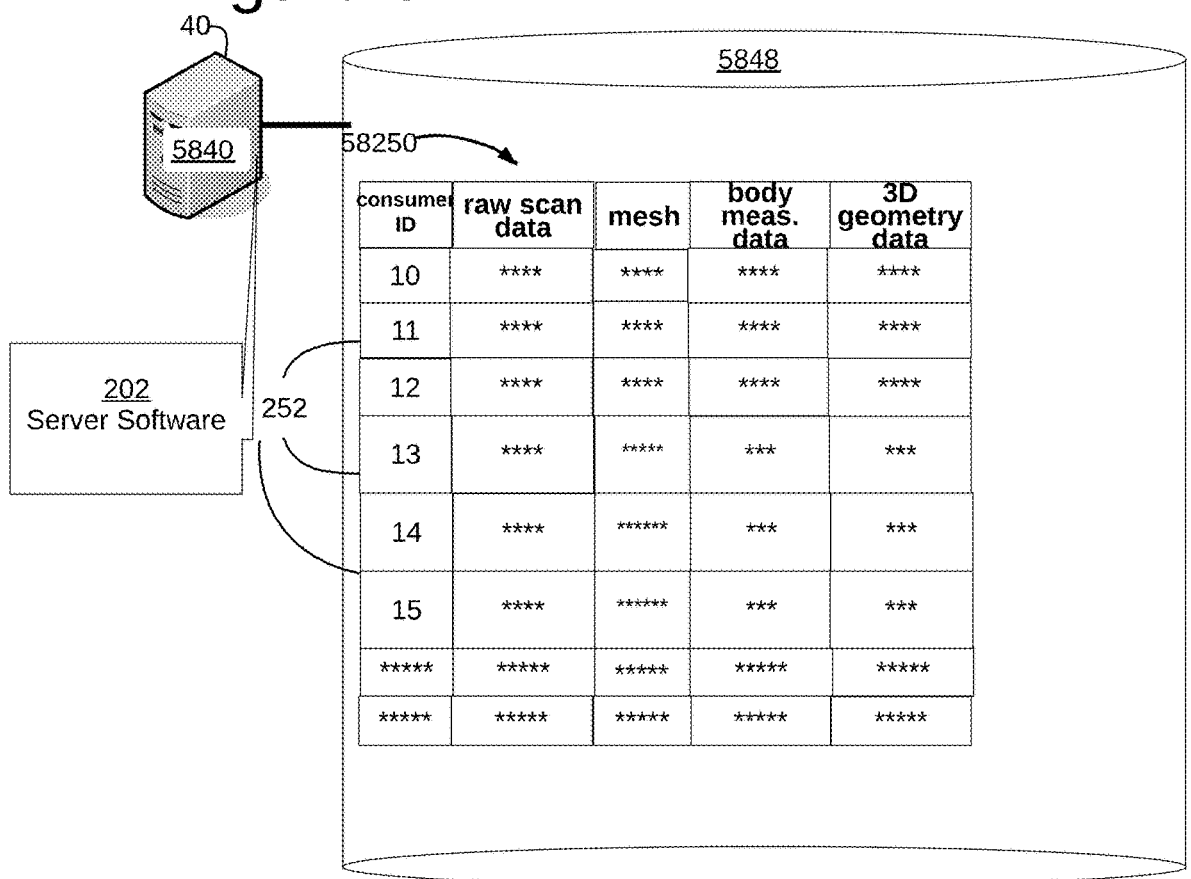
FIG. 61 is a diagrammatic representation of the one or more servers, and a storage device.

With reference to FIG. 61, a diagrammatic representation of the one or more servers 5840, and a storage device 5848, is shown. As indicated above, the server 5840 may have executing within server software 202. The server software 202 may comprise instructions to store and process user scanning data for users 5810 as described above. The storage device 5848 may store one or more databases to store user scanning data. An exemplary database table 58250 is shown in FIG. 61 illustrating some of the electronic data that may be stored and transformed to manage user scan data for consumers 20. For example, scan data stored in the database 58250 may be data collected as a result of capturing and analyzing 3D body scans as described above. This data may include, by way of example and not by way of limitation, raw scan data collected by a depth sensor 2600, 3D geometry (mesh) data created from raw scan data body measurement data determined by analyzing raw scan data and/or 3D mesh data, 3D geometry data created to display measurements in 3D, and scan subject information including name, email address and demographic data including height, weight, age and gender.

Figure 62:
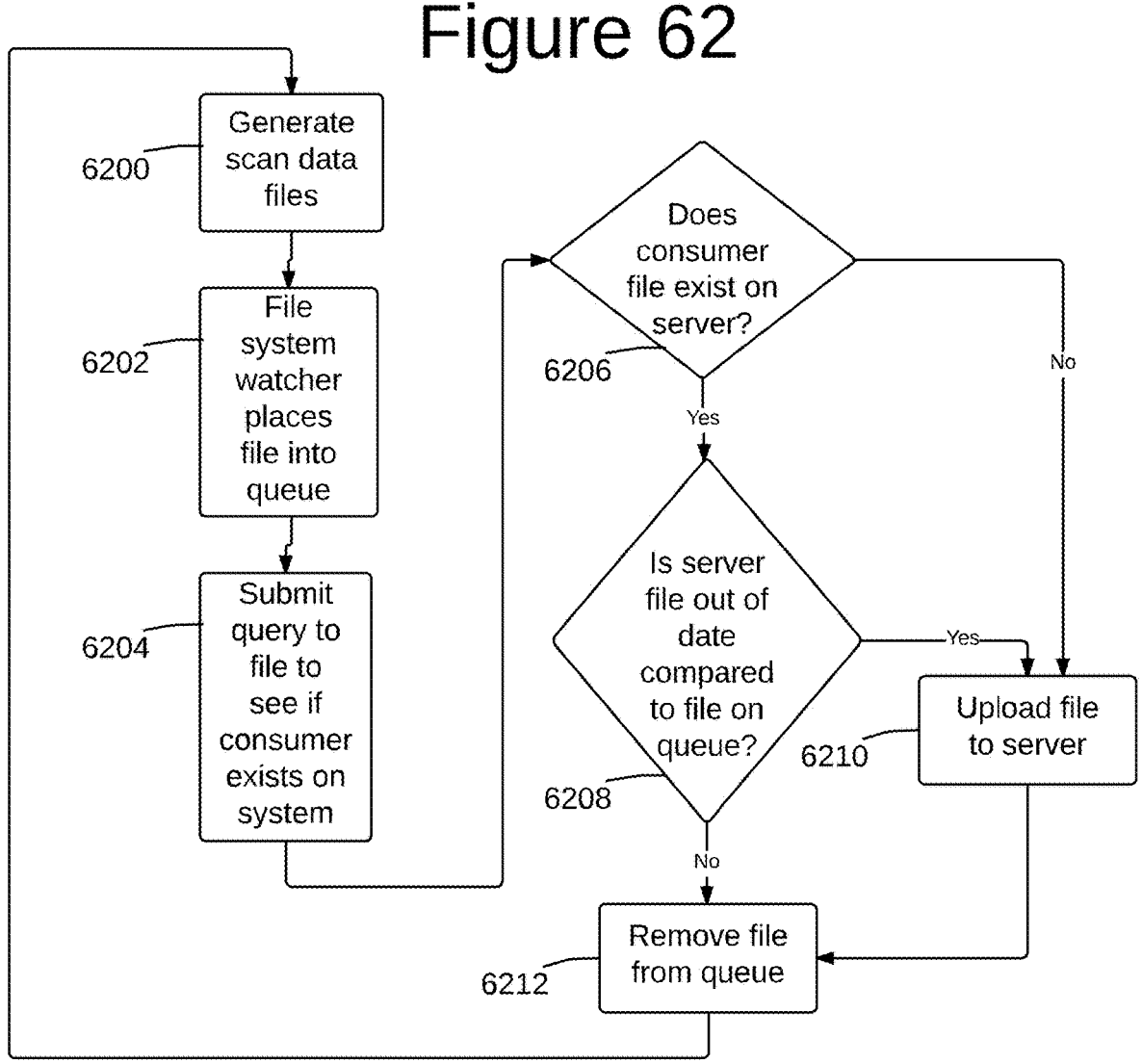
FIG. 62 is a flow diagram that illustrates steps performed by one embodiment for saving and uploading file records to the server of FIG. 58.

With reference to FIG. 62, a flow diagram illustrates steps performed by one embodiment for saving and uploading file records. In step 6200, files generating by the scanning system 2600 are created and saved on the local storage device. In step 6202, the generated files may be placed on a queue for uploading, which may be done by a system watcher module. In step 6204, a query is submitted to the server 5840 to determine if the consumer 20 for the scan data exists in database 58250 on server 5840. In step 6206, the server software 202 determines whether the consumer 20 already has data in the database 58250. If so, in step 6208, the server software 202 determines whether the data stored in database 58250 is out of date. If so, then the files are uploaded form the queue to the server 5840 in step 6210. If not, in step 6212, the files are removed from the queue.

Figure 63:
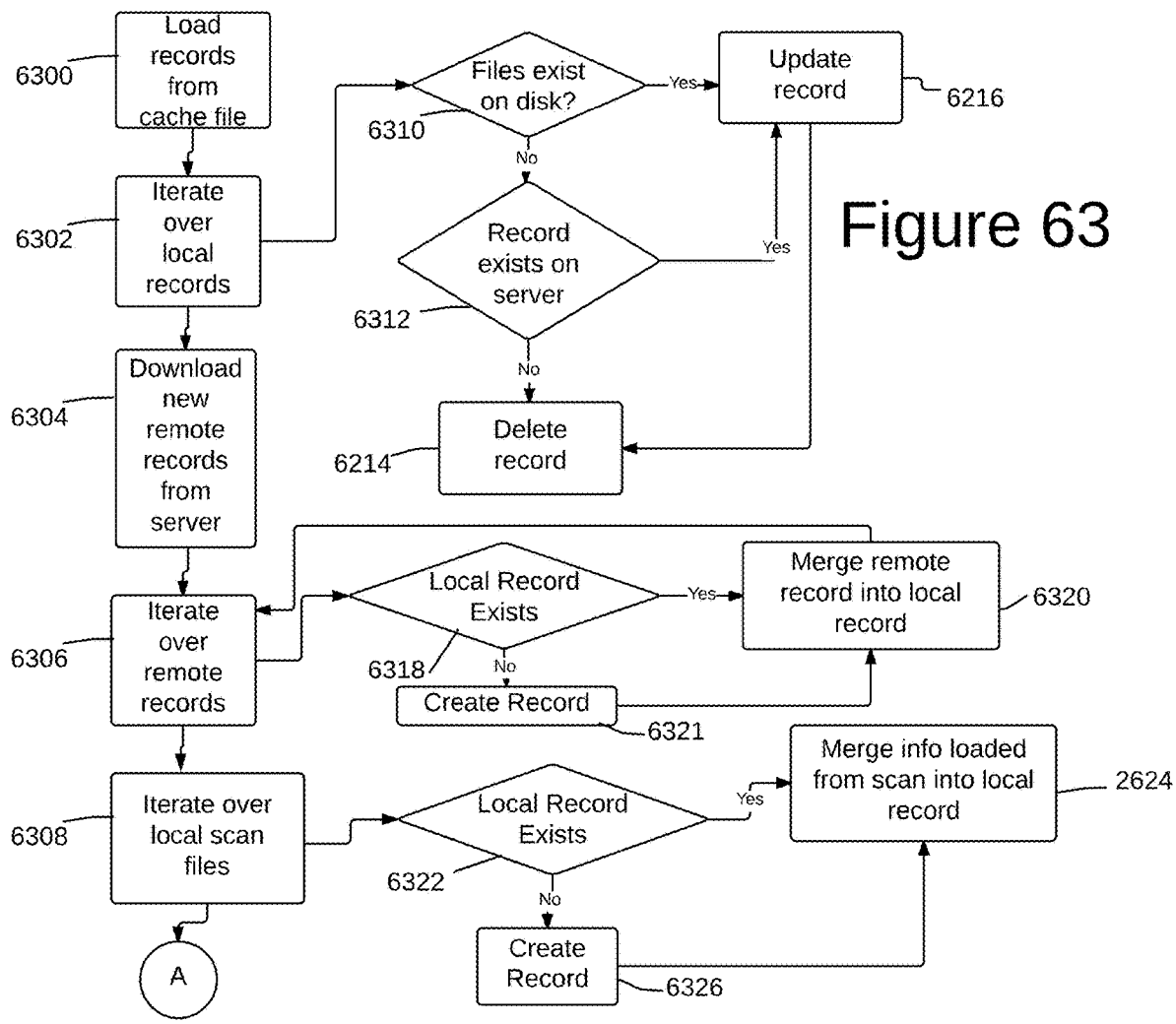
FIG. 63 is a flow diagram that illustrates steps performed by one embodiment for locally synchronizing scan data with cloud or server data, and merging all data in the system.

With reference to FIG. 63, a flow diagram illustrates steps performed by one embodiment for locally synchronizing scan data with cloud or server data, and merging all data in the system. In step 6300, scan records maybe loaded from a cache file. In step 6302, the local records are iterated. For each record, in step 6310, it is determined whether scan files exist on the local storage. If so, then in step 6316, the record is updated. Otherwise, in step 6312, it is determined whether the record already exists in database 58250. If not, then the record is deleted in step 6314. Otherwise, the record is updated in step 6216.

In step 6304, all new remote records are downloaded from the server 5840 from database 58250. In step 6306, the system iterates through the downloaded records. In step 6318, the system checks for whether each record exists locally. If so, then the remote record is merged into the local record in step 6320. If not, then in step 6321, the local record is created.

In step 6308, the system iterates over the local scan files. For each file, the system checks for whether a local record exist in step 6322. If so, then, in step 6324, the information from each scan file is loaded into a local record, which is created in step 6326.

Figure 64:
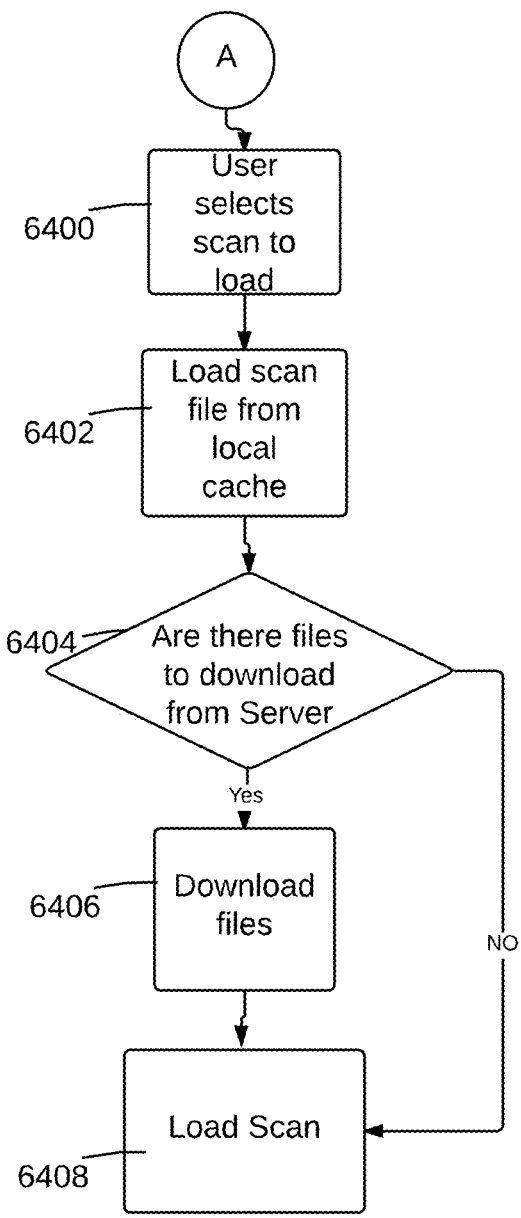
FIG. 64 is a continuation of the flow diagram if FIG. 63.

With reference to FIG. 64, continued steps from the flow chart of FIG. 63 are shown. In step 6400, a user may select scan data to view or process. The selected scan data is loaded from the cache in step 6402. In step 6404, it is determined whether there are files to be downloaded from the server 5840. If so, then in step 6406 the files are downloaded, and then loaded in step 6408.

Explicit Determination of Biometrics from Body Surface Imaging Technology

A biometric is a measurement of the body. Anthropometric measurements can be considered a type of biometric. These topological or anthropometric biometrics have a long history of value in a wide range of industries. However, deriving these biometrics, in practice is challenging due to the inaccuracy and imprecision of the traditional manual methods used. Common methods include measuring tapes, photographs, calipers, and other anthropometric tools. Since these methods depend on human operation, they are fraught with human error. In contrast, body surface imaging technology, sometimes referred to as 3D body scanning, have been shown to be quite effective, in the prior art, at overcoming human error considerably. These scanners typically can automate the process of capturing and measuring the surface of the body. We refer to this kind of body scanner as a Body-Surface Imaging Device or BSI device to distinguish it from other body scanners that don't measure the surface of the body. More generally, BSI devices can be defined as a subset of a larger set of devices called Body Measurement Devices or BMDs. BMD's could include everything from a CAT Scanner or a body weight scale, to a blood pressure measuring device or set of calipers. The data that a BMD produces is called a biometric. For example, a CAT or MRI scanner BMD might measure a biometric associated with the presence of disease or injury.

BSI devices have been used for more than a decade. Vendors for BSI devices in the prior art include [TC]$^2$ Labs, located at 2500 Reliance Ave., Apex N.C. 27539, USA and Human Solutions GmbH, located at Europaallee 10, 67657 Kaiserslautern, Germany.

In the prior art, BSI devices from vendors would often produce biometrics that were difficult or in some cases impossible to duplicate without that particular vendor's own BSI device. In other cases, the methods that the vendors in the prior art would use would be restrictive or limiting in practice. For example, the TC^2 method of deriving biometrics, like a waist circumference, would be performed on the point cloud. This is limiting in practice, however, since there isn't much you can do with a point cloud in industry. It one preferred embodiment it may be more beneficial to first create a mesh from the point cloud, and then proceed to extract further biometrics (e.g a waist circumference) directly from the mesh.

The precision of these biometrics is often dependent on the reliability of finding distinct features of a human body (landmarks), for example the tip of a shoulder, the small of the back, the fullest point of a breast, etc.). Also important to precision is the consistency of finding that feature across demographics and the wide variety of human body shapes and sizes. Additionally, landmark detection must be consistent across the changing body of a single subject, as their body shape and metrics change over the course of their lifetime.

There are many ways to derive landmarks. One example can be made by looking at motion capture systems, such as the XBOX Kinect, by Microsoft. Motion capture systems can be considered a BMD. Microsoft uses training data reflective of a sample population to determine landmarks. For example, Microsoft derived its own method of landmark detection for use in gaming with the Microsoft Kinect®. Their method is to look for patterns in the distribution of pixels at various depths, frame by frame, to determine the pose or shape of person in a given period of time and uses training data to help determine the pose or intended movement of the subject.

In the embodiments described herein, the first step may be to assume the body is static, and then use several images to develop a 3D model, and then to derive landmarks on or within or in the space around the 3D model. These landmarks then assist in the creation of rules to extract precise anthropometric measurements, not associated with movement (like the Microsoft system), but rather with shape. (see above description regarding scanning and avatar creation).

Landmark positions can also be adjusted or altered for improved precision when attempting to match a landmark to a distinct feature of the human body. Users of a system that derives landmarks and measurements from a 3D body scan can provide additional feedback about where a key body landmark should be found on a 3D body scan, improving the landmark detection system by providing training data. Users can also provide additional feedback about where a measurement should be taken that can be used to improve the quality of the measurements taken by the system.

In one embodiment, methods are used by the system for determining landmark positions and extracting body measurements and other biometrics from a 3D body scan. The following describes one embodiment about how to determine landmarks and extract precise measurements, as mentioned in paragraph 00278. This method is distinct from Microsoft's method as well as methods from other body scanning vendors. The process of determining landmarks and extracting measurements is not limited to this method.

Additionally, in some embodiments, the system may perform the step of interactively creating and altering landmark positions and measurements. These alterations can be tracked and used as training data to improve the precision of landmark positions and body measurements and other biometrics that are automatically calculated by a system.

In one embodiment, by way of example and not by way of limitation, below is a description of one method of calculating anthropometric measurements from 3D body scan data. In this example, the system may analyze the 3D body scan and calculate data that is then used to extract a measurement over the fullest part of the chest or bust. This example embodies only a single measurement, but the method can be used for any number of measurements, of any type, both on or inside of or in the space around a 3D body scan. This example should not be construed as limiting the method to this measurement.

Figure 76:
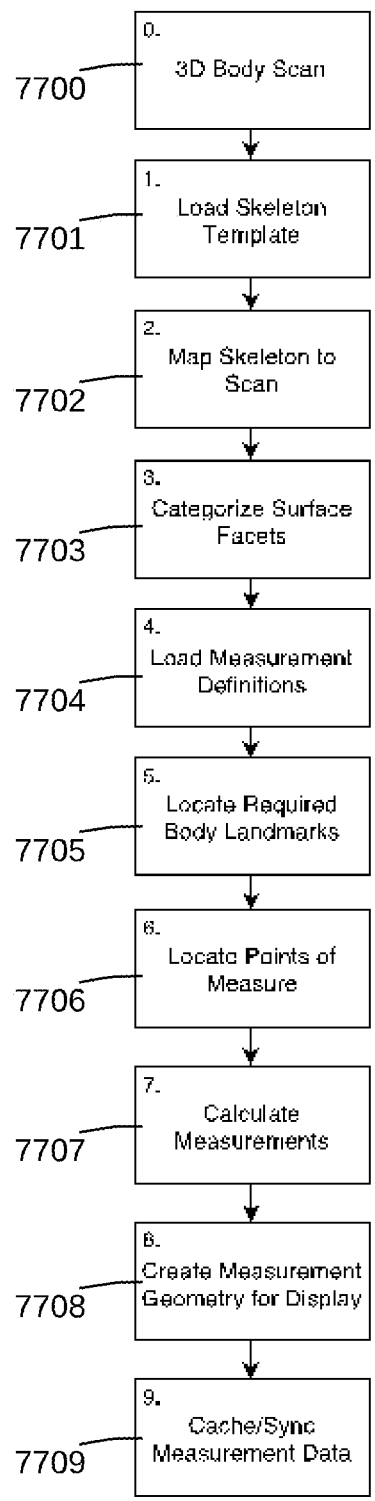
FIG. 76 is a flowchart illustrating measurement extraction steps performed by the system according to one embodiment.

With reference to FIG. 76, a flowchart is shown illustrating measurement extraction steps performed by the system. To summarize, the steps are as follows: apply a skeleton to 3D body scan data (steps 7701-7702) (see FIG. 78 for an image illustrating a skeleton fitted to the 3D body scan); categorize surface facets of the 3D body scan into regions (step 7703) (see FIG. 79 for an image illustrating a body scan with facets categorized); load landmark and measurement definitions and derive landmarks (steps 7704-7705); calculate points of measure and extract measurements (step 7706) (see FIG. 77 for a flowchart describing a measurement extraction example); generate geometry and display measurements to user (step 7707); sync derived information about landmarks and measurements with cloud servers (step 7708).

In more detail, in step 7701 the system may load a skeleton template. A skeleton template is a hierarchical list of joints, where each joint has a location in 3D space and an optional parent joint. The joints serve as a starting point when determining where skeleton joints would be in a 3D body scan. In this embodiment, the skeleton template is created following common proportions of the human body.

Figure 78:
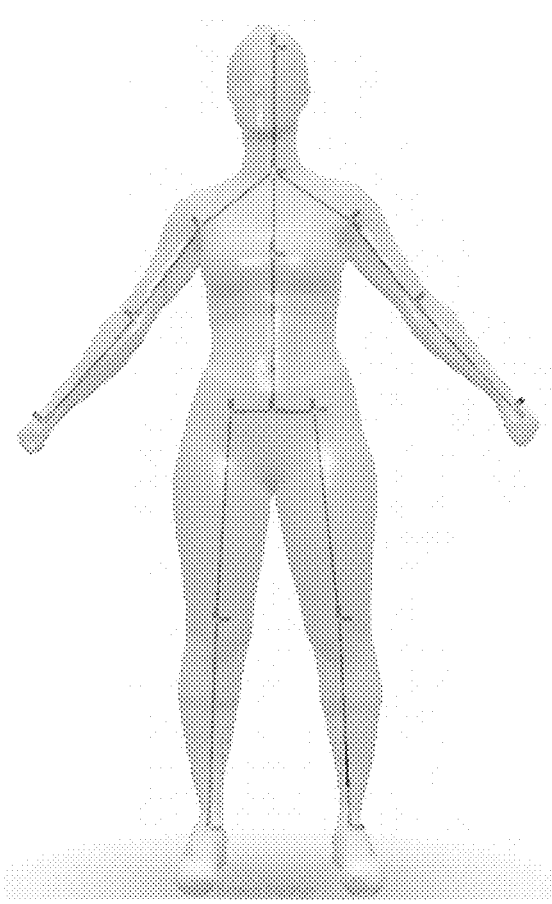
FIG. 78 is an image illustrating a skeleton fitted to the 3D body scan according to one embodiment.

In step 7702, the system may map the skeleton to the scan (see FIG. 78 for an image illustrating a skeleton mapped to a 3D body scan). The skeleton template is first scaled to an appropriate size given the height of the 3D body scan. The joints of the template are then fitted to the 3D body scan, constrained by assumptions about how the joint in a real human body is able to move, and the positions of other joints in the template that are lower in the skeleton hierarchy (parent-child relationship) (see FIG. 78 for an image illustrating a skeleton mapped to a 3D body scan). One skilled in the art would recognize the fitting of the skeleton to the 3D body scan as part of a process known as rigging, when an object is used as a bone structure to aid in animating another object.

Figure 79:
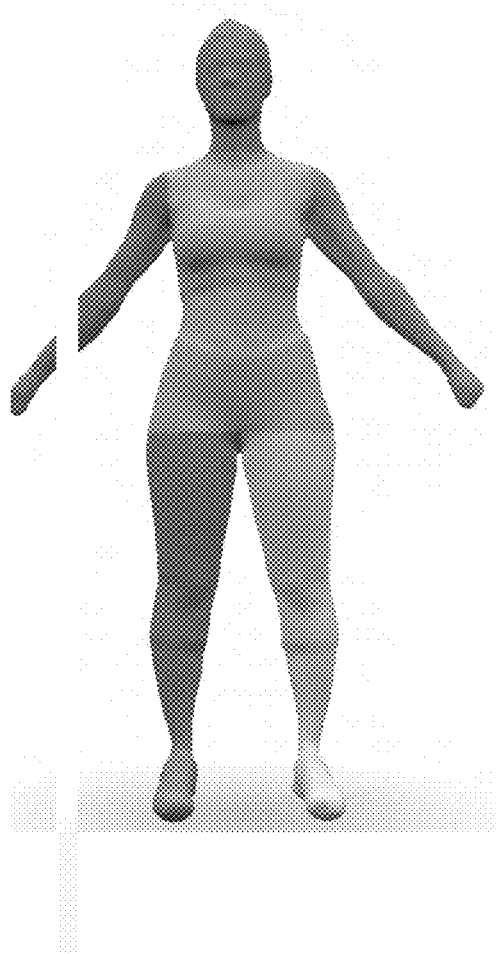
FIG. 79 is an image illustrating 3D body scan surface facet categorization according to one embodiment.

In step 7703, the system may categorize surface facets (see FIG. 79 for an image illustrating surface facet categorizations for a 3D body scan). The fitted skeleton template and other heuristics are used to categorize areas of the surface of the 3D body scan into regions that correspond to limbs and other regions of the human body. For example, the 3D body scan surface in this embodiment is categorized into the following categories: head, left arm, right arm, torso, left leg, right leg (see FIG. 79 for an image illustrating surface facet categorizations for a 3D body scan).

In step 7704, the system may load measurement and landmark definitions. Each measurement to be generated of the 3D body scan may follow a set of rules and constraints that make up the definition of the measurement. These rules determine the type of measurement (point-to-point or circumference, for example), and constraints that affect the creation of the measurement. For example, a rule or constraint could determine that a measurement be planar along a plane defined by 3 points. In another example, a rule or constraint could determine that a measurement must pass through a set of given points in 3D space while otherwise remaining coincident with the surface of the 3D body scan.

Figure 80:
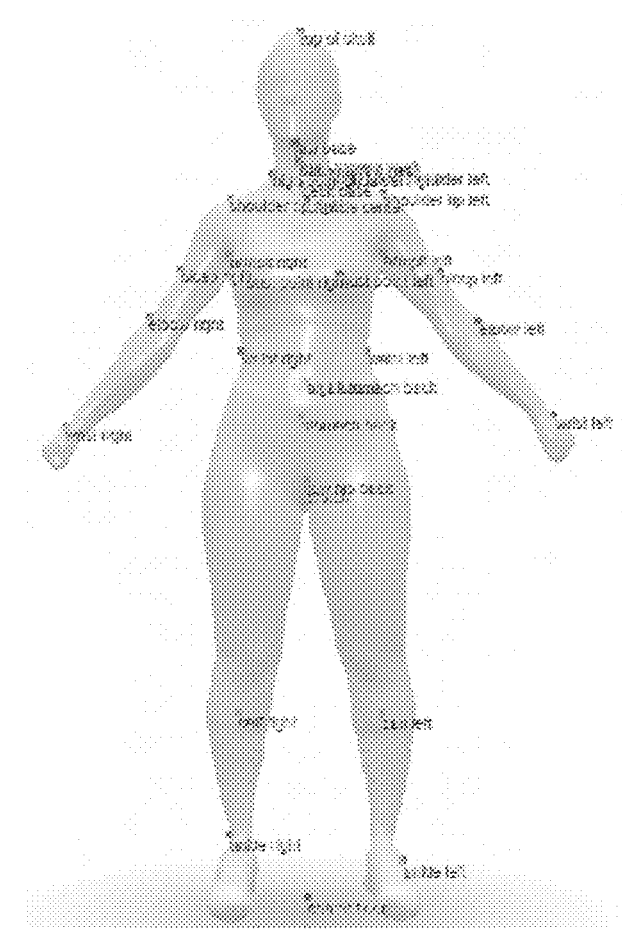
FIG. 80 is an image illustrating derived landmark positions on a 3D body scan according to one embodiment.

In step 7705, the system may locate required body landmarks, (see FIG. 80 for an image illustrating some landmarks and their derived positions on a 3D body scan). Often, though not always, the definition of a measurement requires first the locations on the 3D body scan (landmarks) that represent key feature points of a human body's shape, size, internal or external characteristics. These landmarks can be on the surface of, within the volume of, or in the space around a 3D body scan. An example of a landmark on the surface of a 3D body scan is a landmark corresponding to the top of the skull. An example of a landmark within the volume of a 3D body scan is a landmark corresponding to the center of the mesh at the position of the left ankle bone. An example of a landmark in the space around the 3D body scan is a landmark corresponding to the center of the mesh at the height of the lowest part of the mesh, the center of the floor plane.

Figure 77:
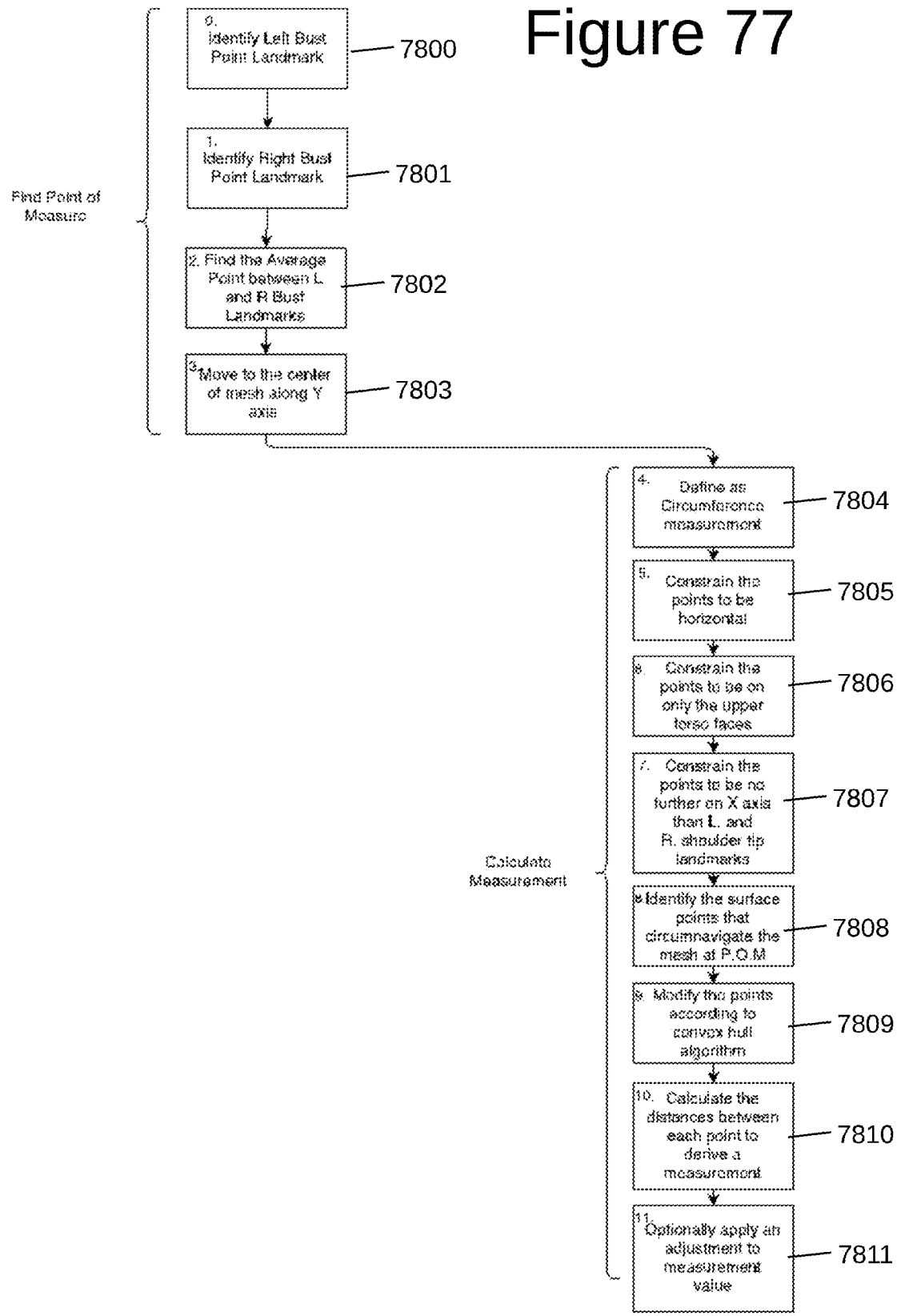
FIG. 77 is a flow diagram illustrating a process for a circumferential or girth measurement according to one embodiment.

In step 7706, the system may locate points of measure and calculate measurements (see FIG. 77 for a flowchart illustrating steps taken to calculate a measurement). The system may determine where a measurement should be taken (the point of measure) according to the definition of a measurement, and derive the path the measurement will follow and then calculate the distance of the path to arrive at the measurement value.

For example, with reference to FIG. 77, this process can be done for a circumferential or girth measurement by following these steps. I in steps 7800-7803, the system may find the point of measure. The system may begin by defining the location where a measurement is to be taken on a 3D body scan. In this example, the system may start with first finding landmarks that represent the Left and Right Bust points on the body. The system may then find the average location between the two, and finally find a point at the center of the 3D body scan in the Y axis, using the X and Z coordinates we found previously by taking the average of the bust point locations.

Next, in steps 7804-7811, the system may calculate the measurement. The system may plot the path of the measurement according to rules defined by the measurement definition. In this example, the system may first determine that this will be a circumferential measurement that is horizontal (parallel to the ground) steps 7804-7805). Further constraints are applied that ensure that this measurement is plotted only along the surface facets that are within the surface category for the upper torso, step 7806, and that it should not be plotted any further along the X axis than the left and right shoulder tip landmarks on the 3D body scan, step 7807).

The measurement path is then plotted following these rules and constraints, along the surface of the 3D body scan, at the location of the point of measure determined earlier step 7808). Next, the measurement points are modified according to a convex hull algorithm, for example, using the algorithm known as Graham Scan, (Graham, 1972), step 7809). One skilled in the art would know about the various convex hull algorithms. The application of the Graham Scan algorithm by no means limits the invention to using only that convex hull algorithm, or any algorithm designed to modify a path. (see above description regard to body scanning using multiple range cameras).

Finally, the length of the measurement is calculated by determining the lengths between each point in the plotted path. Optionally, an adjustment value or percentage can be applied to a final length to modify the value steps 7810-7811).

Figure 81:
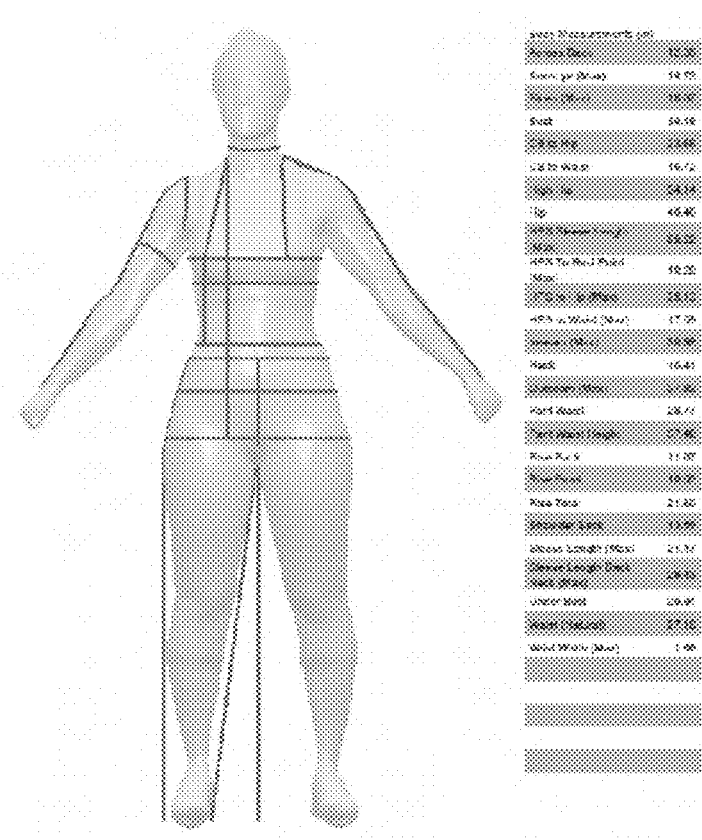
FIG. 81 is an image illustrating examples of measurements displayed in 3D, their locations on a 3D body scan, and their calculated values according to one embodiment.

With reference back to FIG. 76, in step 7707, the system may Create Measurement Geometry for Display (see FIG. 81 for an image is shown illustrating examples of measurements displayed in 3D, their locations on a 3D body scan, and their calculated values). The system may generate 3D geometry (a polytube) representing the measurement path in 3D space for display and user interaction in a software application.

In step 7708, the system may cache/sync measurement data. Measurement data, including dependent landmark positions, points of measure, measurement paths, measurement values and 3D geometry are collected as part of body scan data by the measurement system and synced with cloud storage as per the process outlined in the section entitled Cloud Server Body Scan Data System herein.

In another example, according to one embodiment, a measurement or landmark that was calculated by the system can be interactively edited to adjust the point of measure. For example, a user may select an edit tool and then choose the abdominal waist measurement. By dragging with a mouse or finger or other interaction method, the user can interact with the measurement, changing its position along the surface of the 3D body scan or in space around the 3D body scan. In another example, the user may select an edit tool and then choose the left bust landmark. By dragging with a mouse or finger or other interaction method, the user can change the position of the landmark along the surface of the 3D body scan.

In this example, a previously determined measurement will be recalculated dynamically by applying the new point of measure given by the user's interaction and regenerating the measurement. Measurements and other biometrics that are dependent on the measurement will also be altered. For example, if a Thigh measurement is interacted with, a mid-thigh measurement will also change position because the mid-thigh measurement depends on the position of the thigh measurement. In another example, a body composition value that is derived using anthropometric measurements can be altered by changing or altering the measurements that it depends on. In yet another example, a point-to-point measurement whose path starts at the Left Shoulder Tip landmark will be regenerated as the Left Shoulder tip landmark is altered by the user. Changes and edits to measurements are cached and synced with cloud storage as additional biometric scan data, and can be used to improve the accuracy of measurements and landmarks on 3D body scans.

Figure 82:
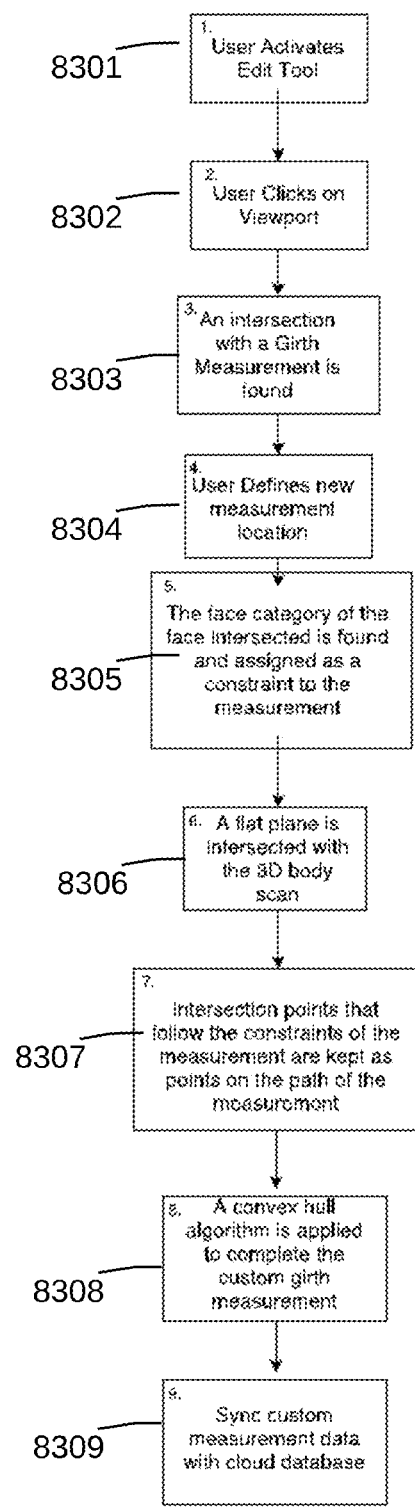
FIG. 82 is a flowchart that outlines the steps taken by the system when recalculating a measurement based on a user-driven interaction that changes the point of measure according to one embodiment.
Figure 83:
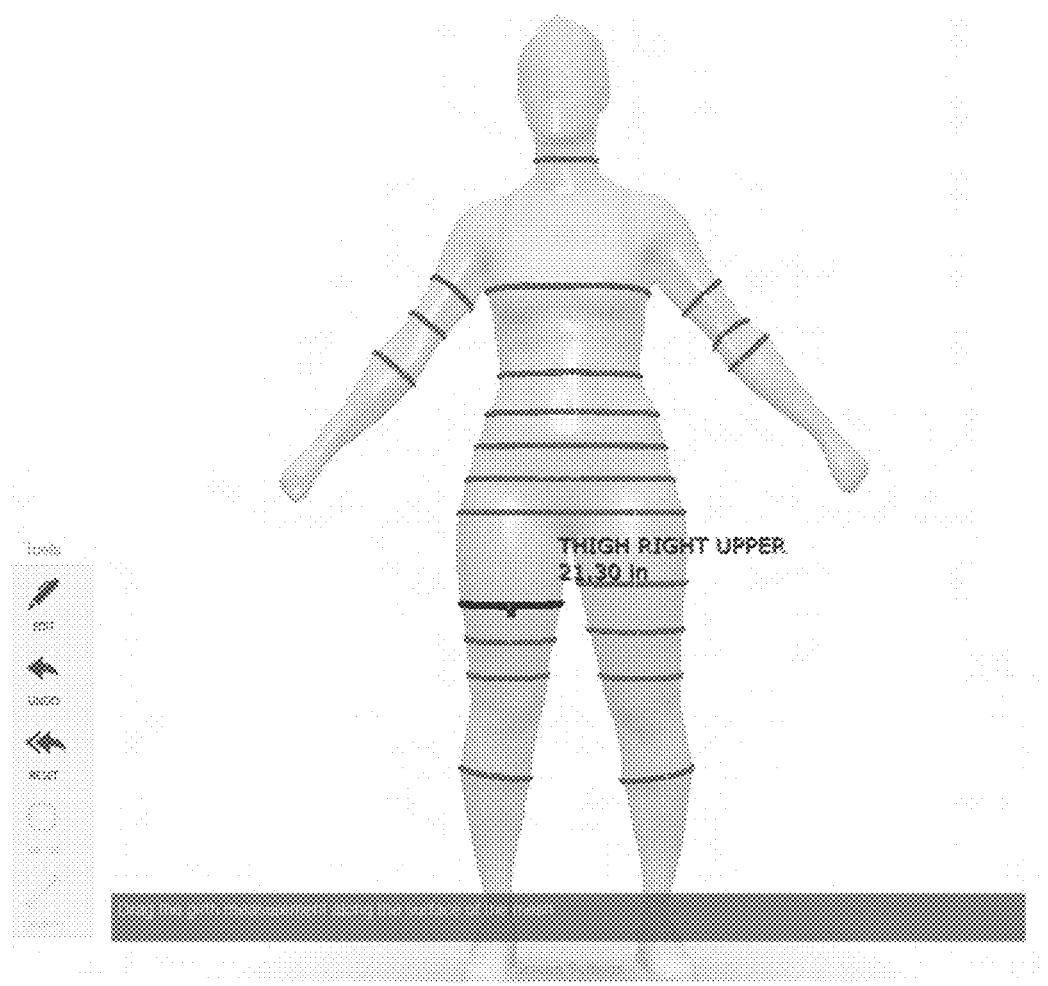
FIG. 83 is an image illustrating a measurement being interacted with on a 3D body scan according to one embodiment.

With reference to FIG. 82, a flowchart outlines the steps taken by the system when recalculating a measurement based on a user-driven interaction that changes the point of measure. Also with reference to FIG. 83, an image illustrating a measurement being interacted with on a 3D body scan. With reference back to FIG. 82, a summary of the steps are: (steps 8301-8304) there is user interaction to define a new location for the measurement; (steps 8305-8306) the system may apply rules and constraints to the measurement; (steps 8307-8308) the system may plot the measurement path at the new location, and apply convex hull and update length value; (step 8309) Cache and sync changes to measurements.

In more detail, In step 8301, the user may activate an edit tool. In this example, a graphical user interface (GUI) is presented to the user to allow them to interact with the 3D body scan. The user interacts with a tool in the GUI to enable an editing mode for the extracted measurements on the 3D body scan.

In step 8302, the user clicks on a viewport. The user uses the GUI to choose (by tapping or clicking) a point in space on or around the 3D body scan that indicates which measurement the user wants to alter.

In step 8303, an intersection with a girth measurement is found. A ray is cast from the coordinate in screen space the user indicated to find an intersection with the 3D body scan or 3D geometry representing an extracted body measurement in 3D space. The intersection point identifies which measurement is to be altered.

In step 8304, the user defines a new location for the measurement. The user drags the selected measurement to a new location on the body. In step 8305, the face category of the face intersected is found and assigned as a constraint to the new measurement. For example, if the user chose to create a measurement on the torso of the 3D body scan in step 8304, only facets that are categorized as torso will be considered in step 8306 when the path of the measurement is plotted.

In steps 8306-8307, a flat plane is intersected with the 3D body scan and the path is plotted. A plane is created at the location and the intersection points between the plane and the 3D body scan are used to create the initial path of the measurement at the new position.

In step 8308, a convex hull algorithm is applied and the measurement length recalculated. Next, the measurement points are modified according to a convex hull algorithm, for example the algorithm known as Graham Scan, (Graham, 1972), and the length of the measurement in the new position is calculated.

In step 8309, the changes are synced with a cloud database. Scan data related to the alteration the user has made to a measurement position, and the new measurement's scan data including its value, 3D geometry used to interact with it, and the like (see data in above example) is synced with a cloud database (58250 in FIG. 61), according to the method outlined in the prior art.

In yet another example, new measurements can be created interactively by a user of the one embodiment. Measurements can be circumferential, point-to-point, areas, volumes and other types. Measurements are created following rules and constraints similar to the method shown in the above examples that illustrates how this embodiment takes a circumferential measurement.

In this example, the user is providing additional information about the type and position of the measurement. For example, a user may click a tool to create a girth measurement, and then choose a position on the 3D body scan to place the measurement. The user may make further adjustments to the position of the measurement. The measurement will be calculated by the system following the set of rules and constraints determined for that type of measurement. It should be noted that this example illustrates the creation of a girth measurement on the surface of the 3D body scan, but the invention is by no means limited to girth measurements, or measurements only on the surface of the 3D body scan.

Figure 84:
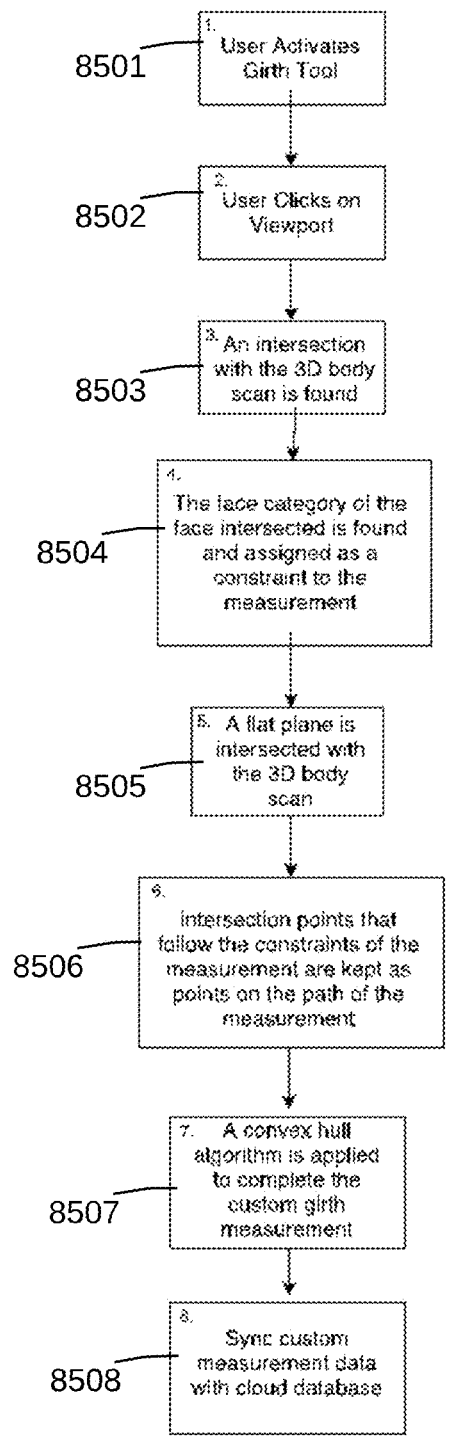
FIG. 84 is a flowchart that outlines the user-interactive measurement creation process for a girth measurement according to one embodiment.

With reference to FIG. 84, a flowchart outlines the user-interactive measurement creation process for a girth measurement. To summarize, in steps 8501-8502, a user interaction defines the location of a new measurement. In steps 8503-8504 the system may apply rules and constraints to the measurement. In steps 8505-8507, the system may plot the measurement path at the new location, apply convex hull and update length value. In step 8508, the system may cache and sync changes to measurements In more detail, in step 8501, the user activates a girth creation tool. In this example, a graphical user interface (GUI) is presented to the user to allow them to interact with the 3D body scan. The user interacts with a tool in the GUI that puts the system in a mode to create a new girth measurement. In step 8502, the user clicks on the viewport. The user uses the GUI to choose (by tapping or clicking) a point in space on or around the 3D body scan that indicates where the new measurement should be created.

In step 8503 an intersection with the 3D body scan is found. A ray is cast from the coordinate in screen space the user indicated to find an intersection with the 3D body scan or 3D geometry representing an extracted body measurement in 3D space. The intersection point identifies where the new measurement should be extracted on the 3D body scan.

In step 8504, the face category of the face intersected is found and assigned as a constraint to the new measurement. For example, if the user chose to create a measurement on the torso of the 3D body scan in step 3, only facets that are categorized as 'torso' will be considered in step 5 when the path of the measurement is plotted.

In step 8505, a flat plane is intersected with the 3D body scan and the path is plotted. A plane is created at the location and the intersection points between the plane and the 3D body scan are used to create the initial path of the new measurement.

In step 8506, a convex hull algorithm is applied and the measurement length recalculated. The measurement points are modified according to a convex hull algorithm, for example the algorithm known as Graham Scan, (Graham, 1972), and the length of the measurement in the new position is calculated. In step 8507)

In step 8507, the changes are synced with a cloud database. Scan data related to the creation of a new measurement by the user including the type of measurement, the measurement position, and the new measurement's scan data including its value, 3D geometry used to interact with it, and the like (see data in the above examples), is synced with a cloud database.

Implicit Determination of Biometrics from Body Surface Imaging Devices

The previous section described how one could derive explicitly biometrics from a body scan using a body surface-imaging device. Those biometrics are directly measured via the data created by the body surface-imaging device. However, biometrics not directly measured by the Body Surface Imaging Device could be predicted by it. For example, one could measure body fat % from a body surface-imaging device without explicitly measuring fat. Instead, one would correlate body fat percentage as measured by a well regarded body composition device, for a sample of a population, and then statistically correlate those readings with biometrics measured from a BSI device, like waist, hip, or other girth measurements from the same sample of subjects. In other words, implicit biometrics could be correlated with direct measurements and then be predicted via some statistical relationship. Recall from the earlier section that we define body measurement devices or instruments (BMD's) more generally to include any device or instrument that measures the human body in some way or can be used to extract biometrics of the body regardless of the instrument's purpose, including body surface imaging, CAT scans, MRI scans, body composition devices, blood pressure, thermometers, weight scales, fitness monitors, shoes, clothing, eyeglasses, accessories other wearables and more. Note, the definition of a device or instrument is used broadly herein to include even apparel, footwear and accessories. For example, clothing can be considered a measurement instrument, since clothing items have biometrics built in, such as size, which can be described as a measurement of the body and help describe a body both qualitatively, and quantitatively.

We can also define Non-BSI body scanning BMD's to include a further subset of body measurement BMD's. These BMD's relate to all non BSI BMD's, including, but not limited to CAT Scans, MRI Scans, Xray Scanners, RF Scanners, and more known to those skilled in the art. In other words, non-BSI BMD's are uniquely different than BSI BMD's as they capture biometrics directly, where BSI BMD's can't indirectly or explicitly measure.

Therefore, biometric data may include metrics derived explicitly from BMD's or implicitly through statistical means with other biometrics.

As a subset of biometric data, 3D body scan data refers to data either captured via the BSI BMD, or measured from the 3D body scan including, but not limited to, point clouds, 2D depth images, 3D surfaces, key body landmarks, pose/posture, and surface anthropometric data such as measurements (for example distances, girths, areas, volumes or FIG. 82 below for an example), and changes to all of the above over time.

In this respect, there are many ways to measure the human body. The most common methods are through visual imagery (photography, mirrors, etc), weight scales, and measuring tapes. The methods are common given widespread accessibility and acceptance. But much more sophisticated ways of capturing biometrics are available to people today. One common example is a class of body measurement BMD's called non-BSI BMD's, which include body scanners such as MRI, CAT scans, Xray scanners, etc. These body measurement BMD's are all uniquely able to measure with high precision biometrics that are otherwise difficult, impossible, or impractical to measure by other means. They are often able to measure internal biometrics (such as the presence of disease, injury, etc) that aren't otherwise visible on the surface of the body. They are highly complex machines in their construction and engineering and therefore are too expensive to use in more commercial environments, like our homes. As such, their use is often limited to airports/government buildings (high security), hospitals/clinics/labs (medical assessment and diagnosis), and academic research.

Another class of body measurement BMD's include BSI body scanners. Usually, they utilize either one or many photometric or IR cameras, lasers, structured light, time-of-flight sensors to measure the surface of the body. Unlike non-BSI body scanners BMD's, BSI body scanners provide external biometrics, like shape, pose, circumference, gait, and more. These are metrics that can be seen from the surface, but are difficult to measure precisely with anthropometric BMD's, which are prone to human error (measurement tapes, calipers, etc).

BSI body scanners were once also limited (due to cost) to academic or clinical environments for research purposes, or to niche groups for specific goals, for example motion capture for creation of 3D art assets (video games, movies). In the academic world, body scanning is performed with a single goal in mind, for example to create a 'size survey' of a population group, or to find relationships between a set of body measurements and demographic data.

However, BSI BMD's have recently become more mainstream, which is the result of the availability of low depth and photographic sensors (Primesense, Kinect, Mantis Vision (MV), Intel Real Sense, etc). As a result of their affordability and accessibility, BSI BMD's are now being used in a wide variety of commercial applications, including, but not limited to, fitness gyms and clubs, medical offices and retail stores.

Moreover, with the integration of such low-power affordable depth sensors into computer BMD's (the Kinect® bundled with the Xbox®, the Kinect for Windows®, the Real Sense® or MV® camera embedded in tablets phone, PC's, etc), BSI applications may become exponentially widespread.

If current adoption and distribution rates of BSI BMD's continues, the amount of resultant biometric data will quickly dwarf the amount of biometric data from more traditional non-BSI body scanners, presenting a completely new way to study the human body at scale and in large populations with high diversity.

In one embodiment, methods and systems for correlating biometrics derived from BSI BMD's with biometrics derived from other BMD's through regression analysis and/or other statistical techniques, resulting in the ability to predict biometrics not explicitly measured by a BSI body scanner are disclosed. As a consequence, users of BSI devices may have the luxury of not only having external biometrics accessible to them, but realize the value proposition of additional biometrics normally derived by being scanned or measured by much more expensive and inaccessible BMD's.

Imaging body composition in obesity and weight loss: challenges and opportunities, an ideal imaging method that incorporates the characteristics of being non-invasive, rapid, sensitive, and specific would have significant utility in addressing the limitations of current methodologies discussed earlier and enhance our understanding of metabolic risk in various populations. It is also preferred that such a method be convenient and cost effective for use in both clinical and research settings.

In one embodiment, to derive implicit biometrics, the system may scan or measure a sample of a population with both a BSI body scanner and a non-BSI body scanner or other body measurement device, and then use statistical means to build a correlation. Some correlations may not exist, for natural reasons, as there may not be a true physical relationship between the two quantities. (e.g., the size of someone's wrist is not likely correlated with their risk of diabetes). However, other biometrics may have strong physical basis for being correlated (e.g. the size of someone's waist is strongly correlated with the risk of diabetes). In this regard, there is a large body of data from research studies that already exists showing a correlation between anthropometric measurements and obesity-related.

In one embodiment, anthropometric measurements, measured from BSI body scanning correlated with biometrics (e.g. body fat %, lean mass, etc) from body composition analysis BMD's (DXA, Hydrostatic weighing, Bod Pod, BIA, etc), are used to arrive at body composition from scan data. In one example, the system may apply the method to a Taiwanese population. The BSI BMD used in this example is the body scanning system described herein, and the non-BSI BMD used to calculate body composition is the InBody 230 (copyright 2014), a body composition analysis BMD developed and sold by InBody Co., LTD., located at Bldg. 54, Nonhyeon-ro 2-gil, Gangnam-gu, Seoul 06313, Korea. Note that the following method is not limited to the BSI or non-BSI BMD's chosen for this example, nor is it limited to the population sample chosen or the statistical method used to derive a correlation between databases.

Figure 65:
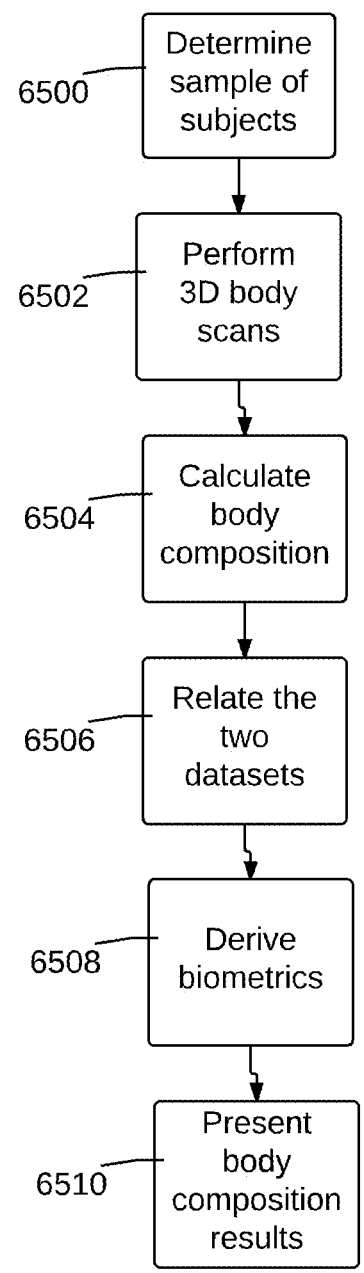
FIG. 65 is a flow diagram illustrating the steps performed in one embodiment for relating biometrics derived from a BSI 3D body scanner including anthropometric measurements to data produced from a non-BSI body composition analyzer.
Figure 66:
FIG. 66 is a screen shot for illustrating the anthropometric measurements derived from a 3D body scan, and the resulting body fat % value according to one embodiment.

With reference to FIG. 65, a flow diagram illustrating the steps performed by the system is shown for correlating BSI-derived anthropometric measurements and other biometrics to non-BSI-derived body composition biometrics. In step 6500, the system may determine a statistically relevant sample of subjects from a population of interest to relate anthropometric measurements to body composition. In step 6502, the system performs 3D body scans using a BSI BMD and extract anthropometric measurements. A detailed description of how the they system may extract body measurements from 3D scan data below under the section entitled Create and Edit Biometrics from BSI BMDs. In step 6504, the system may calculate body composition from the same subjects using a non-BSI BMD. In step 6506, the system may relate the two datasets using statistical means, in order predict one biometric from another. In this case, predicting body fat % (a biometric) from anthropometric measurements. In step 6508, biometrics (eg., anthropometric measurements) derived from a BSI BMD are input to produce a body composition result. FIG. 66 provides an example of a screen shot for illustrating the anthropometric measurements derived from a 3D body scan, and the resulting body fat % value according to this example.

Figure 67:
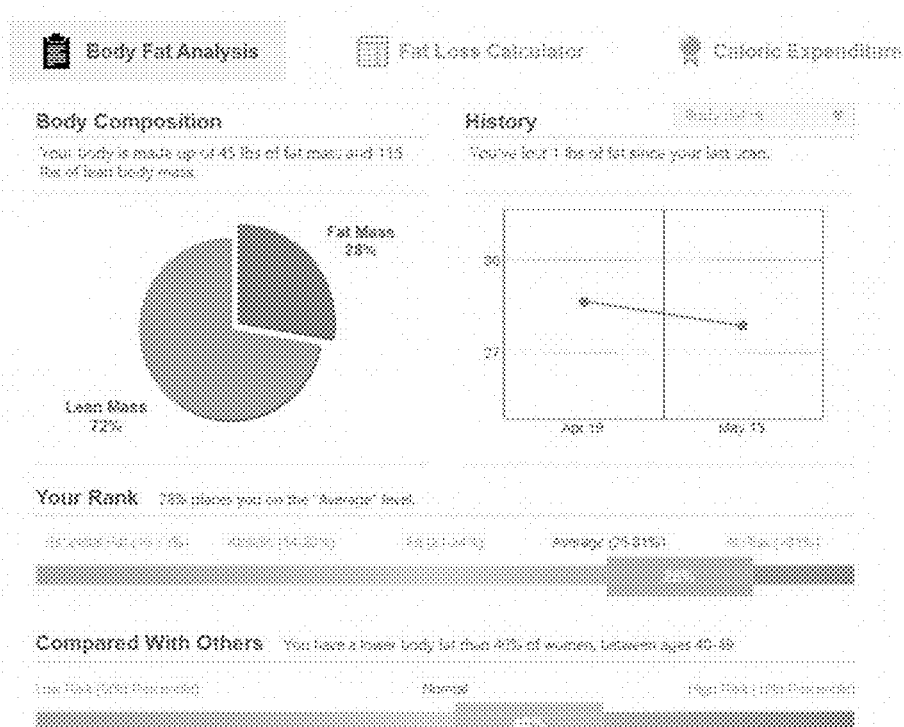
FIG. 67 is a screen shot to illustrate an example of how one embodiment may present body composition results to the user or consumer.

In step 6510, the body composition results may be presented to a BSI body scan subject or consumer 22. FIGS. 66-67 illustrate an example of how the system may present body composition results to the user or consumer 22. Additionally, the body composition results can be used to derive additional implicit biometrics, for example, to display a ranking fitted to the body composition values of the entire population. A more detailed explanation of step 6510 is presented in the section below entitled Set and Track Fat Loss Goals Using Body Composition Biometrics, describing a method and system for setting and tracking fat loss goals using body composition biometrics.

In a real-World example using a Taiwanese population, in step 6500 of determining a sample population, a population of approximately 300 Taiwanese people of varying body dimensions, ages and genders who were members of a large chain of fitness gyms in Taiwan were used. It should be noted that this step is not limited to the sample size used, nor is it limited to this population. Any population of statistically significant size can be used.

In step 6502 to calculate key anthropometric measurements from 3D body scan data, the BSI system described herein was used to body scan each subject, and calculate body measurements it was believed would correlate to body composition of a subject. The ability to derive body composition from anthropometric measurements is known as 'the circumference method'. However, historically the application of this method has been very inaccurate due to human error when taking body measurements by hand. The system described herein improves on the precision and accuracy of the circumference method by extracting the relevant body measurements using a BSI BMD using the scanning system described herein. A more detailed description of how the system extracts body measurements from 3D scan data can be found in the section entitled Create and Edit Biometrics from BSI BMDs. However, other embodiments are not limited to using body measurements derived from the BSI system described herein. Any BSI BMD capable of calculating precise body measurements can be used.

It was determined in this example to use these measurements when correlating the measurements derived from the BSI BMD body scanning system described herein with the InBody body composition body fat % results:

mid-neck girth—girth of the neck midway between the base of the neck and the base of the jaw bicep girth—girth of the upper arm, taken of both left and right arms and averaged thigh girth—girth of the upper leg, taken of both left and right legs and averaged abdominal waist girth—girth of the waist taken approx. 1" above the navel height—the stated height of the subject weight—the weight of the subject, measured with a weight scale gender—the gender of the subject The determination of which measurements to use was made with the help of the 2009 paper by Kohli et al, *Using simple anthropometric measures to predict body fat in South Asians*, and the 2013 paper by Kalra et al, *Measures of body fat in South Asian adults*. In the 2009 (Kohli) paper it was concluded that the best correlation between anthropometric measurements and body composition (as measured using the DEXA body composition analyzer, a Non-BSI BSD that uses X-ray technology to determine lean vs fat mass in a body) occurred using a combination of skinfolds, waist circumference, hip circumference, humerus (upper arm) breadth, height, mass and age. In the 2013 (Kalra) paper it was determined that there was a correlation between anthropometric measurements and body composition (as measured using the BOD-POD body composition analyzer, a BSD that uses air-displacement plethysmography to determine body composition) when comparing BMI, waist circumference, hip circumference and waist-to-hip ratio.

The choice of which circumference method to use to calculate body composition is often determined according to the characteristics of the population set. In other populations, for example non-Asian Caucasian populations, a different set of anthropometric measurements may have a stronger correlation to non-BSI body composition results. One skilled in the art may recognize methods including the following:

Covert Bailey (as described in the book *The Ultimate Fit or Fat* by Covert Bailey)

YMCA

Modified YMCA

Department of Defense (DoD, or Navy method)

It should be noted that there may be correlations between other biometrics and body measurements in addition to, or independent of, the measurements used in this example. The decision made to use these measurements to derive a correlation with results from a body composition analyzer should not be construed to be a limitation of this invention, but only one proposed embodiment of the invention among potentially many.

In step 6504, to calculate body composition for the same subjects, in this example, body fat % (a component of body composition) was calculated for each subject by the InBody 230 method, (a BMD used to determine body composition via bio-electrical impedance). However, embodiments are not limited to using body composition or other biometrics derived from the InBody non-BSI system—any non-BSI BMD capable of calculating precise body composition can be used. For example, in the published literature mentioned above, non-BSI BMD's including the DEXA and the BOD-POD were used to calculate body composition.

In step 6506, relating the two data sets using statistical means, for this example, the sample data was split according to gender, and a formula for each gender was derived using linear regression to produce a body fat % value similar to the InBody 230 result when the key anthropometric measurements derived by the BSI BMD system described herein were input. An example formulation used in one embodiment comprises:

$$b0+b1*x0+b2*x1+b3*x2+ \ldots +b6*x5$$

Inputs:

b* values are the computed constants from the linear regression x0=abdominal waist girth x1=bicep girth x2=mid-neck girth x3=thigh girth x4=height x5=weight outputs:

body fat %

The statistical method used in this example is one of potentially many methods by which a correlation can be derived, and the use of linear regression is also non-limiting.

In step 6508, to generate body fat % value using the formula for a new 3D body scan, in this example, the system output a body fat % value using the formula noted in step

6506 above. The inputs are provided from the BSI BMD described herein, without any additional input from a body composition analyzer. With reference to FIG. 66, an example image showing the anthropometric measurements used as derived from a 3D body scan (highlighted on the 3D body scan), and the resulting body fat % value (on the left, highlighted) is shown.

In step 6510 the system may derive other implicit biometrics from the body fat % result, and present them to the user or consumer 22. The resulting body composition value can be displayed to the scan subject as shown in FIG. 66. Body composition and body fat % biometrics can be used along with published study results to derive other implicit biometrics related to body composition.

With reference to FIG. 67, a screenshot of a further presentation to the user or consumer 22 is shown. For example, subjects are shown a body fat % ranking based on a guideline by the American Council on Exercise (ACE) that ranks body fat % values for men and women (see *American Council on Exercise ACE Personal Trainer Manual $3^{rd}$ Ed.*, Ch. 6, Pg. 188, Table 6.14, General Body Fat Percentage Categories). It should be noted that the system is not limited to this ranking system, but this ranking system is currently used in one embodiment. In another example, subjects are shown a ranking that places them in a percentile compared to others in their gender and age range based on a guideline published by the American College of Sports Medicine (ACSM) that ranks body fat % values for men and women by age range (see ACSM's Resources for the Personal Trainer, 2013, Pg. 318, Table 12.3, Fitness Categories for Body Composition (% Body Fat) for Men and Women, By Age)

Other biometrics can be utilized in conjunction with the above biometrics to create a tool for setting fat loss goals. One embodiment has a fat loss calculator wherein body composition and rankings, as discussed above, coupled with calculations for RMR, caloric expenditure, activity level, and more are used to set goals, and predict outcomes. Detailed components and methods for the fat loss calculator is described in the section entitled Set and Track Fat Loss Goals Using Body Composition" biometrics below.

In another embodiment, as another example, anthropometric measurements may be taken, as measured from BSI body scanning correlated with risk or presence of obesity related diseases, as measured by MRI or CAT scans.

In one embodiment, anthropometric measurements derived from the BSI BMD described herein may be compared with data captured by non-BSI BMD's (for example, MRI or CAT scans) to determine risk for mortality and risk for obesity-related diseases. In another embodiment, the system may use a method whereby a correlation is made between BSI BMD biometrics and obesity-related disease as collected by a non-BSI BMD, and can follow the same or similar steps as previously shown in the examples above.

However, the collection of obesity related disease may require that a population of significant statistical size be tracked and biometrics collected over a long period of time, while also being 3D body scanned using a BSI BMD. BSI BMD biometric data collection is a new technology, and collection of this kind of long-term biometric data is ongoing.

In lieu of this data, for this example, published data is used showing the correlation between anthropometric measurements and obesity-related disease. The BSI BMD described herein was used to collect anthropometric measurements, and the conclusions of several large studies showing the correlation between those measurements and obesity-related disease were used to show that health risks can be determined via BSI BMD biometrics of scan subjects not participating in the studies.

Note that the following method is not limited to the BSI or non-BSI BMD's chosen for this example, nor is it limited to the population sample chosen or the statistical method used to derive a correlation between databases, or the published data making the correlation between anthropometric measurements and health risks.

Figure 68:
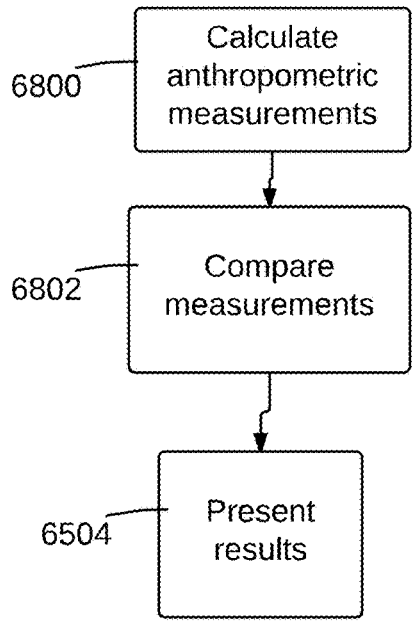
FIG. 68 is a flow diagram illustrating steps for derived risk of disease given anthropometric measurements.
Figure 69:
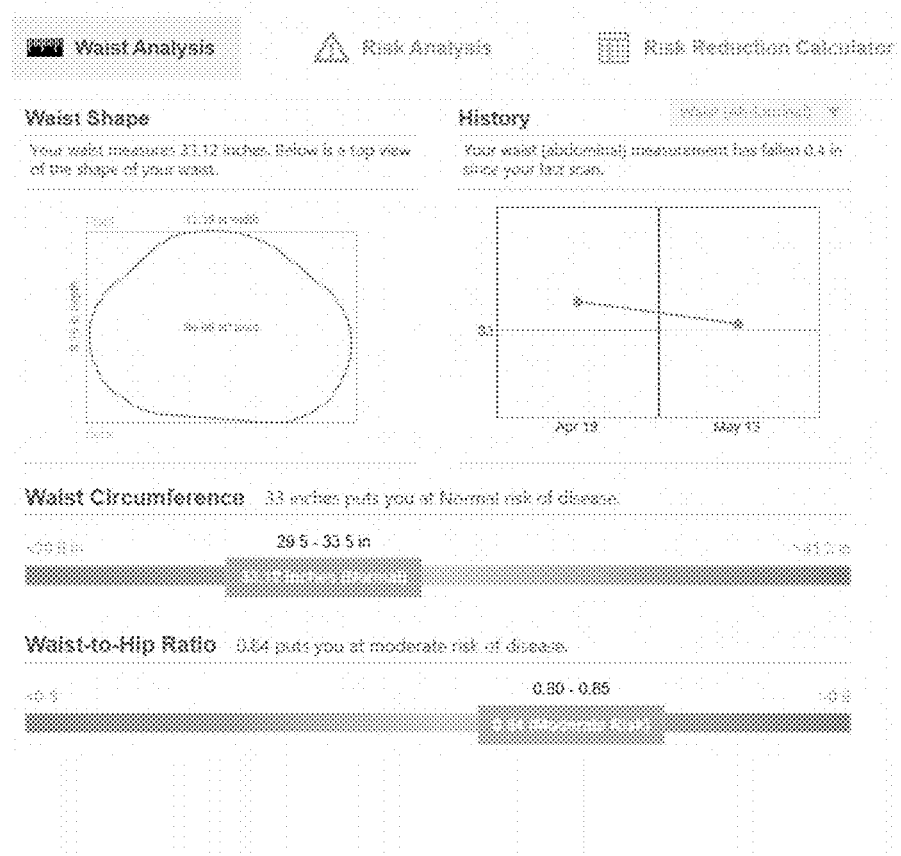
FIG. 69 is a sample screen shot showing images illustrating a waist circumference and waist to hip ratio, and the associated risks of cancer, cardiovascular disease, respiratory disease and all other diseases according to one embodiment.
Figure 70:
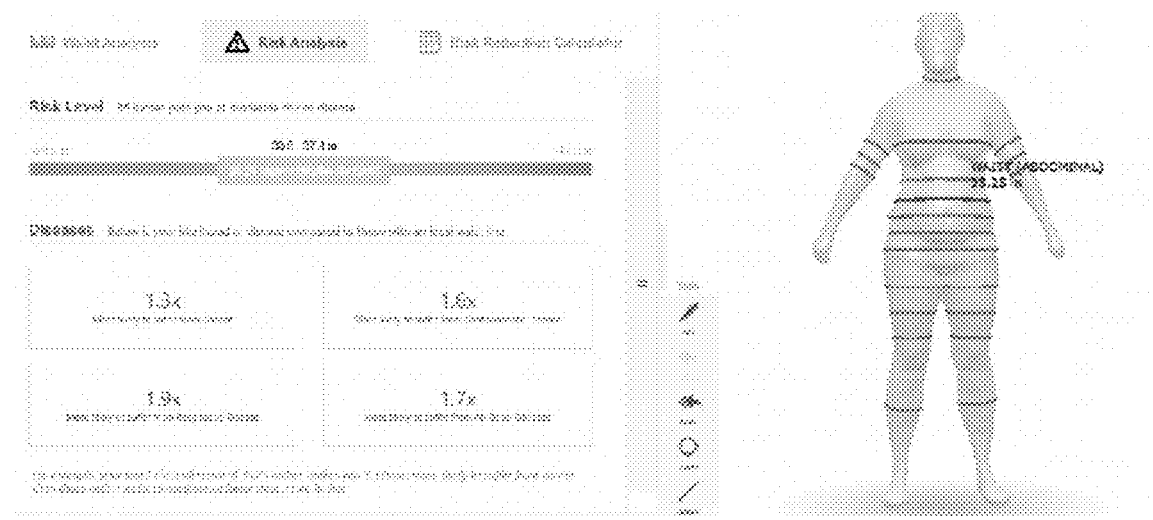
FIG. 70 is another sample screen shot showing images illustrating a waist circumference and waist to hip ratio, and the associated risks of cancer, cardiovascular disease, respiratory disease and all other diseases according to one embodiment.
Figure 71:
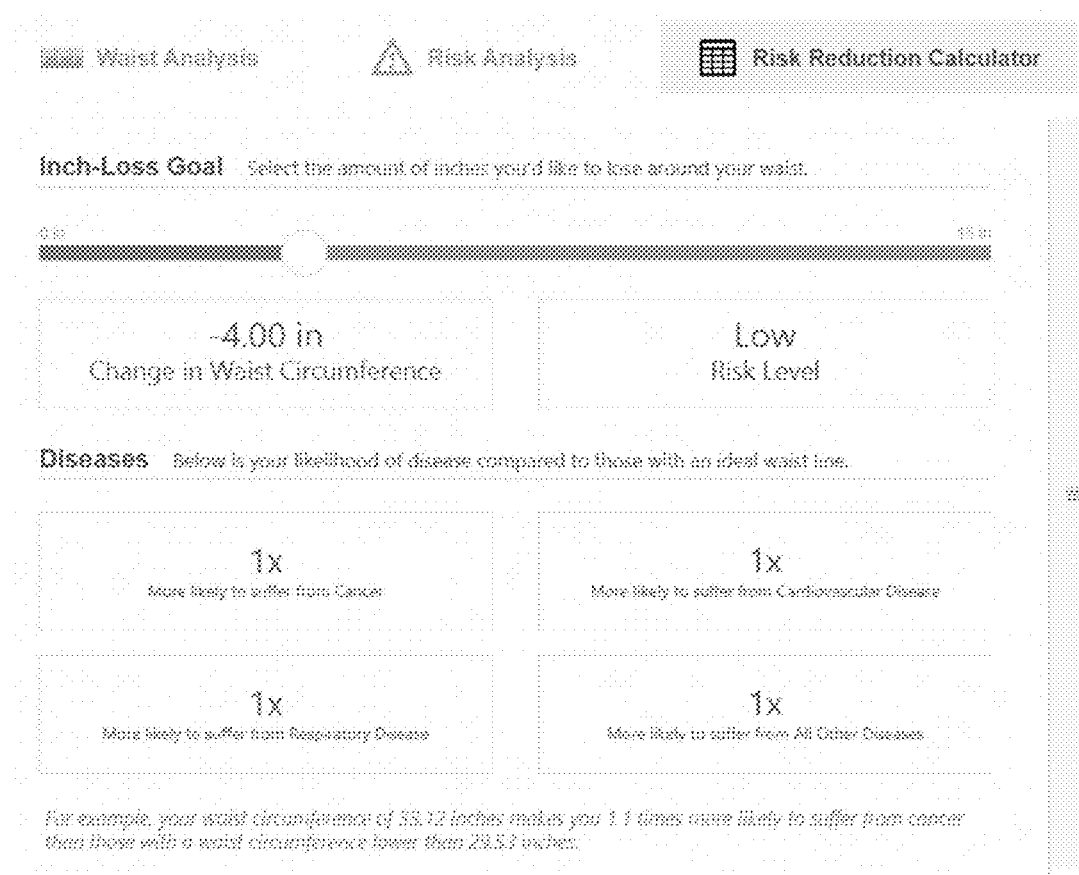
FIG. 71 is another sample screen shot showing images illustrating an interactive tool displaying the relationship between a reduced waist circumference and the associated reduced risks of cancer, cardiovascular disease, respiratory disease and all other diseases according to one embodiment.

With reference to FIG. 68, a flow diagram is shown illustrating steps for derived risk of disease given anthropometric measurements is shown. To briefly summarize, the steps are: Perform both 3D body scans using a BSI BMD and extract anthropometric measurements; compare measurements with conclusions in published data to derive risk for obesity-related disease; present the results to a 3D body scan subject. FIGS. 69-71 are sample screen shots showing images illustrating a waist circumference and waist to hip ratio, and the associated risks of cancer, cardiovascular disease, respiratory disease and all other diseases (overall mortality).

In more detail, in step 6800, the system calculates key anthropometric measurements from 3D body scan data. The BSI system described herein may be used to body scan each subject, and calculate body measurements that correlate to obesity-related disease. Historically, the collection of anthropometric measurements has been very inaccurate due to human error when taking body measurements by hand. This improves on the precision and accuracy of anthropometric measurements by extracting the relevant body measurements using a BSI BMD, for example the Styku system. A detailed description of how the system extracts body measurements from 3D scan data is described in the section below entitled Create and Edit Biometrics from BSI BMDs. However, other embodiments are not limited to using body measurements derived from this BSI system—any BSI BMD capable of calculating precise body measurements can be used.

It was determined in this embodiment to use these measurements when comparing measurement values with the conclusions made by published studies for obesity-related disease:

abdominal waist girth—girth of the waist taken approx. 1" above the navel hip girth—girth of the hip taken at the fullest point of the buttocks waist-to-hip ratio—the ratio derived by dividing the abdominal waist girth by the hip girth It should be noted that there may be correlations between other biometrics and body measurements in addition to, or independent of, the measurements used by this embodiment. The decision made to use these measurements to derive a correlation with results from published studies should not be construed to be a limitation, but only one embodiment of among potentially many.

In step 6802, the system may compare measurements with conclusions in published data. The correlations between anthropometric measurements and obesity-related disease and/or death were determined in part by the following studies. Note that this example uses the conclusions and data provided by these studies, but the other embodiments are by no means limited to the results of only these studies:

Obesity and the risk of myocardial infarction in 27 000 participants from 52 countries: a case-control study, Yusuf et al, 2005.

Waist Circumference and All-Cause Mortality in a Large US Cohort, Jacobs et al, 2010.

Additional data regarding the correlation of waist circumference, hip circumference, and waist-to-hip ratio to obesity-related disease including diabetes, myocardial infarction, cardiovascular disease, overall mortality and others is outlined well in a report performed by the World Health Organization in 2008.

In step 6804, the system may present results to a user or consumer 22. With reference to FIGS. 69-71, screenshot images illustrate a presentation of derived risk of disease given anthropometric measurements taken by the one embodiment of the measurement system for waist circumference, and waist-to-hip ratio.

The available sizes, fit specifications of apparel, footwear, and related accessories (AFA) are also considered biometrics (henceforth, AFA biometrics). The BSI BMD can be made capable of determining AFA biometrics in a multitude of ways.

One obvious way, in the prior art, is simply to compare a subject's anthropometrics measurements in a region of the body (e.g. waist circumference) with a database of AFA biometrics (for example a garment's waist measurements in each size) for products. The prior art is filled with examples of how to do this calculation to arrive at a recommended size and/or fit rating for products. Indeed, Styku developed recommendations models to make these kinds of comparisons as well.

However, these methods rely heavily on acquiring/aggregating a tremendous amount of garment data or previously known AFA biometrics, which in practice is very challenging and nearly impossible considering the incredible speed of which fashion changes and specifications become obsolete. Therefore a new method has been developed for the system herein.

In this new method, one can implicitly determine AFA biometrics, for example a garment's size, without explicitly measuring or acquiring a garment's dimensions. In one embodiment, the system extracts measurements of a 3D body scan via the BSI BMD, and asks users to fill out a form listing their favourite products while noting the size of each of their products. This represents a node or connection that pairs a garment size (in this example) with a set of body measurements. A collection of these pairs that relate all available sizes for a particular product to body measurements is typically called a size chart.

In the prior art, these charts are built manually, by surveying a small sample of a population using a measuring tape and having each subject try-on each size of the product. As a result, these manual size charts are often inaccurate and/or imprecise. The system herein improves on this by crowdsourcing these nodes, therefore allowing them to dynamically change and improve. With time and increased usage of the system, statistical samples become more representative of the true population and of the true garments AFA biometrics.

Also by virtue of using the precise anthropometric measurements, in place of manual hand measurements using a tape measure, the accuracy and/or precision of these charts is greatly improved. This is called a virtual size chart.

Figures 72, 73:
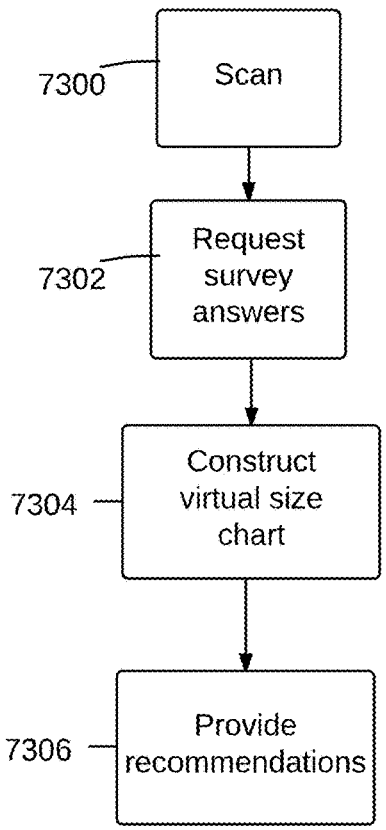
FIG. 72 is a flowchart outlining the steps taken when creating a virtual size chart according to one embodiment.
FIG. 73 is a sample online survey form that may be presented according to one embodiment.

With reference to FIG. 72, a flowchart outlining the steps taken when creating a virtual size chart is shown. In step 7300, the system may perform a 3D body scan, using the BSI BMD described herein to extract anthropometric measurements. A detailed description of how the system extracts body measurements from 3D scan data can be found below in the section entitled Create and Edit Biometrics from BSI BMDs. In step 7302, the system may request via a survey or form, that the subject enter one or more of their favorite products (but not limited to only their favorites) and in what size. A sample online survey form that may be presented is shown in FIG. 73.

Figure 74:
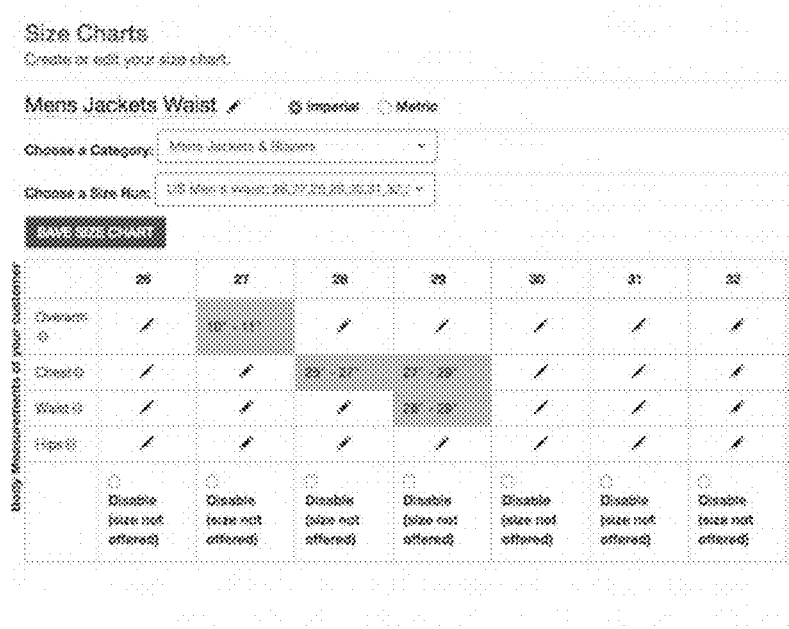
FIG. 74 is a sample virtual size chart that may be created according to one embodiment.

With reference back to FIG. 72, in step 7304, the system may then dynamically build a virtual size chart that relates a body's dimensions or some range of body measurements with a particular AFA biometric, such as a garment size. With reference to FIG. 74, a screenshot of an example size chart is shown.

Figure 75:
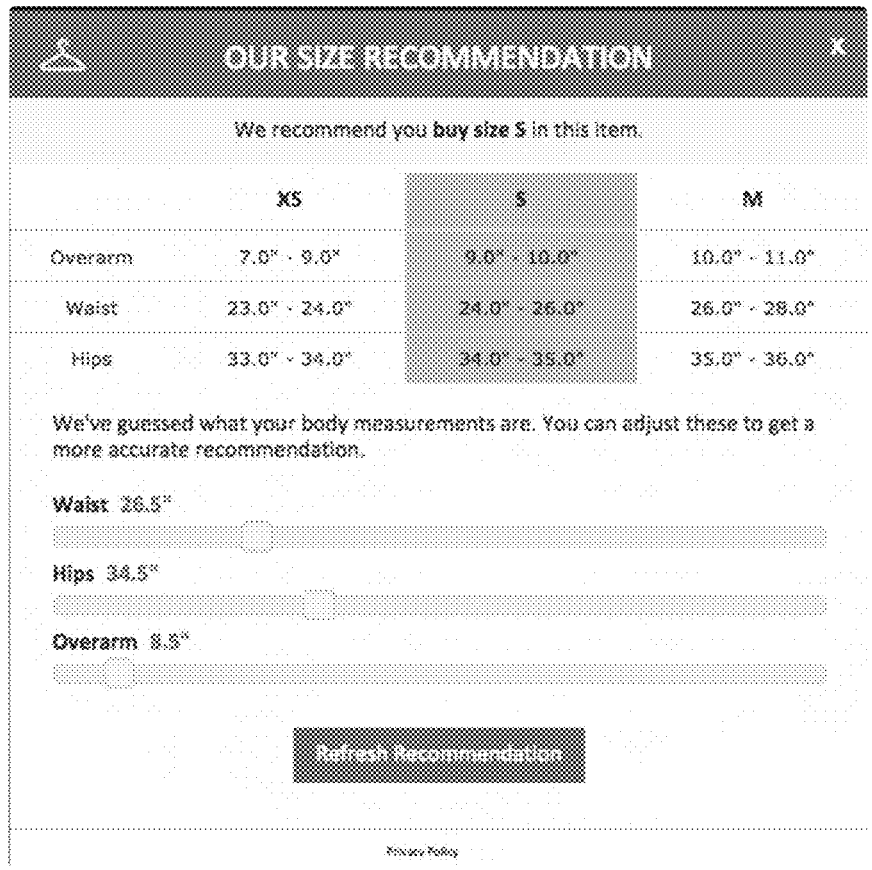
FIG. 75 is a sample screen shot showing the recommendations according to one embodiment.

With reference back to FIG. 72, in step 7306, the system may then provide recommendations for the same subject or customer 22 for products where virtual size charts already exist. A sample screen shot showing the recommendations is in FIG. 75.

Set and Track Fat Loss and Body Surface Shape Change Goals Using Body Composition Biometrics In the fitness industry, and in health and wellness overall, motivating clients to continue along their fitness journey and stay committed to their fitness goals is a major challenge, both for the member and for the fitness professional that may be advising or assisting them.

In a commercial setting the prior art includes many different software tools and methods for using biometrics like body composition or body fat as a means for assessment of someone's current fitness level with respect to standards and with respect to others in that population.

The prior art is also filled with examples of how to build on that assessment to develop a goal for fat loss, or for achieving some higher level of fitness, or to achieve better health. Indeed, the system described herein provides a novel way for determining body fat from anthropometric measurements.

Although assessing a member's fitness or health level in terms of body composition is valuable, one still needs a plan for how to take action to reduce their body fat. In the system described herein, a method and system is disclosed where once a fitness trainer has measured body fat via BSI device or other method, they can use the described tool to allow a user to select how much fat they would like to lose and how much activity per week they would be willing to commit as inputs. Based on these inputs, the system calculates when they will reach their goal, how much of a daily calorie deficit that would be required and finally, what is the maximum calories per day that should be consumed. The method is both unique in its user experience and comprehensive in its presentation.

The system herein provides a novel way to correlate fitness and body composition related biometrics including body fat %, body fat ranking (by ACE), caloric expenditure, activity level, RMR, circumference measurements, body shape images and more to provide a BSI scan subject (or other end-user) with the ability to set fat-loss goals and track progress toward those goals.

In one embodiment, the system uses a graphical user interface (GUI) that the user or subject can interact with to set fat loss goals and track progress toward those goals. The below method is intended as one example of how this invention can be created, but the invention is by no means limited to the implementation in this embodiment.

Figure 85:
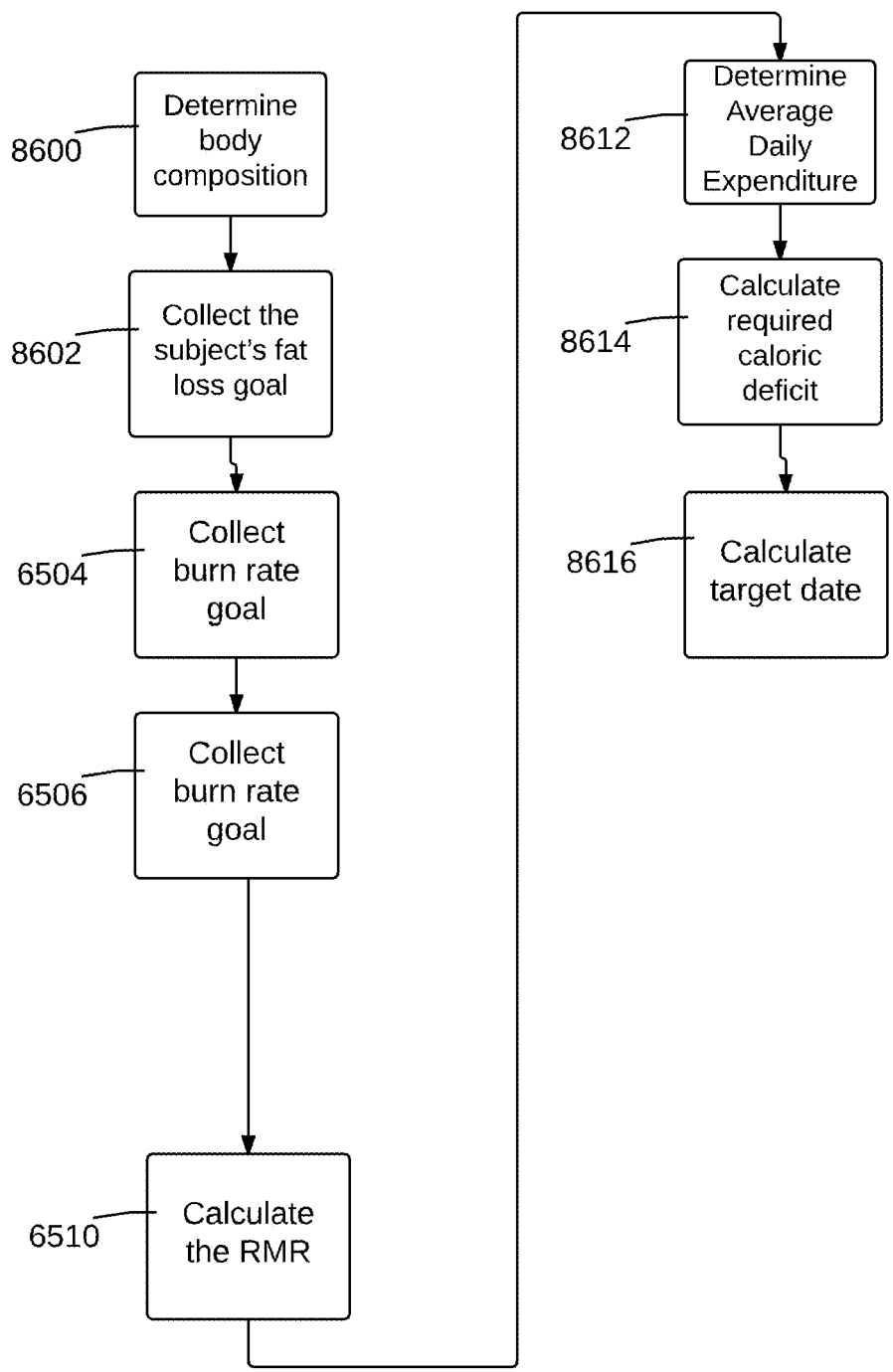
FIG. 85 is a flow diagram that illustrates the steps performed to calculate the date at which a subject's fat loss goal will be achieved according to one embodiment.

Given the subject's biometrics for:
body composition—fat mass and lean mass
fat loss goal—the amount of fat mass the subject wants to lose
burn rate goal—the amount of exercise the subject wants to perform, or the amount of Fat Mass the subject wants to lose per week of exercise the system returns their potential:
- Body fat % value—the body fat % they will achieve at completion of the fat loss goal
- ACE body fat % ranking—A fitness ranking derived from a guideline by the American Council on Exercise
- Target Date—predicted date at which the fat loss goal will be achieved The system also displays the client's:
- Resting metabolic rate (RMR, also known as Basal metabolic rate, or BMR)
- The amount of Calories burned in a day by the subject with the subject at rest
- Average daily caloric expenditure (Also known as Thermal Effect of Exercise, or TEE)
- The amount of Calories burned in a day by the subject with the subject exercising at the proposed activity level
- Recommended Caloric intake
- A proposed amount of Calories to be consumed by the subject to maintain a
- Caloric deficit required to achieve their fat loss goal
- Caloric deficit: The net amount of Calories that need to be burned daily to achieve the subject's fat loss goal With reference to FIG. 85, a flow diagram illustrates the steps performed to calculate a subject's body composition. A summary of the steps include: collect subject's fat loss goal; collect subject's burn rate goal; calculate subject's average daily caloric expenditure; calculate subject's caloric deficit; calculate target date; and display results to subject/user dynamically.

In more detail, in step 8600, the system first may calculate a subject's body composition, including the fat mass and lean mass. Body fat % in this example is calculated via anthropometric measurements extracted by a BSI BMD, for example the BSI BMD described herein, according to one or more methods, for example by the method described in the above examples and in the section entitled Implicit Determination Of Biometrics From Body Surface Imaging Devices. Given the weight of the scan subject and the body fat % value, the system may determine a fat mass (value of weight of the fat in the body) using the formula:

$$\text{Subject Weight} * \text{Body Fat \%}.$$

For example, a woman whose body weighs 120 lbs and has a body fat % of 27% would have a Fat Mass weight of (120*0.27=) 32.4 pounds. (round up to 33 lbs). The remainder of the woman's weight is made up of Lean Mass (The value of weight of non-fat in the body). In this case, our subject's Lean Mass is (120−33=) 87 lbs.

Figure 86:
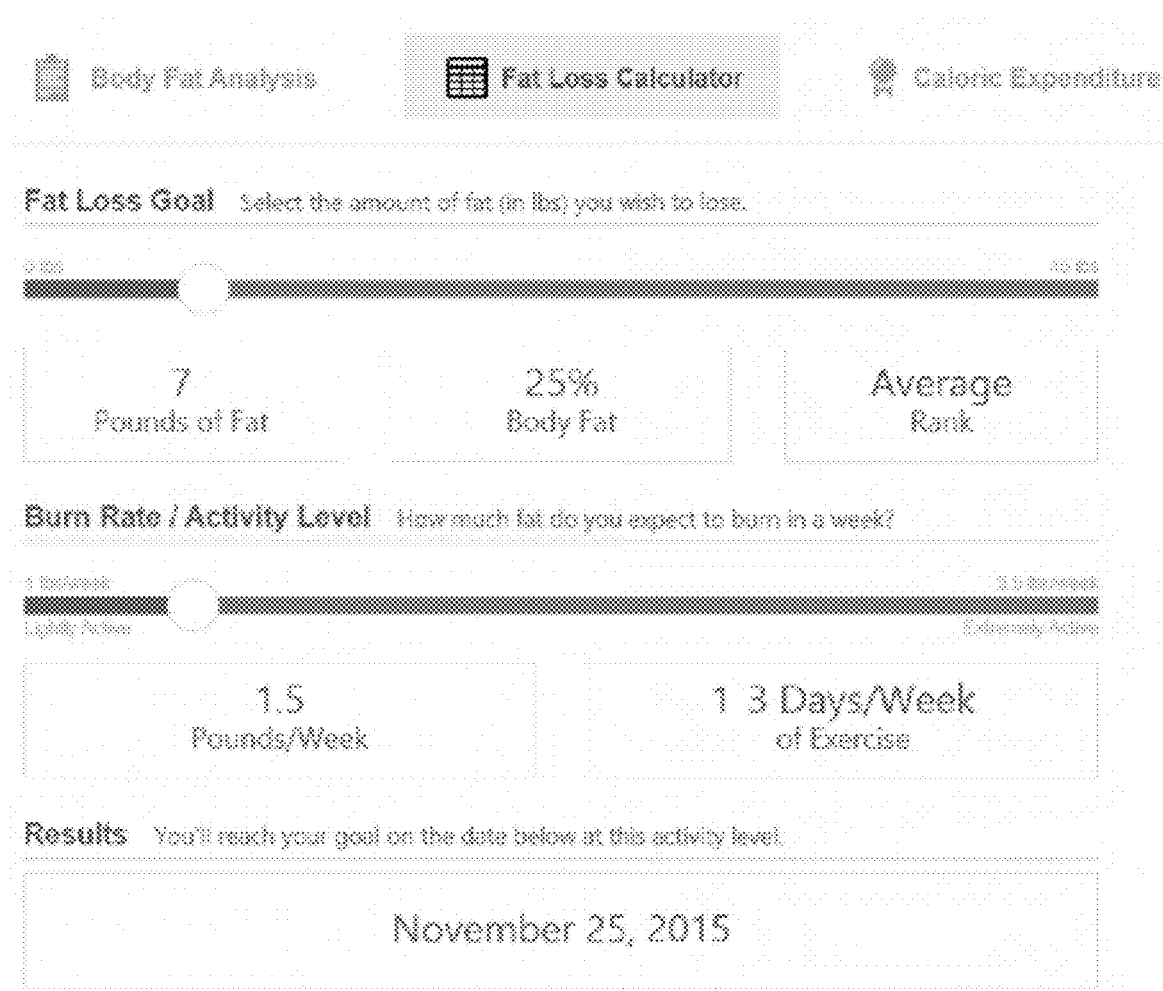
FIG. 86 is a screenshot that illustrates a GUI used by this embodiment of the invention to set a fat loss goal according to one embodiment.
Figure 87:
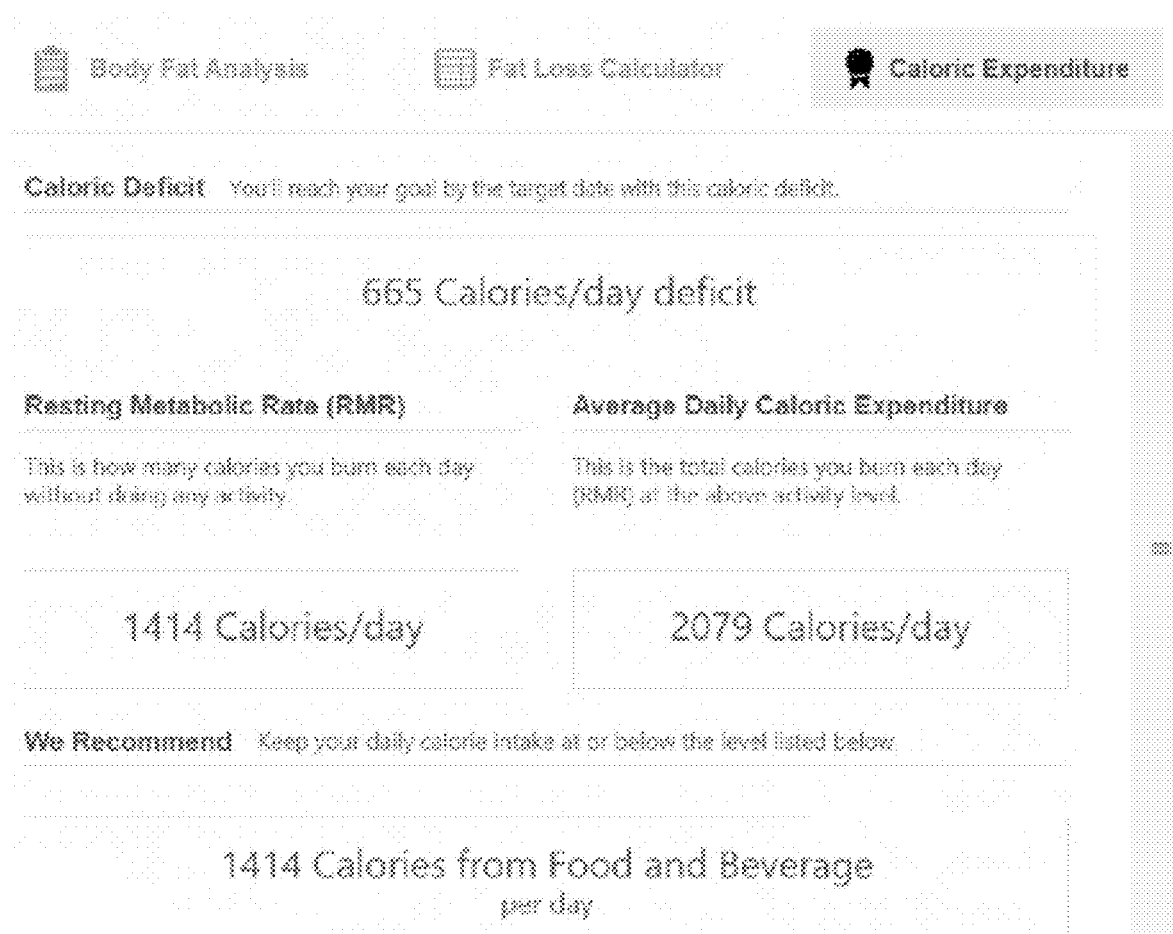
FIG. 87 is a screen shot for caloric expenditure according to one embodiment.

In step 8602, the system may collect the subject's fat loss goal. A GUI used to allow a user to input a fat loss goal. With reference to FIG. 86, a screenshot illustrates a GUI used by this embodiment of the invention to set a fat loss goal while FIG. 87 is a screen shot for caloric expenditure. A fat loss goal is defined as the amount of fat mass the subject wants to lose. In this embodiment, the GUI consists in part of a slider that can be interacted with by dragging left to right. As the user drags the slider for fat loss goal to the right, the GUI updates to display other predicted biometrics that the subject will achieve if they meet their goal, including:
- Pounds or KG of Fat loss—amount of fat mass that will be lost
- Potential Body Fat % Value—the new body fat % value when the fat mass is lost
- Potential ACE Body Fat % Ranking—the new ACE ranking when the fat mass is lost The Pounds or KG of Fat Loss field updates as the user changes the fat loss goal slider. The Potential Body Fat % Value field is updated every time the user changes the fat loss goal slider and is derived by applying this formula:

$$\text{Potential Body Fat \% Value} = (\text{Fat Mass} - \text{Fat Loss Goal})/\text{Subject Weight} * 100.0$$

For example, a woman with a Fat Mass of 33 lbs who has a Fat Loss Goal of 10 lbs and weighs 120 lbs would have a projected body fat % value of $((33-10)/120*100) = 19.17\%$.

The Potential ACE Body Fat % Ranking field is derived based on guidelines from the American Council on Exercise (ACE). The ACE has derived a ranking system for Body Fat % (see *American Council on Exercise ACE Personal Trainer Manual* $3^{rd}$ Ed., Ch. 6, Pg. 188, Table 6.14, General Body Fat Percentage Categories). FIG. 88 is a chart showing the ACE rankings for each gender. In this embodiment, a rank similar to the ACE ranking is determined and shown to a scan subject or other user of this system. For example, a woman with a projected body fat % of 19% would have an ACE ranking of Athletes. In one embodiment, the system displays the rank of Athletic to the user.

Shown below is a list of the ACE rankings side by side with our rankings:

| ACE Ranking: | System Ranking: |
| --- | --- |
| Essential Fat | Essential Fat |
| Athletes | Athletic |
| Fitness | Fit |
| Acceptable | Average |
| Obesity | At Risk |

In step 8604, the system may collect the subject's burn rate goal. With reference back to FIG. 86, the GUI allows a user to set a burn rate (also called in this embodiment an Activity Level) defined as an amount of fat mass that will be lost per week. In this embodiment, the GUI comprises a slider that can be interacted with by dragging left and right. As the user drags the slider for burn rate to the right, the GUI updates to display the resulting amount of fat mass per week that will be lost, and the number of days per week of exercise that would need to be performed to create that fat mass loss. The number of days per week of exercise displayed when the user sets a burn rate are based on activity level rankings provided in the revised Harris Benedict study done by Harris et al, (revised 1990), entitled, *A Biometric Study of Basal Metabolism in Man*. In this study, activity level is broken down into several rankings based on days of exercise per week. With reference to FIG. 89, a chart illustrating the Harris Benedict Activity Level rankings is shown.

The system may then calculate subject's average daily caloric expenditure. One skilled in the art will know that one accepted paradigm of the relationship between consumption of energy by the human body and fat mass is that one pound of fat mass is equivalent to 3500 Calories (kcals) of energy, and that to reduce fat mass, a body would have to consume a net amount of 3500 Calories. To put it another way, in order to lose one pound of fat mass, a subject must burn 3500 Calories more than the amount of Calories they take in (by food and drink).

In order to calculate a target date, defined in this embodiment as a projected date at which this subject will achieve their fat loss goal, in this embodiment we calculate the amount of energy (Calories), the subject will burn in a day while active at the level decided on by the burn rate goal. This value is referred to in this embodiment as the average daily caloric expenditure (also known in prior art as the thermic effect of exercise (TEE)).

In the steps to calculate average daily caloric expenditure, in one embodiment, the first step is to calculate RMR, step 6510. In this step of one embodiment, the system uses the Revised Harris-Benedict Formula based on the study done by Harris et al, (revised 1990), entitled, *A Biometric Study of Basal Metabolism in Man* to determine resting metabolic rate (RMR, also known to those skilled in the art as basal metabolic rate (BMR)). This method has a formula for men, and one for women, noted here:

Men:

$$\text{RMR calories per day}=(88.362+(13.397*\text{weightKilograms})+(4.799*\text{heightInCm})-(5.677*\text{age}))$$

Women:

$$\text{rmr calories per day}=(447.593+(9.247*\text{weightKilograms})+(3.098*\text{heightInCm})-(4.33*\text{age}))$$

For example, according to this formula, a 24-year-old female subject weighing 120 lbs would have an RMR of 1351 calories.

In step 8612, the system may determine the average daily caloric expenditure based on user-input burn rate and RMR. This embodiment uses data derived from the revised Harris-Benedict study noted above to apply a multiplier to the calculated RMR value to derive an average daily caloric expenditure value. The chart in FIG. 89 shows the multipliers to use based on the user's activity level ranking. For example, a subject with an RMR of 1351 Calories and a proposed Burn Rate of 1-3 days of exercise per week (1-1.5 pounds/week of fat mass loss) will have an Average Daily Caloric Expenditure of (1351 Calories*1.375=) 1858 Calories/day.

In step 8614, the system may calculate the subject's required caloric deficit. In order to reduce fat mass, calories consumed by food and drink must be less than the average daily caloric expenditure. This difference is known by this embodiment as Caloric Deficit. As noted above, common knowledge has it that one pound of fat mass is equivalent to 3500 Calories. Given the Burn Rate goal set by the user, a required Caloric Deficit is derived using this formula:

$$\text{Caloric Deficit}=\text{Burn Rate Fat Mass Pounds to Lose}*3500\text{ Calories}/7\text{ days}$$

For example, a subject whose Burn Rate is 1.0 pounds/week will have a Caloric Deficit of (1.0*3500/7=) 500 Calories. Additionally, a recommended Caloric Intake (defined as the amount of Calories a subject should consume to maintain the Caloric Deficit) can be made by applying this formula:

$$\text{Average Daily Caloric Expenditure}-\text{Caloric Deficit}$$

It should be noted that if the result of this formula is less than the RMR value, in one embodiment, it is recommended the RMR value is used instead. One skilled in the art knows that a subject should never consume less calories than their RMR in order to maintain a healthy body.

In step 8616, the system may calculate a target date. Given all of the information derived from the preceding steps, the system can predict a date at which a subject will achieve their fat loss goal (Target Date, in this embodiment) by adding the number of days needed to achieve the fat loss goal to today's date. The days needed to achieve the fat loss goal is calculated according to this formula:

$$\text{Days Needed to Achieve Goal}=(\text{Fat Loss Goal}*3500\text{Calories})/\text{Caloric Deficit}$$

Figure 91:
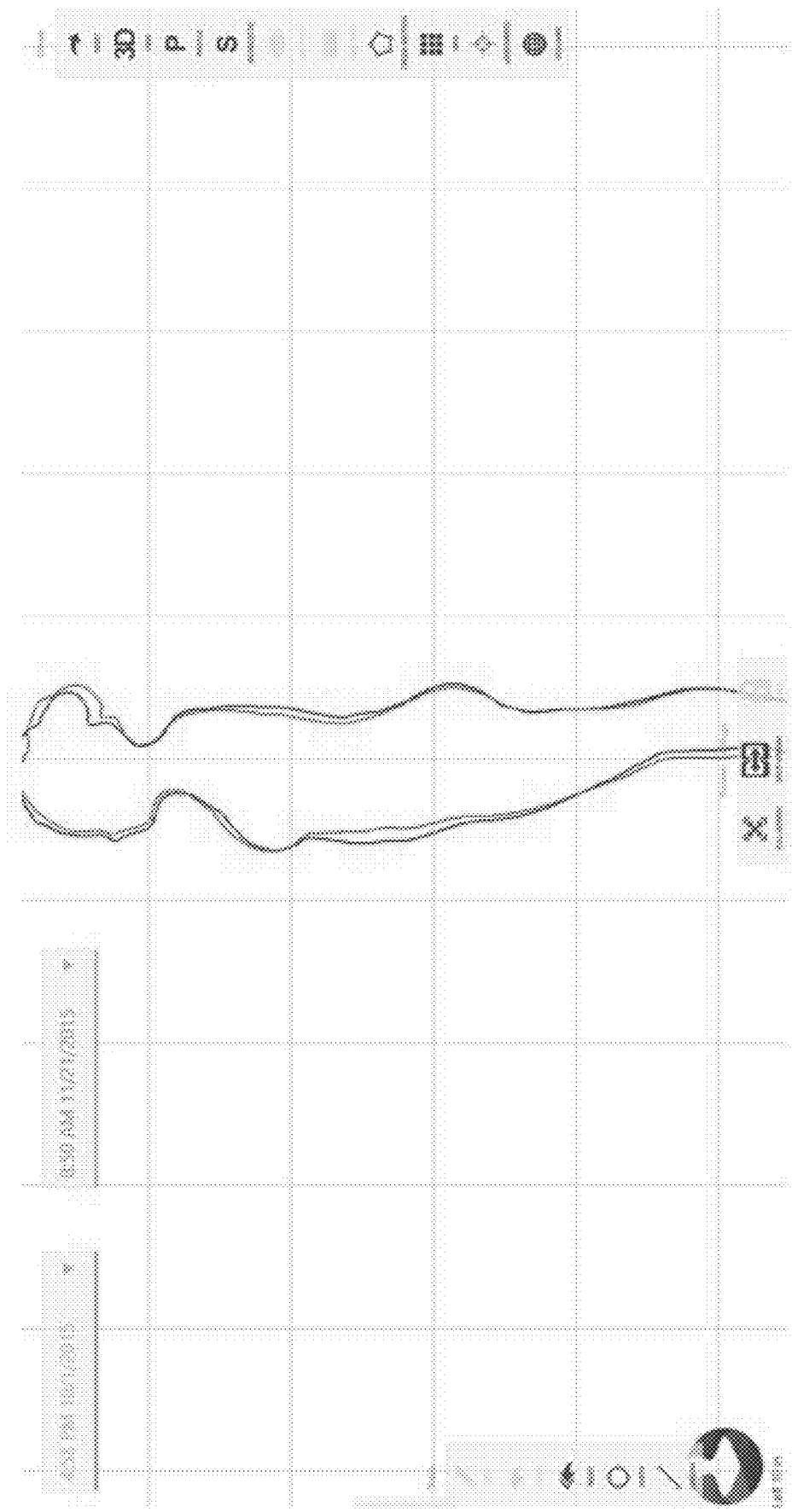
FIG. 91 is a screenshot that illustrates a GUI used by this embodiment of the invention to track surface shape differences of a subject's body at two different times.

With reference to FIGS. 86, 87 and 91, screen shots illustrate how display results may be presented to user or consumer 22 dynamically. In this regard, FIGS. 86 and 87 are screenshots illustrating how the above calculations for the following may be presented:

Body fat % value
ACE body fat % ranking
Target Date
Resting metabolic rate (RMR, also known as Basal metabolic rate, or BMR)
Average daily caloric expenditure (Also known as Thermal Effect of Exercise, or TEE)
Recommended Caloric intake
Caloric deficit FIG. 91 is a screenshot showing how changes in the body's surface shape can be presented, by outlining the body's outer edges and overlaying aligned outlines of one body on top of another.

These results may be generated dynamically in one embodiment based on user interaction with this embodiment's GUI. As the subject or user adjusts the values in the GUI, the calculations are performed again and the results displayed to the user.

The various embodiments described above are provided by way of illustration only and should not be construed to limit the invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed is:

1. A system for scanning a body to create scan data, comprising:
   a processor;
   a range camera capable of capturing at least a first set of depth images of the body rotated to 0 degrees, and at least a second set of depth images of the body rotated to x degrees, wherein x is >0 degrees, and x <360 degrees, including any clothing worn, the range camera including an infrared camera comprising an infrared light emitter that emits infrared light and at least an infrared sensor that reads reflected infrared light;
   a rotation device capable of rotating the body;
   a first set of computer instructions executable on the processor capable of calculating a first set of three dimensional points from the first set of depth images and a second set of three dimensional points from the second set of depth images;
   a second set of computer instructions executable on the processor capable of applying rotational and translational matrix transformations on the first set of three dimensional points to align said first set of three dimensional points with the second set of three dimensional points and then calculating and storing a square of the sum of the differences between the first set of three dimensional points with the second set of three dimensional points as an error;
   a third set of computer instructions executable on a processor capable of reconstructing the surface of the body by minimizing an error between the first and second set of three dimensional points by repeatedly making iterative and small changes to the matrix transformations and then re-calculating the error until the error is minimized;

a fourth set of computer instructions executable on the processor capable of applying poisson surface reconstruction to construct a mesh;

a fifth set of computer instructions executable on the processor capable of rigging the mesh with a biped bone structure, scaled and sized to appropriately fit the mesh;

a sixth set of computer instructions executable on the processor capable of utilizing the bone structure from within the mesh to identify one or more anthropometric points of measure; and a seventh set of computer instructions executable on the processor capable of extracting anthropometric body circumferences by calculating the convex hull associated with points around a specific region of the body's surface; and an eighth set of computer instructions executable on a processor capable of creating biometrics based on the anthropometric body circumferences.

2. The system of claim 1, comprising avatar processing software capable of creating an avatar from the mesh.

3. The system of claim 2, further comprising a display capable of displaying the avatar with the anthropometric body circumferences.

4. The system of claim 1, wherein the scan data includes data of the type selected from the group consisting of: scan data collected by the range camera, 3D geometry data created from raw scan data, body measurement data determined by analyzing raw scan data and 3D mesh data, 3D geometry data created to display measurements in 3D, and scan subject information including name, email address and demographic data including height, weight, age and gender.

5. The system of claim 1, further comprising a ninth set of computer instructions executable on a processor capable of directly extracting biometrics.

6. The system of claim 5, further comprising a graphical user interface allowing a user to view and modify data to alter the biometrics.

7. The system of claim 6, wherein the ninth set of computer instructions and graphical user interface are used to set and track fat loss goals using the biometrics.

8. The system of claim 1, wherein the rotation device is a platform.

9. The system of claim 1, wherein the rotation device is electrical.

10. The system of claim 1, wherein the rotation device is mechanical.

11. A method for scanning a body to create scan data, comprising:

rotating the body using a rotation device;

capturing, using a range camera, at least a first set of depth images of the body rotated to 0 degrees, and at least a second set of depth images of the body rotated to x degrees, wherein x is >0 degrees, and x <360 degrees, including any clothing worn, the range camera including an infrared camera comprising an infrared light emitter that emits infrared light and at least an infrared sensor that reads reflected infrared light;

calculating a first set of three dimensional points from the first set of depth images and a second set of three dimensional points from the second set of depth images;

applying rotational and translational matrix transformations on the first set of three dimensional points to align said first set of three dimensional points with the second set of three dimensional points and then calculating and storing a square of the sum of the differences between the first set of three dimensional points with the second set of three dimensional points as an error;

applying poisson surface reconstruction to construct a mesh rigging the mesh with a biped bone structure, scaled and sized to appropriately fit the mesh;

utilizing the bone structure from within the mesh to identify one or more anthropometric points of measure;

extracting anthropometric body circumferences by calculating the convex hull associated with points around a specific region of the body's surface; and creating biometrics based on the extracted body measurements.

12. The method of claim 11, comprising creating an avatar from the mesh.

13. The method of claim 12, further comprising displaying the avatar with the anthropometric body circumferences.

14. The method of claim 11, wherein the scan data includes data of the type selected from the group consisting of: scan data collected by the range camera, 3D geometry data created from raw scan data, body measurement data determined by analyzing raw scan data and 3D mesh data, 3D geometry data created to display measurements in 3D, and scan subject information including name, email address and demographic data including height, weight, age and gender.

15. The method of claim 11, further comprising altering the biometrics.

16. The method of claim 15, further comprising presenting a graphical user interface allowing a user to view and modify data to alter the biometrics.

17. The method of claim 16, wherein the graphical user interface is used to set and track fat loss goals using the biometrics.

18. The method of claim 11, wherein the rotation device is a platform.

19. The method of claim 11, wherein the rotation device is electrical.

20. The method of claim 11, wherein the rotation device is mechanical.

* * * * *